(12) United States Patent
Meyer et al.

(10) Patent No.: US 6,359,111 B1
(45) Date of Patent: Mar. 19, 2002

(54) OPIOID RECEPTOR TARGETING

(75) Inventors: Damon L. Meyer, Bellevue; Sudhakar Kasina, Mercer Island, both of WA (US)

(73) Assignee: NeoRx Corporation, Seattle, WA (US)

(*) Notice: Subject to any disclaimer, the term of this patent is extended or adjusted under 35 U.S.C. 154(b) by 0 days.

(21) Appl. No.: 09/321,054

(22) Filed: May 27, 1999

Related U.S. Application Data

(60) Provisional application No. 60/087,209, filed on May 28, 1998.

(51) Int. Cl.[7] ............... A61K 31/381; A61K 31/4355; A61K 51/04; C07D 489/00; C07D 489/09

(52) U.S. Cl. .............. 530/302; 424/1.45; 424/9.1; 424/9.44; 424/9.6; 514/2; 514/17; 514/250; 514/259; 514/279; 514/281; 514/282; 530/345; 544/233; 544/283; 546/35; 546/39; 546/40; 546/44; 546/45; 546/46; 534/10

(58) Field of Search ............... 424/1.45, 9.1, 424/9.42, 9.44, 9.6; 530/302, 330, 345; 514/2, 5, 6, 17, 185, 250, 259, 279, 281, 282, 562, 566, 616, 665; 546/34, 35, 39, 40, 44, 45, 46; 544/233, 283; 534/10, 11, 12, 13, 14; 562/556, 565, 566; 564/154

(56) References Cited

U.S. PATENT DOCUMENTS

| | | | |
|---|---|---|---|
| 4,231,923 A | 11/1980 | Miller et al. | 260/112.5 R |
| 4,257,773 A | 3/1981 | Miller et al. | 23/230 B |
| 4,263,255 A | 4/1981 | Miller et al. | 422/61 |
| 4,649,200 A | 3/1987 | Portoghese et al. | 546/26 |
| 4,767,718 A * | 8/1988 | Meyers | 436/501 |
| 4,816,586 A | 3/1989 | Portoghese | 544/340 |
| 5,089,249 A | 2/1992 | Fritzberg et al. | 424/1.1 |
| 5,298,622 A | 3/1994 | Portoghese et al. | 546/15 |
| 5,332,818 A | 7/1994 | Nagase et al. | 546/37 |
| 5,352,680 A | 10/1994 | Portoghese et al. | 514/279 |
| 5,411,965 A | 5/1995 | Reid et al. | 514/279 |
| 5,455,230 A | 10/1995 | Schiller | 514/18 |
| 5,457,208 A | 10/1995 | Portoghese et al. | 546/35 |
| 5,464,841 A | 11/1995 | Portoghese et al. | 514/279 |
| 5,552,404 A | 9/1996 | Chang et al. | 514/255 |
| 5,578,725 A | 11/1996 | Portoghese et al. | 546/35 |
| 5,591,602 A * | 1/1997 | O'Dowd | 435/69.1 |
| 5,622,946 A * | 4/1997 | Sessler et al. | 514/185 |
| 5,631,263 A | 5/1997 | Portoghese et al. | 514/279 |
| 5,658,908 A | 8/1997 | Chang et al. | 514/252 |
| 5,753,206 A | 5/1998 | McBride et al. | 424/1.69 |
| 5,772,981 A | 6/1998 | Govindan et al. | 424/1.49 |
| 5,804,595 A * | 9/1998 | Portoghese et al. | 514/428 |

FOREIGN PATENT DOCUMENTS

| | | | |
|---|---|---|---|
| EP | 271204 | * | 6/1988 |
| WO | WO 93/15062 | | 8/1993 |
| WO | 94/11021 | * | 5/1994 |
| WO | WO 98/04917 | | 2/1998 |

OTHER PUBLICATIONS

American Radiolabeled Chemicals, Inc., Technical Data Sheet, "ART 549 Naltrindole, [5', 7'-$^3$H]," Feb,. 17, 1997.

(List continued on next page.)

*Primary Examiner*—Jeffrey E. Russel
(74) *Attorney, Agent, or Firm*—Seed Intellectual Property Law Group PLLC

(57) ABSTRACT

A compound comprising a ligand portion which has binding affinity for an opioid receptor, and a therapeutically or diagnostically effective group selected from radionuclide chelating agents, fluorochromes, toxins, drugs, polyboron moieties, proteins, biological response modifiers, chemical moieties capable of binding to other molecules of interest, and radioisotopes selected from therapeutically effective alpha and beta emitters, and diagnostically effective gamma emitters. The compound may be used in a method of treating cancer, and in a method of imaging opioid receptors either inside or outside of the central nervous system.

17 Claims, 23 Drawing Sheets

OTHER PUBLICATIONS

Campa et al., "Characterization of δ Opioid Receptors in Lung Cancer Using a Novel Nonpeptidic Ligand," *Cancer Research 56*: 1965–1701, 1996.

Chang et al., "A Novel, Potent and Selective Nonpeptidic Delta Opioid Receptor Agonist BW373U86," *The Journal of Pharmacology And Experimental Therapeutics 267*(1): 852–857, 1993.

Channing et al., "Radiosynthesis of [$^{18}$F]3–Acetylcyclofoxy: A High Affinity Opiate Antagonist," *Int. J. Appl. Radiat. Isot. 36*(6): 429–433, 1985.

Cohen et al., "F–18–Cyclofoxy PET Imaging In Man," *The Journal of Nuclear Medicine 29*(5): p. 796, Abstract No. 228, 1988.

Dannals et al. "Radiosynthetic of an Opiate Receptor Binding Radiotracer: [$^{11}$C]Carfentanil," *Int. J. Appl. Radiat. Isot. 36*(4), 303–306, 1985.

Dasher et al., "Electrophilic Opioid Ligands. Oxygen Tethered α–Methylene–γ–lactone, Acrylate, Isothiocyanate, and Epoxide Derivatives of 6β–Naltrexol," *Journal of Medicinal Chemistry 35*(13): 2374–2384, 1992.

Frost et al., "Comparison Of C–11 Diprenorphine And C–11 Carfentanil Binding To Opiate Receptors In Man By PET," *The Journal of Nuclear Medicine 29*(5): p. 796, Abstract No. 231, 1988.

Frost et al., "Imaging Opiate Receptors in the Human Brain by Positron Tomography," *Journal of Computer Assisted Tomography 9*(2): 231–236, 1985.

Frost et al., "Multi–Compartmental Analysis Of C–11–Diprenorphine Binding To Opiate Receptors In Man By PET," *The Journal of Nuclear Medicine 29*(5): p. 796, Abstract No. 230, 1988.

Jones et al., "Regional cerebral opioid receptor studies with [$^{11}$C]diprenorphine in normal volunteers," *Journal of Neuroscience Methods 23*: 121–129, 1988.

Koolpe et al., "Opioid Agonists and Antagonists. 6–Desoxy–6–substituted Lactone, Epoxide, and Glycidate Ester Derivatives of Naltrexone and Oxymorphone," *Journal of Medicinal Chemistry 28*: 949–957, 1985.

Lever et al., "Synthesis Of Carbon–11 Labeled Diprenorphine: A Radioligand For Positron Emission Tomographic Studies Of Opiate Receptors," *Tetrahedron Letters 28*(35): 4015–4018, 1987.

Lever et al., "Synthesis Of N1'–([$^{11}$C]Methyl)Naltrindole ([$^{11}$C]MeNTI): A Radioligand For Positron Emission Tomographic Studies Of Delta Opioid Receptors," *Journal of Labelled Compounds and Radiopharmaceuticals XXXVI*(2): 137–145, 1995.

Luthra et al., "The Preparation of Carbon–11 Labelled Diprenorphine: a New Radioligand for the Study of the Opiate Receptor System In vivo," *J. Chem. Soc. Chem. Commun.20*: 1365–1456, 1995.

Olmsted et al., "A Remarkable Change of Opioid Receptor Selectivity on the Attachment of a Peptidomimetic χ Address Element to the δ Antagonist, Natrindole: 5'–[$N^2$–Alkylamidino)methyl]naltrindole Derivatives as a Novel Class of κ Opioid Receptor Antagonists," *J. Med. Chem. 36*: 179–180, 1993.

Otte et al., "Yttrium–90–labelled somatostatin–analogue for cancer treatment," *The Lancet 351*: 417–418, 1998.

Portoghese et al., "δ Opioid Antagonist Activity and Binding Studies of Regioisomeric Isothiocyanate Derivatives of Naltrindole: Evidence for δ Receptor Subtypes," *J. Med. Chem. 35*(2): 4086–4091, 1992.

Portoghese et al., "Application of the Message–Address Concept in The Design of Highly Potent and Selective Non–Peptide δ Opioid Receptor Antagonists," *Journal of Medicinal Chemistry 31*(2): 281–282, 1988.

Portoghese et al., "Naltrindole, a highly selective and potent non–peptide δ opioid receptor antagonist," *European Journal of Pharmacology 146*: 185–186, 1988.

Portoghese et al., "Opioid Agonist and Antagonist Activities of Morphindoles Related to Naltrindole," *J. Med. Chem. 35*: 4325–4329, 1992.

Portoghese, "Bivalent ligands and the message–address concept in the design of selective opioid receptor antagonists," *TiPs 10*: 230–235, 1989.

Schmidhammer et al., "Synthesis And Biological Evaluation Of 14–Alkoxymorphinans. 14.[1] 14–Ethoxy–5–Methyl Substituted Indolomorphinans With δ Opioid Receptor Selectivity," *Bioorganic & Medicinal Chemistry Letters 7*(2): 151–156, 1997.

Vogel et al., "Cyclic morphiceptin analogs: cyclization studies and opioid activities in vitro," *Int. J. Peptide & Protein Res. 48*: 495–502, 1996.

Weerawarna et al., "Isothiocyanate–Substituted κ–Selective Opioid Receptor Ligands Derived from N–Methyl–N–[(1S)–1–phenyl–2–(1–pyrrolidinyl)ethyl]phenylacetamide," *Journal of Medicinal Chemistry 37*(18): 2856–2864, 1994.

\* cited by examiner

R= H, COCH₃

OPIOID RECEPTOR TARGETING

CROSS-REFERENCE TO RELATED APPLICATION

This application claims benefit of U.S. Provisional Patent Application No. 60/087,209, filed on May 28, 1998, which application is incorporated herein by reference.

TECHNICAL FIELD

The present invention relates to therapeutic and diagnostic chemical agents, and more particularly to compounds that can bind to an opioid receptor while being conjugated to a therapeutically or diagnostically active group.

BACKGROUND OF THE INVENTION

Studies of the binding of various ligands in brain and other tissues have revealed the presence of several distinct receptors that bind to opioid compounds.

Three major categories of opioid receptors in animals are recognized, and these are commonly designated as δ (delta), κ (kappa) and μ (mu). Several review articles are available, which describe the research which elucidated the presence of these receptors, and the endogenous peptides and other compounds with which they interact. See, e.g., Akil et al., *Annu. Rev. Neurosci.* 7:223–255 (1984).

Three distinct families of peptides have been identified that interact with opioid receptors: the enkephalins, the endorphins, and the dynophins. Each family is derived from a distinct precursor polypeptide, designated proenkephalin, pro-opiomelanocortin (POMC), and prodynorphin, respectively. These peptides, and the precursors thereof, are generally found in viva associated with cells that mediate pain, however they may also be found associated with cells that regulate the autonomic nervous system and neuroendrocrinological functions, among others.

There are also numerous non-peptidic compounds that may serve as ligands for opioid receptors. Some compounds interact non-specifically with all opioid receptor types, while other compounds demonstrate a higher affinity for one receptor type than other types. Moreover, a compound may interact with a receptor as an agonist, a partial agonist, or an antagonist, at each receptor type. See, e.g., Martin, *Pharmacol. Rev.* 35:283–323 (1983). A discussion of many compounds, both peptidic and non-peptidic, which may serve as ligands for opioid receptors is found in Jaffe et al., Opioid Analgesics and Antagonists, Chapter 21 of *Goodman and Gilman's The Pharmacological Basis of Therapeutics*, 8$^{th}$ Ed. Ed. A. G. Gilman, T. N. Rall, A. S. Nies, P. Taylor. Pergamon Press (1990).

Opioid receptor ligands have been implicated in the mediation of many important physiological responses, including pain/analgesia, appetite, gastric secretion, epileptic seizures and other neurological disorders, renal function, cardiovascular responses, and traumatic paralysis, among others. Due to the physiological significance of opioid receptor ligands, extensive research has been conducted into developing new ligands which may be used in various therapies. See, e.g., U.S. Pat. Nos. 5,658,908; 5,631,263; 5,578,725; 5,552,404; 5,464,841; 5,455,230; 5,411,965; 5,352,680; 5,332,818; 5,298,622; 4,816,586; 4,649,200. See also Campa et al., *Cancer Res.* 56:1965–1701 (1996); Chang et al., PCT Published Application No. WO 93/15062; Chang et al., *J. Pharm. Exp. Therap.* 267,852–857 (1993); Dasher et al., *J. Med. Chem.* 35:2374–2384 (1992); Koolpe et al., *J. Med. Chem.* 28:949–957 (1985); Olmsted et al., *J. Med. Chem.* 36:179–180 (1993); Portoghese, *J. Med. Chem.* 35:4325–4329 (1992); Portoghese et al., *J. Med. Chem.* 35:4086–4091 (1992); Portoghese, *TiPS Reviews* 10:230–235 (1989); Portoghese et al., *J. Med. Chem.* 31:281–282 (1988); Portoghese, *Eur. J. Pharm* 146:185–186 (1988); Schmidhammer et al., *Bioorganic & Med. Chem. Let.* 7:151–156 (1997); Vogel et al., *Int. J. Peptide Protein Res.* 48:495–502 (1996); Weerawarna et al., *J. Med. Chem.* 37:2856–2864 (1994).

There is a need in the art for effective opioid receptor ligands which demonstrate specificity to one or more intended opioid receptors, and can deliver functional agents to the opioid receptor. The present invention fulfills this need and further provides other related advantages as disclosed herein.

SUMMARY OF THE INVENTION

In one aspect, the present invention provides a compound that includes a ligand portion (L) which has binding affinity for an opioid receptor, and a therapeutically or diagnostically effective group (X). The group (X) may be selected from, for example, radionuclide chelating agents, fluorochromes, toxins, drugs, polyboron moieties, proteins, biological response modifiers, chemical moieties capable of binding to other molecules of interest, and radioisotopes selected from therapeutically effective alpha and beta emitters, and diagnostically effective gamma emitters.

In another embodiment, the invention provides a therapeutic method using a compound described above. In this embodiment, a therapeutically effective amount of a compound of the invention is administered to a subject in need thereof, such that a compound of the invention binds to an opioid receptor. For instance, the invention provides a method of treating cancer comprising administering to a subject in need thereof a therapeutically effective amount of a compound of the invention. The cancer may be small cell lung cancer or other neuroendrocrine cancer.

In another embodiment, the invention provides a diagnostic method using a compound described above. In this embodiment, a diagnostically effective amount of a compound of the invention is administered to a subject in need thereof, such that the compound binds to an opioid receptor. The compound may be administered within or outside of the central nervous system. In a related embodiment, the invention provides for an in vitro diagnostic method using a compound described above. In this related embodiment, a diagnostically effective amount of a compound of the invention is contacted in vitro with an opioid receptor.

These and related embodiments of the present invention will be apparent upon reference to the following drawings and detailed description.

DETAILED DESCRIPTION OF THE INVENTION

Figure 1A:
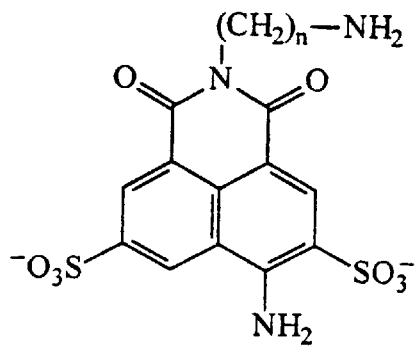
FIGS. 1A and 1B illustrate fluorochromes that may be conjugated to an opioid receptor ligand to prepare a diagnostically active compound of the invention.
Figure 1A:
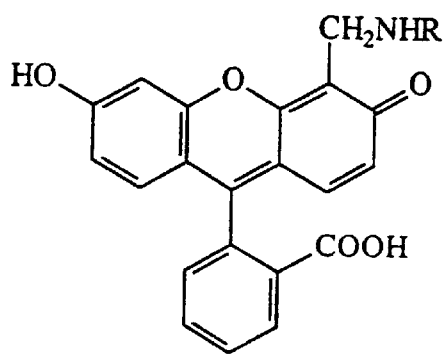
Figure 1A:
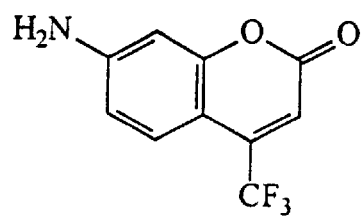
Figure 1A:
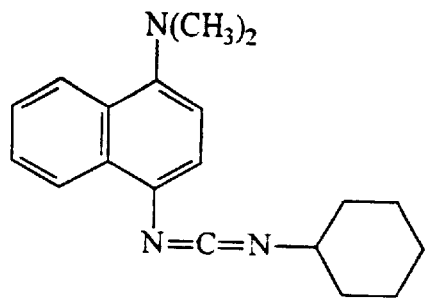
Figure 1A:
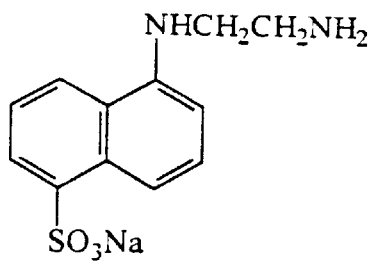
Figure 1A:
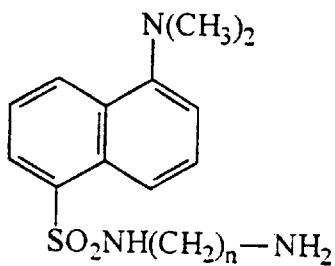
Figure 1A:
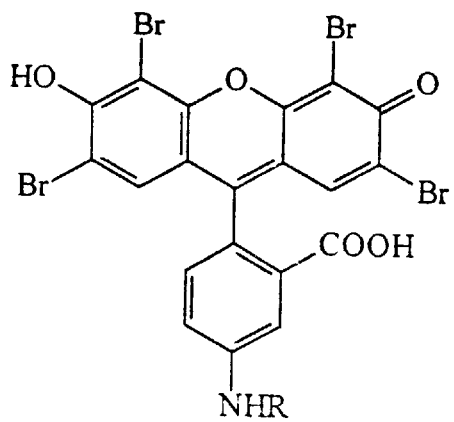
Figure 1A:
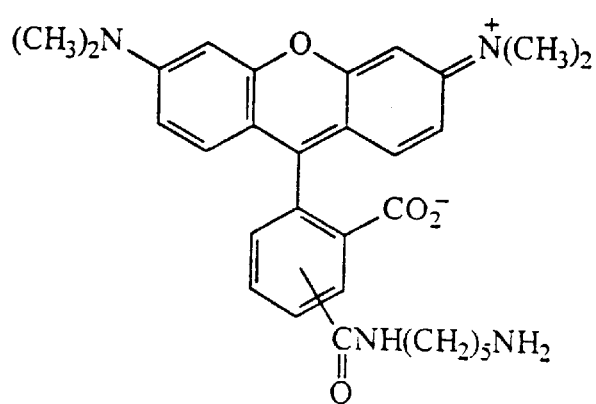

The present inventors have discovered compounds that contain both a ligand portion (L) having binding affinity for an opioid receptor, as well as a group (X) which imparts therapeutic or diagnostic efficacy to the compound. The group X may be, for example, any of a radionuclide chelating agent, fluorochrome (fluorophore), toxin, drug, a polyboron moiety, protein, a biological response modifier, a chemical moiety capable of binding to other molecules of interest, and a radioisotope selected from therapeutically effective alpha and beta emitters, and diagnostically effective gamma emitters.

In the compounds of the invention, the ligand portion (L) may be primarily specific for a δ opioid receptor, a κ opioid receptor, or a μ opioid receptor. Preferred compounds of the invention are primarily specific for δ opioid receptors. In the compounds of the invention, L may function primarily as an antagonist for a particular receptor, or it may function primarily as an agonist for a particular receptor. In other words, the compound may have affinity for only one receptor, or more than one receptor, and when it has affinity for more than one receptor, it may have high affinity for all receptors, or may have high affinity for only one or two receptors. Also, the compound may function entirely as an agonist, or entirely as an antagonist, or may demonstrate mixed agonist/antagonist efficacy for a particular receptor, where that efficacy is independent of the compound's efficacy at any other receptor.

The L portion of the compound may be peptidic, i.e., formed of a plurality of peptide bonds, where the peptide bonds are preferably the condensation product (amides) of amino acids. Suitable peptidic ligand are enkephalins, endorphins, dynorphins and peptidic physiological precursors thereof. Alternatively, the L portion of the compound may be non-peptidic. Suitable non-peptidic L portions include, without limitation, buprenorphine, butorphanol, fentanyl, meperidine, methadone, morphine, nalbuphine, nalorphine, naloxone, naltrindole, pentazocine, propoxyphene, sufentanil, and derivatives thereof. The non-peptidic ligand may be a morphine analog, where suitable morphine analogs include, without limitation, apomorphine, buprenorphine, butorphanol, codeine, dextrorphan, heroin, hydrocodone, hydromorphone, levallorphan, levorphanol, nalbuphine, nalmefene, thebaine, nalorphine, naloxone, naltrexone, oxycodone, oxymorphone, and derivatives thereof.

In other compounds of the invention, L has the formula

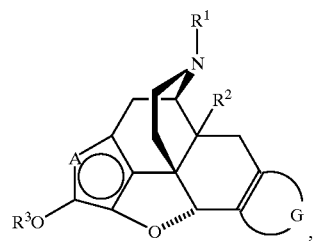

where a preferred stereochemistry is shown in the formula below:

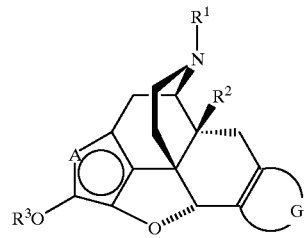

where G is selected from

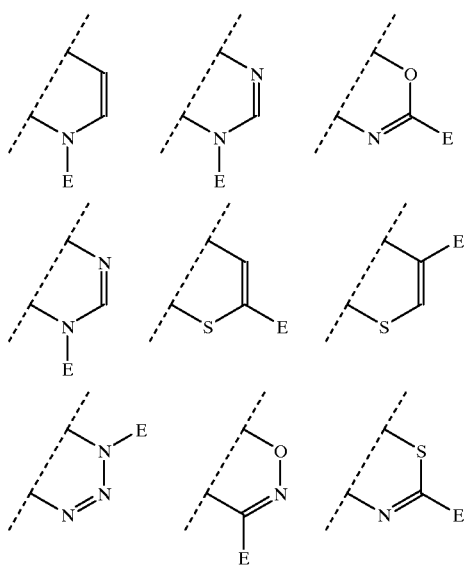

-continued

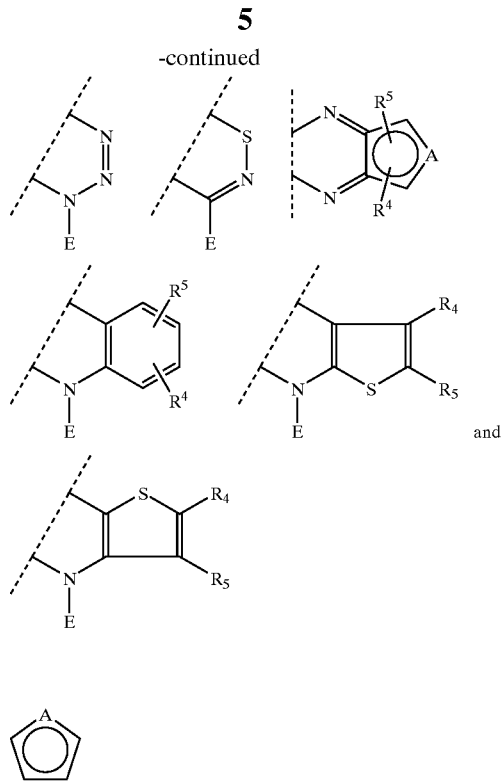

is a monocyclic, five- or six-membered, carbocyclic or heterocyclic, aromatic ring;

$R^1$ is selected from $(C_1-C_5)$alkyl, $(C_3-C_6$cycloalkyl)$C_1-C_5$alkylene, $(C_5-C_7$cycloalkenyl)—$C_1-C_5$alkylene, aryl, aralkyl, trans-$(C_4-C_5)$alkenyl, allyl and furan-2-yl$C_1-C_5$alkylene;

$R^2$ is selected from H, OH and $(C_1-C_5)$alkyl-C(=O)O—;

$R^3$ is selected from H, $(C_1-C_5)$alkyl and $(C_1-C_5)$alkyl-C(=O)—; and $R^4$ and $R^5$ are independently selected from a direct bond to E, H, F, Cl, Br, $NO_2$, CN, $COOR^1$, $NH_2$, $(C_1-C_5)$alkyl, $(C_1-C_5)$alkoxy or together are a benzo ring fused to

, with the proviso that one, but only one, of $R^4$ and $R^5$ may be a direct bond to E; and E is an extender arm, where E provides a stable chain of 2–60 atoms selected from carbon, oxygen, nitrogen and sulfur arm which covalently links together and distances the groups L and X.

In a preferred compound of the invention, L has the formula

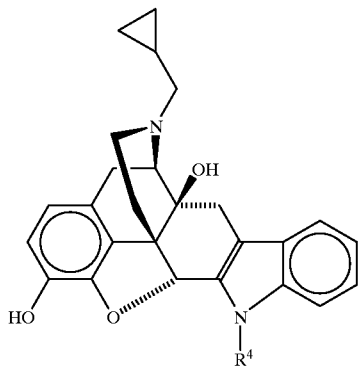

where a further preferred compound has the formula shown below, where $R^4$ is defined as above:

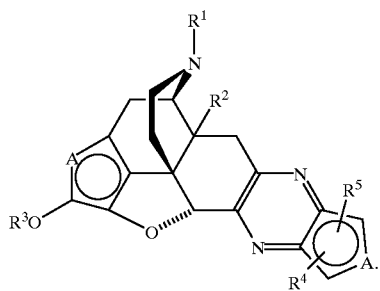

In another preferred compound of the invention, L has the formula

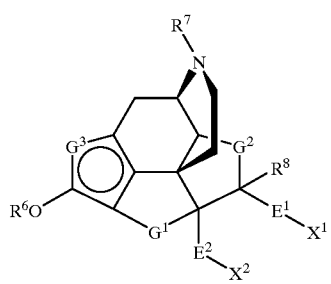

Another preferred compound of the invention has the formula

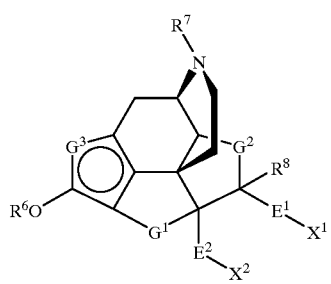

wherein, independently at each occurrence, $G^1$ is selected from O, S, NH and two hydrogens (when $G^1$ is two hydrogens, then each of the two carbon atoms to which $G^1$ is shown attached are themselves attached to one of the two hydrogen atoms);

$G^2$ is selected from —CH=CH— and —$CH_2$—$CH_2$—;

$G^3$ is selected from —C—C— and S, where the ring including $G^1$ is aromatic;

$R^6$ is selected from H, $C_1$–$C_5$alkyl and hydroxyl protecting groups including acetate;

$R^7$ is selected from H, $C_1$–$C_5$alkyl and ($C_3$–$C_5$cycloalkyl) $C_1$–$C_5$alkyl;

$R^8$ is selected from H, OH and a direct bond to $E^1$, such that $G^2$ is —CH=CH— when $R^3$ is OH;

$E^1$ and $E^2$ each represent an extender arm (E); and either both of $X^1$ and $X^2$ are radionuclide chelating groups or one of $X^1$ and $X^2$ is a radionuclide chelating group and the other of $X^1$ and $X^2$ is hydrogen.

Another preferred compound of the invention has the formula

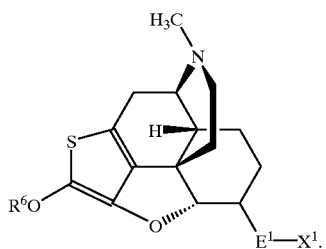

Another preferred compound of the invention has the formula

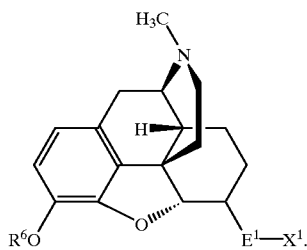

Another preferred compound of the invention has the formula

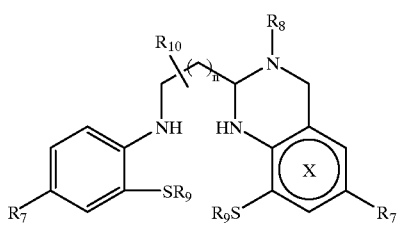

wherein, independently at each occurrence, $R_7$ is selected from —OH, —O—C(=O)—$C_{1-6}$alkyl, and —O—$C_{1-6}$alkyl;

$R_8$ is selected from hydrogen and $C_{1-6}$alkyl;

$R_9$ is selected from hydrogen, —C(=O)—$C_{1-6}$alkyl, —C(=O)-phenyl; hemithioacetals, hemithioketals, and sulfur protecting groups, such that two $R_9$ groups may be joined together as a direct bond, thereby linking two sulfur atoms as a disulfide linkage;

$R_{10}$ is selected from $C_{1-6}$alkyl and $C_{1-6}$alkoxy;

n is selected from 0 and 1; and

represents an aromatic or aliphatic ring.

In compound of the invention there is a least one "X" group, where the "X" group imparts diagnostic or therapeutic efficacy to the compound. Suitable "X" groups include, without limitation, a radionuclide chelating group, fluorochrome (fluorophore), toxin, drug, a polyboron moiety, protein, a biological response modifier, a chemical moiety capable of binding to other molecules of interest, and a radioisotope selected from therapeutically effective alpha and beta emitters, and diagnostically effective gamma emitters. Each of these types of "X" groups is described below.

A. Radionuclide Chelating Groups

In compounds of the invention, the radionuclide chelating group may be formed of two X groups which together provide sufficient chelating sites to bind a radionuclide. The two X groups are joined to the ligand portion of the compound at two sites, where extender arms may be present interposed between the ligand and the X groups, as shown in the formula

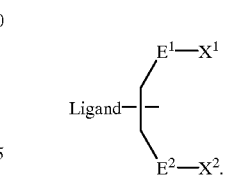

In compounds having $X^1$ and $X^2$ groups, each of $X^1$ and $X^2$ may have a structure selected from

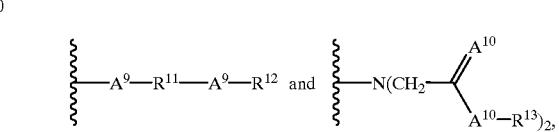

wherein, $A^9$ is an electron-donating moiety independently selected at each occurrence from O, S, C(=O)NH and N($R^{16}$), where $R^{16}$ is selected from hydrogen and pro-drug substituents selected from the group consisting of $C_1$–$C_3$alkyl, —C(=O)(H, $C_1$–$C_3$alkyl or Ar), —C(=O)—($C_1$–$C_3$alkylene)—N(independently H or $C_1$–$C_3$alkyl)$_2$, —C(=O)O—(H, $C_1$–$C_3$alkyl or Ar), —C(=O)CH(NH$_2$)(H, $C_1$–$C_3$alkyl or Ar), —($C_1$—$C_3$alkylene)—C(=O)O—(H, $C_1$–$C_3$alkyl or Ar), —($C_1$–$C_3$alkylene)—OC(=O)—(H, $C_1$–$C_3$alkyl or Ar), —($C_1$–$C_3$alkylene)—N(independently H or $C_1$–$C_3$alkyl)$_2$, —($C_1$–$C_3$alkylene)—NHC(=O)—Ar, —($C_{1-3}$alkylene)—CN, —($C_{1-3}$alkylene)—NO$_2$, and

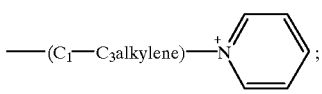

$R^7$ and $R^{10}$ each have a structure selected from $$-\underset{R^{18}}{\overset{R^{17}}{\underset{|}{C}}}_{1-4}- \quad \text{and} \quad \overset{A^{10}}{\underset{A}{\|}}\underset{}{\overset{}{\underset{}{\diagdown}}}\;;$$

$R^{17}$ and $R^{18}$ are selected from H, $C_1$–$C_6$ hydrocarbyl, —CN, —$NO_2$, —NO, —C(O$C_1$–$C_3$alkyl)=NH, —N=C=O, —N=C=S, and —C(=O)O$R^{19}$ where $R^{19}$ is $C_1$–$C_6$ hydrocarbyl;

$R^{12}$, $R^{13}$ and $R^{15}$ are selected from H and protecting groups for the $A^9$ or $A^{10}$ moiety to which the $R^{12}$, $R^{13}$ or $R^{15}$ is bonded;

$A^9$ and $R^{15}$ may together form —N(CH$_2$—COOH)$_2$; and
$A^{10}$ is selected from O and S.

In a preferred embodiment, the compound of the invention having $X^1$ and $X^2$ groups has the formula $$\text{Ligand}-\left\{\begin{array}{l}(CH_2)_{\overline{m}}-\underset{R^{20}}{\overset{|}{N}}-CH_2-(CH_2)_{\overline{p}}\overset{R^{21}\;R^{21}}{\underset{}{\diagdown\!/}}-S-R_{22}\\ \\ (CH_2)_{\overline{n}}-\underset{R^{20}}{\overset{|}{N}}-CH_2-(CH_2)_{\overline{q}}\overset{R^{21}\;R^{21}}{\underset{}{\diagdown\!/}}-S-R_{22}\end{array}\right.$$

wherein $R^{20}$ and $R^{21}$ are independently selected from hydrogen and methyl;

$R^{22}$ is independently selected from hydrogen, acm, EOE, THP, $C_1$–$C_6$alkyl, acetate, benzoyl and sulfur protecting groups; and each of m, n, p and q are selected from 0 and 1 such that when p+q=0 then m+n=0 or 1; and when p+q=1 then m+n=1; and when p+q=2 then m+n=1 or 2.

Alternatively, in compounds of the invention having $X^1$ and $X^2$ groups, those groups together may form the cyclic structure $$\underset{}{\overset{}{\diagup}}\!\underset{R^{11}}{\overset{A^9}{-}}\!\underset{R^{11}}{\overset{A^9}{-}}\!\underset{R^{11}}{\overset{A^9}{-}}\!\underset{}{\overset{A^9}{\diagdown}},$$

wherein, $A^9$ is an electron-donating moiety independently selected at each occurrence from O, S, C(=O)NH and N($R^{12}$), where $R^{12}$ is selected from hydrogen and pro-drug substituents selected from the group consisting of $C_1$–$C_3$alkyl, —C(=O)(H, $C_1$–$C_3$alkyl or Ar), —C(=O)—($C_1$–$C_3$alkylene)—N(independently H or $C_1$–$C_3$alkyl)$_2$, —C(=O)O—(H, $C_1$–$C_3$alkyl or Ar), —C(=O)CH(NH$_2$)(H, $C_1$–$C_3$alkyl or Ar), —($C_1$–$C_3$alkylene)—(=O)O—(H, $C_1$–$C_3$alkyl or Ar), —($C_1$–$C_3$alkylene)—OC(=O)—(H, $C_1$–$C_3$alkyl or Ar), —($C_1$–$C_3$alkylene)—N(independently H or $C_1$–$C_3$alkyl)$_2$, —($C_1$–$C_3$alkylene)—NHC(=O)—Ar, —($C_1$–$C_3$alkylene)—CN, —($C_1$–$C_3$alkylene)—NO$_2$, and $$-(C_1-C_3\text{alkylene})-\overset{+}{N}\diagdown\!\!\overset{}{\underset{}{\bigcirc}}\;;$$

$R^{11}$ and $R^{14}$ each have a structure selected from $$-\underset{R^{18}}{\overset{R^{17}}{\underset{|}{C}}}_{1-4}- \quad \text{and} \quad \overset{A^{10}}{\underset{}{\|}}\underset{}{\overset{}{\diagdown}}\;;$$

$R^{17}$ and $R^{18}$ are selected from H, $C_1$–$C_6$ hydrocarbyl, —CN, —$NO_2$, —NO, —C(O$C_1$–$C_3$alkyl)=NH, —N=C=O, —N=C=S, and —C(=O)O$R^{19}$ where $R^{19}$ is $C_1$–$C_6$ hydrocarbyl;

$R^{12}$, $R^{13}$ and $R^{15}$ are selected from H and protecting groups for the $A^9$ or $A^{10}$ moiety to which the $R^{12}$, $R^{13}$ or $R^{15}$ is bonded;

$A^9$ and $R^{15}$ may together form —N(CH$_2$—COOH)$_2$; and
$A^{10}$ is selected from O and S.

Alternatively, compounds of the invention may contain a ligand portion (Ligand) conjugated at a single site to one X group, where the conjugation may be through an extender arm E, as represented by the formula Ligand-E-X.

In preferred compounds of the formula Ligand-E-X, X may be any of formulas (II), (III) or (IV), $$\overset{\xi}{\underset{\xi}{\xi}}-A^9-R^{14}-A^9-R^{14}-A^9-R^{14}-A^9-R^{15} \qquad (II)$$

$$\overset{\xi}{\underset{\xi}{\xi}}-R^{14}\overset{A^9-R^{14}}{\underset{A^9-R^{14}}{\diagup\!\!\diagdown}}\overset{A^9}{\underset{R^{14}}{\diagdown\!\!\diagup}} \qquad (III)$$

$$\begin{array}{c}\text{HOOC}-CH_2\diagdown\\ \qquad\qquad\quad N-CH_2CH_2-\!\!\left(\!\!\!\overset{R^{23}}{\underset{|}{N}}CH_2CH_2\!\!\!\right)_{\!\!q}\!\!-N\!\!\diagup^{CH_2-COOH}\\ \text{HOOC}-CH_2\diagup\qquad\qquad\qquad\qquad\qquad\qquad\diagdown CH_2-COOH\end{array} \qquad (IV)$$

such that one methylene hydrogen of formula (IV) is replaced with a direct bond to E;

where, independently at each occurrence, $A^9$ is an electron-donating moiety selected from O, S, C(=O)NH and N($R^{16}$), where $R^{16}$ is selected from hydrogen and pro-drug substituents selected from $C_1$–$C_3$alkyl, —C(=O)(H, $C_1$–$C_3$alkyl or Ar), —C(=O)—($C_1$–$C_3$alkylene)—N(independently H or $C_1$–$C_3$alkyl)$_2$, —C(=O)O—(H, $C_1$–$C_3$alkyl or Ar), —C(=O)CH(NH$_2$)(H, $C_1$–$C_3$alkyl or Ar), —($C_1$–$C_3$alkylene)—C(=O)O—(H, $C_1$–$C_3$alkyl or Ar), —($C_1$–$C_3$alkylene)—OC(=O)—(H, $C_1$–$C_3$alkyl or Ar), —($C_1$–$C_3$alkylene)—N(independently H or $C_1$–$C_3$alkyl)$_2$, —($C_1$–$C_3$alkylene)—NHC(=O)—Ar, —($C_1$–$C_3$alkylene)—CN, —($C_1$–$C_3$alkylene)—NO$_2$, and

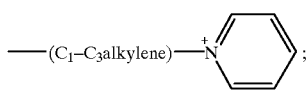

$R^{14}$ is selected from

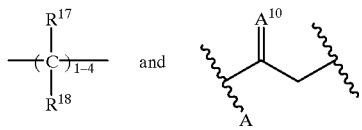

where $R^{17}$ and $R^{18}$ are selected from H, $C_1$-$C_6$hydrocarbyl, —CN, —$NO_2$, —NO, —C(O$C_1$-$C_3$alkyl)=NH, —N=C=O, —N=C=S, and —C(=O)O$R^{19}$ where $R^{19}$ is $C_1$-$C_6$hydrocarbyl;

$R^{11}$ is selected from H and protecting groups for $A^9$, where $A^9$ and $R^{15}$ may together form —N($CH_2$—COOH)$_2$;

$R^{20}$ is selected from H and $CH_2$COOH;

q is selected from 0, 1, 2 and 3; and

E represents one or more chemical bonds through which L is conjugated to X.

In preferred compounds of the formula Ligand-E-X, X has a formula selected from

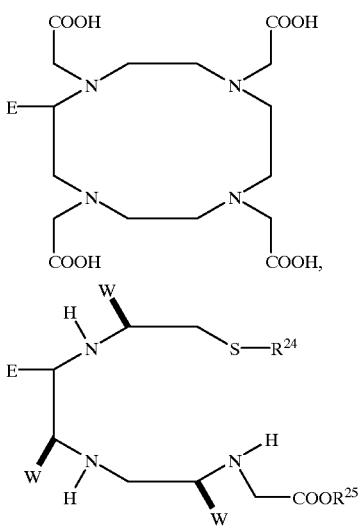

where W represents $H_2$ or =O, $R^{24}$ is selected from H, $COCH_3$, EOE, THP, COPh, acm, $C_1$-$C_6$hydrocarbyl, and sulfur protecting groups; and $R^{25}$ is selected from H and $C_1$-$C_6$hydrocarbyl; and

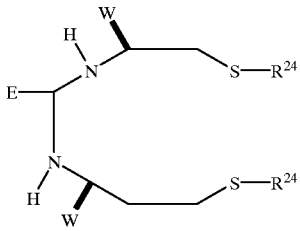

wherein $R^{24}$ is selected from H, $COCH_3$, EOE, THP, COPh, acm, $C_1$-$C_6$hydrocarbyl, and sulfur protecting groups.

Other suitable radionuclide chelating groups may be represented by the following ("$N_3$S" or "$N_2S_2$") formulae:

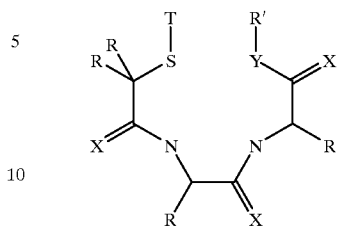

wherein:

T is H or a sulfur protecting group;

each X independently represents $H_2$ or O;

each R independently represents a substituent selected from the group consisting of hydrogen; alkyl; geminal dialkyl; a non-alkyl side chain of an amino acid other than cysteine (alkyl side chains being covered when R is an alkyl group); and —($CH_2$)$_r$—Z;

Z represents —COOH or —$NH_2$;

r is an integer of from 1 to about 4; and

R' represents the position at which the radionuclide binding group is joined, optionally through an extender arm, to the opioid ligand portion of the compound of the invention; and Y represents N or S.

The sulfur protecting group may be selected from alkyl, aryl, acyl (preferably alkanoyl or benzoyl), thioacyl groups having 1 to about 7 carbons, and organothio groups having 1 to about 10 carbons.

For the R groups, the alkyl groups generally contain from 1 to 7 carbons, preferably from 1 to 4 carbons, and most preferably represent methyl.

In another preferred embodiment, the radionuclide chelating group has the following structure:

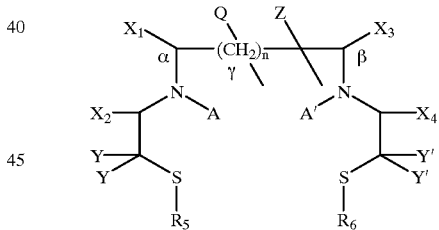

wherein:

$X_1$ and $X_2$ are H or oxo but both are not oxo;

$X_3$ and $X_4$ are H or oxo, but both are not oxo;

One of $X_1$ and $X_3$ is bonded, either directly or indirectly (through an extender arm E), to the ligand portion (L) of a compound of the invention;

A is H, alkyl group of $C_6$ or less, —$CH_2$—$CH_2$—S—$R_1$ or —CO—$CH_2$—S—$R_1$, while in a preferred embodiment, when $X_1$ or $X_2$ is =0, then A is H;

A' is H, alkyl group of $C_6$ or less, —$CH_2CH_2$—S—$R_2$ or —CO—$CH_2$—S—$R_2$, while in a preferred embodiment, when $X_3$ or $X_4$ is =0, then A' is H;

Y is (a) —$CH_2$—S—$R_3$, or H, when A is H or an alkyl group of $C_6$ or less and A' is H or an alkyl group of $C_6$ or less, or (b) H;

Y' is
(a) —$CH_2$—S—$R_4$, or H, when A is H or an alkyl group of $C_6$ or less and A' is H or an alkyl group of $C_6$ or less, while in a preferred embodiment, Y and Y' are not both H, or
(b) H;

$R_1$, $R_2$, $R_3$, $R_4$, $R_5$, and $R_6$ are independently selected from sulfur protecting groups;

Q is H or a polar group to increase the hydrophilicity of the compound;

n is 0 to 2; and

Z is —(W)$_m$—R', where W is —$CH_2$—, —$CH_2$—O—, —$CH_2CO$—, or combination thereof, m is 0 to 5, and R' is a chemically reactive group. In a preferred embodiment, when Z is attached to the carbon designated α there is either no $X_1$ or no Q at α. In another preferred embodiment, when Z is attached to the carbon designated β there is either no $X_3$ or no Q at β. In another preferred embodiment, when $X_1$ is =O there is no Z at α. In another preferred embodiment, when $X_3$ is =O there is no Z at β.

$R_1$, $R_2$, $R_3$, $R_4$, $R_5$ and $R_6$ are independently selected from sulfur protecting groups. Groups which may be used include any of the alkyl, acyl and aryl groups, disulfides and bunte salts known by those skilled in the art. Preferred groups are those that result in the formation of a thioacetal, hemithioacetal, thioester or acetamidomethyl substituent. Particularly preferred groups include p-anisylidine, acetonyl, tetrahydrylfuranyl, ethoxyethyl, tetrahydrylpyranyl, acetamidomethyl and derivatives thereof.

Preferred chelating groups of the invention include, without limitation, DOTA, $N_3S$, $N_2S_2$, $NS_3$, MAMA, DTPA and porphyrins. Preferred compound of the invention, having opioid receptor ligand (L) portions and radionuclide binding arms are shown in FIGS. 2A through 2H, where R=H, $CH_3$, or $COCH_3$; W=$H_2$ or (=O); n=0–6; X=an extender arm having 1–10 carbon atoms with 0–3 heteroatoms selected from N, S, and O; and $R^1$=H, $COCH_3$, EOE, THP, COPh, acm, Me, etc. and sulfur protecting groups known in the art.

B. Fluorochromes

Compounds of the present invention may contain a fluorochrome in addition to a ligand portion (L) having binding affinity for an opioid receptor. The fluorochrome, which may also be referred to as a fluorophore, provides the compound of the invention with diagnostic efficacy. Thus, when a compound of the invention incorporates a fluorochrome, the compound may be contacted with tissue containing opioid receptor(s) to localize the fluorochrome at the receptor site. An advantage of this method of fluorescently marking opioid receptor positive tissue over the use of fluorescently labeled anti-receptor antibody is that NID Rh (for example) recognizes only active functional receptor whereas antibodies could bind to non-functional or blocked receptor. The localized compound may then be detected by standard techniques used in the art to detect fluorochromes.

Figure 1B:
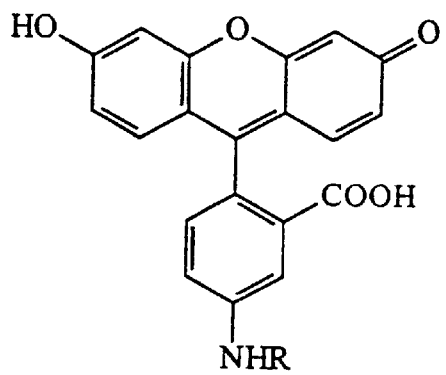
Figure 1B:
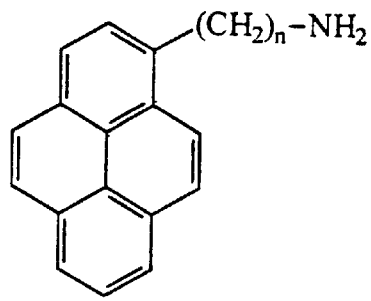
Figure 1B:
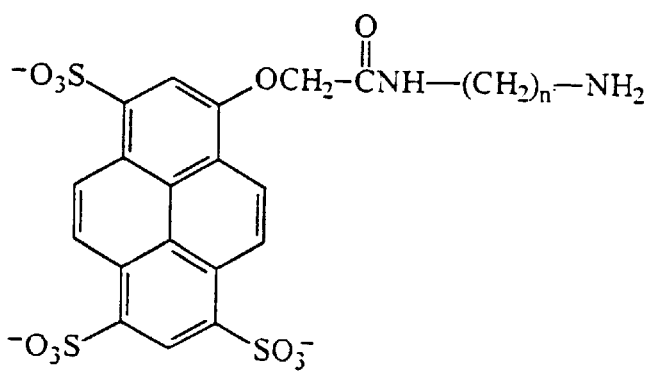
Figure 1B:
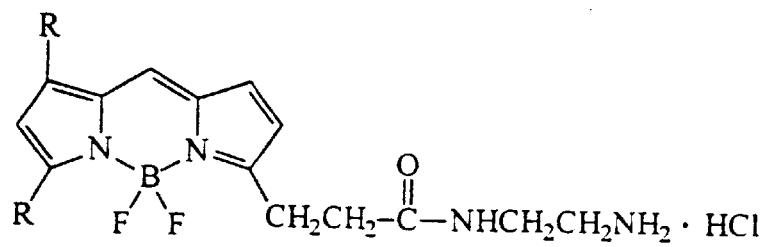
Figure 1B:
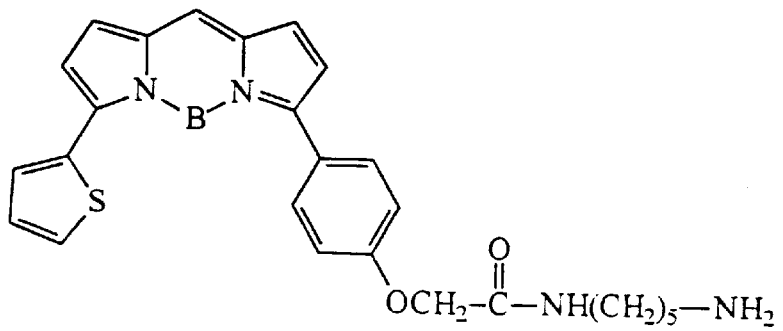
Figure 2A:
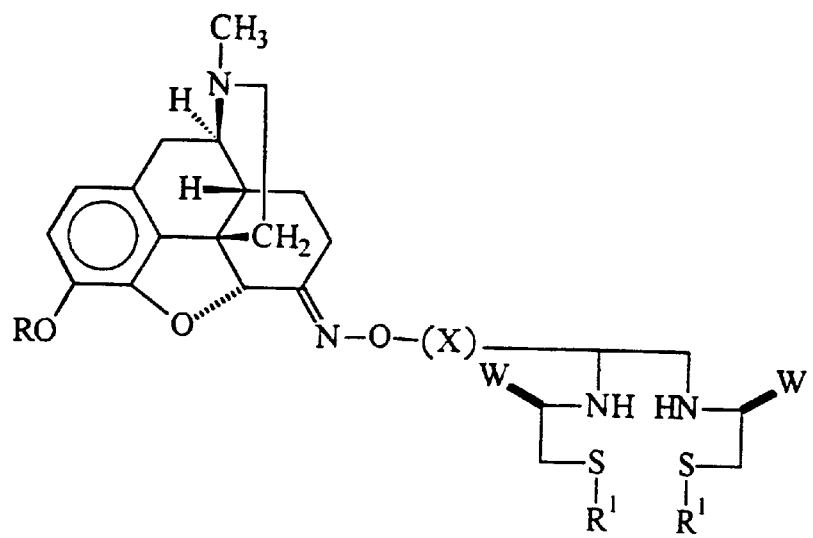
FIGS. 2A through 2H illustrate compound of the invention containing various L groups, various X groups and various extender arms E disposed therebetween.
Figure 2B:
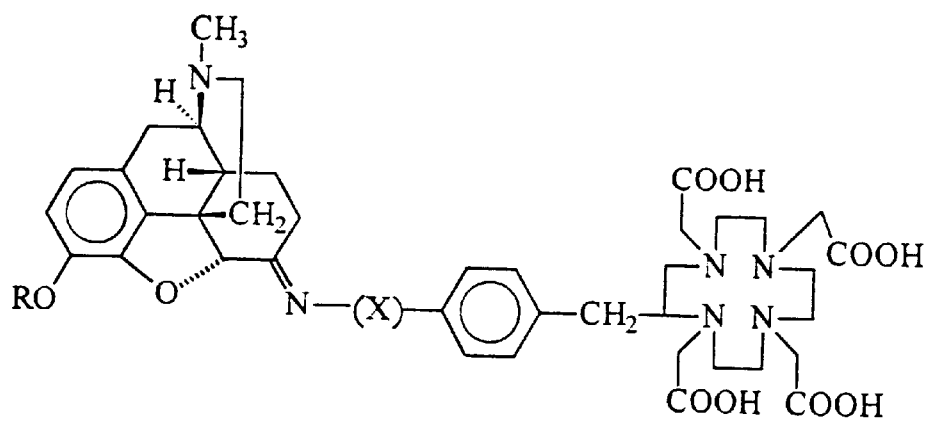
Figure 2C:
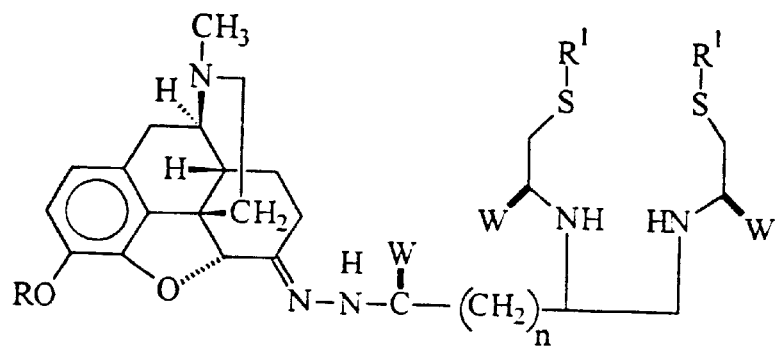
Figure 2D:
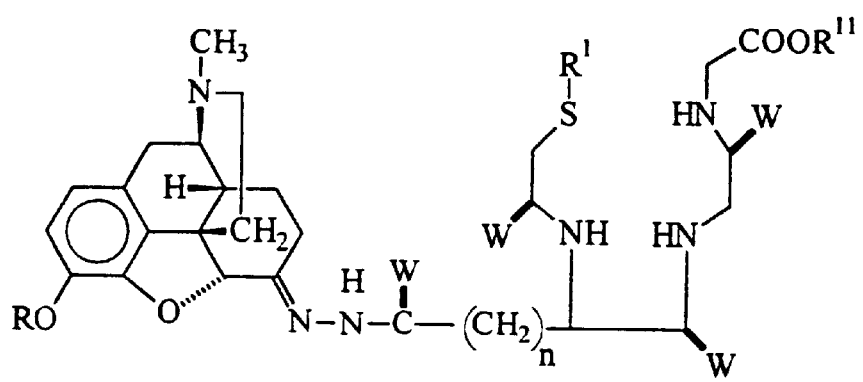
Figure 2E:
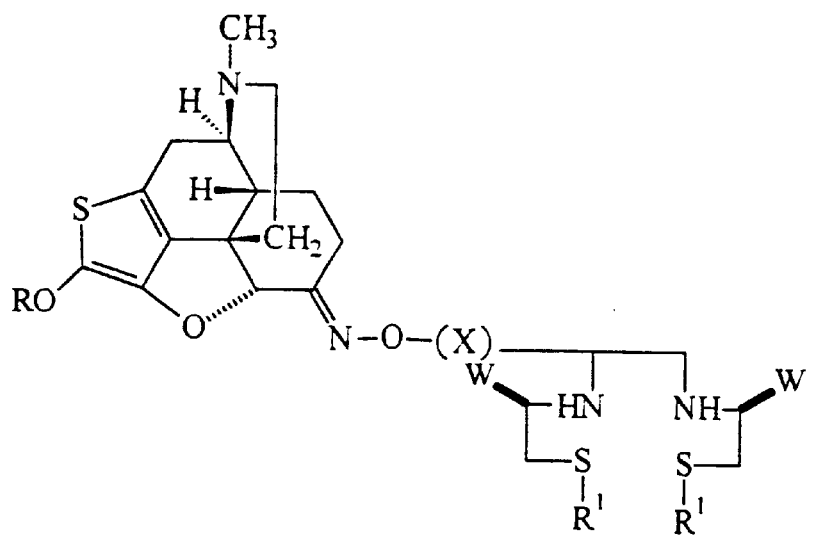
Figure 2F:
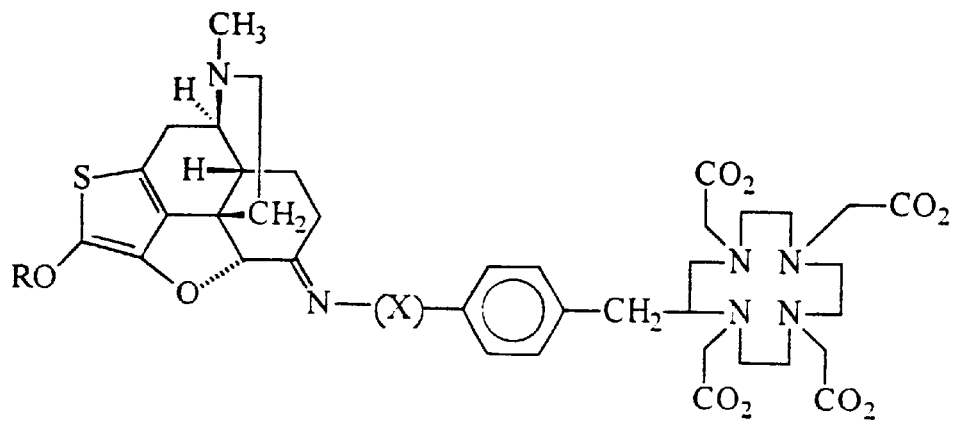
Figure 2G:
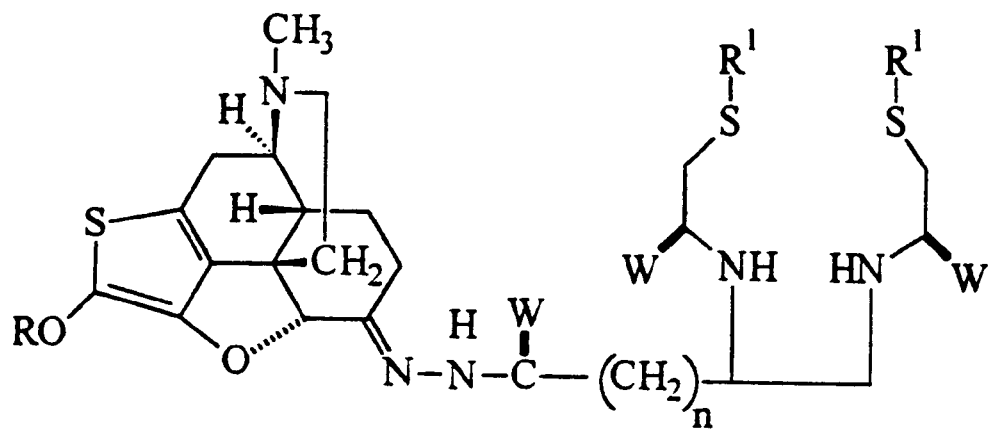
Figure 2H:
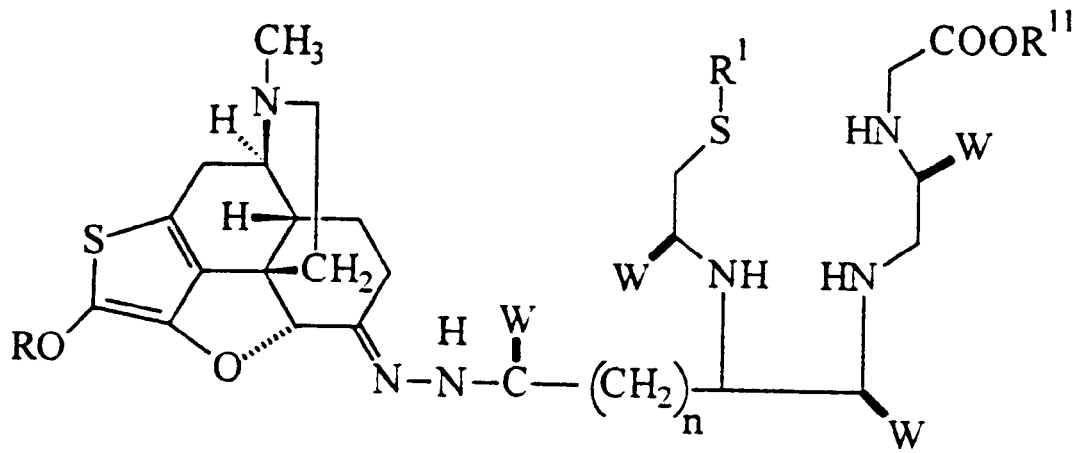

Suitable fluorochromes which may be incorporated into a compound of the invention are shown in FIGS. 1A and 1B. These fluorochromes, and many others, may be obtained from commercial sources. For instance, Molecular Probes (Corvallis Oreg.) sells many fluorochromes. A fluorochrome may be incorporated into a compound of the invention by a standard conjugation reaction. For instance, when the ligand portion of the compound contains a carboxylic acid group, any of the fluorochromes of FIGS. 1A and 1B which contain a reactive amino group, may be condensed with the ligand portion to provide an amide linkage between the two moieties. Likewise, if the ligand portion of the molecule contains an amino group, then carboxylic acid-containing fluorochromes may be condensed with the amino group to form a conjugate containing an amide group. Other methods known in the art of conjugating fluorochromes to chemical moieties may be employed.

C. Toxin

Several of the potent toxins useful within the present invention consist of an A and a B chain. The A chain is the cytotoxic portion and the B chain is the receptor-binding portion of the intact toxin molecule (holotoxin). Preferred toxins in this regard include holotoxins, such as abrin, ricin, modeccin, Pseudomonas exotoxin A, Diphtheria toxin, pertussis toxin and Shiga toxin; and A chain or "A chain-like" molecules.

D. Drug

Drugs suitable for use herein include conventional chemo-therapeutics, such as vincristine, vinblastine, doxorubicin, bleomycin, methotrexate, 5-fluorouracil, 6-thioguanine, cytarabine, cyclophosphamide and cis-platinum, as well as other conventional chemotherapeutics as described in *Cancer: Principles and Practice of Oncology*, 2d ed., V. T. DeVita, Jr., S. Hellman, S. A. Rosenberg, J.B. Lippincott Co., Philadelphia, Pa., 1985, Chapter 14. A preferred drug within the present invention is a trichothecene. Other preferred drugs suitable for use herein as a diagnostic or therapeutic active agent in the practice of the present invention include experimental drugs as described in *NCI Investigational Drugs, Pharmaceutical Data* 1987, NIH Publication No. 88-2141, Revised November 1987.

A drug may be incorporated into a compound of the invention by any suitable conjugation reaction, whereby a reactive site in the drug is reacted with a reactive site in the ligand portion of the compound. Optionally, an extender arm may be disposed intermediate the drug and the ligand portion.

E. Polyboron Moiety

The compounds of the invention may incorporate one or more boron atoms. Boron atoms are known to be activated by external neutrons to generate a therapeutically-effective species. Therefore, a compound of the invention may incorporate boron atoms, and then be administered to a subject in order that the compound associates with a particular opioid ligand. Upon such association, boron atoms are brought into proximity with the opioid receptor. The subject is then exposed to neutrons, which causes the boron atoms to be converted into a therapeutically effective species, and more specifically the $^{10}B$ atoms of the polyboron moiety are converted to an alpha particle and a $^7Li$ nucleus atom upon thermal neutron bombardment. The alpha particles are particularly effective at killing nearby cells.

For discussion of this technology, see, e.g., Ranadive et al. Nucl. Med. Biol. 20:663–668, 1993; Zamenhof et al. J. Nat'l Can. Inst. 84:1290–91, 1992; Barth et al. Cancer 70:2995–3007, 1992; Kalend et al. Med. Phys. 18:662, 1991; Barth et al. Cancer Res. 50:1061–70, 1990; Alam et al. J. Med. Chem. 32:2326–30, 1989; Perks et al. Brit. J. Radiol. 61:1115–26, 1988; Katanaka et al. Boron Neutron Capture Therapy For Tumors, pages 349–378, 1986 (Nishimura Co.); Barth et al. Hybridoma 5(1):543–554, 1986; Goldenberg et al. P.N.A.S. USA 81:560–563, 1984; Mizusawa et al. P.N.A.S. USA 79:3011–3014, 1982; Ichihashi et al. J. Invest. Dermatol. 78:215–218, 1982;

Preferably, the polyboron moiety contains several tens, and more preferably hundreds of boron atoms. As the number of boron atoms in the polyboron moiety is increased, the opportunity for thermal neutrons to impact a $^{10}$B atom, and the opportunity for an impacted $^{10}$B atom to emit a lethal alpha particle, increases. Thus, the polyboron moiety is preferably a boron-containing polymer. Suitable boron-containing materials which may function as therapeutically effective chemical agents suitable for binding to an opioid receptor ligand according to the present invention are disclosed in the aforecited references.

F. Protein

As used herein, includes proteins include polypeptides and peptides, and may be an intact molecule, a fragment thereof, or multimers or aggregates of intact molecules and/or fragments; and may occur in nature or be produced, e.g., by synthesis (including chemical and/or enzymatic) or genetic engineering. Suitable examples of protein include, without limitation, horseradish peroxidase, green fluorescent protein and streptavidin.

G. A Chemical Moiety Capable of Binding to Other Molecules of Interest

The "X" group of a compound of the present invention may be a chemical moiety that is capable of binding to other molecules of interest. One suitable example of a compound of the invention having a chemical moiety capable of binding to a molecule of interest is shown below, where the chemical moiety is capable of reacting with any primary or secondary amine-containing compound:

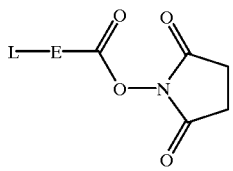

The "X" group which is a chemical moiety capable of binding to other molecules of interest may be one member of a complementary/anti-complementary set of molecules that demonstrate specific binding, generally of relatively high affinity. Exemplary complementary/anti-complementary pairs include zinc finger protein/dsDNA fragment, enzyme/inhibitor, hapten/antibody, lectin/carbohydrate, ligand/receptor, and biotin/avidin or streptavidin. As used herein, the antibody present in a binding pair may be an antibody fragment, preferably an antigen-binding antibody fragment.

Biotin/avidin or streptavidin is a preferred complementary/anti-complementayry pair. Thus, a preferred compound of the present invention may include either biotin (which binds to either avidin or streptavidin) or avidin (which binds to biotin) or streptavidin (which also binds to biotin).

H. A Therapeutically or Diagnostically Effective Radioisotope

The compound of the invention may incorporate a therapeutically or diagnostically effective radioisotope. In one embodiment, the compound of the invention contains radionuclide binding arms, which can chelate with a therapeutically or diagnostically effective radioisotope. This embodiment of the invention is described else-where. However, in another embodiment, the radioisotope is covalently incorporated into a compound of the invention. Diagnostically-effective radioisotopes include gamma-emitters such as indium ($^{111}$In) and technectium ($^{99m}$Tc), and positron emitters such as carbon 11. Preferably, the radioisotope is a gamma-emitter rather than a positron emitter.

For therapeutic purposes, the radioisotope may be a beta-emitter, such as $^{90}$Y, $^{186}$Re, and 188Re, among others. Preferably, the beta-emitter is not tritium because tritium is not a high energy beta emitter, and thus tritium is not effective in therapeutic methods according to the present invention. The therapeutic radioisotope may be an alpha-emitter, such as Pb, Bi and At. Each of these radioisotopes may be introduced into a compound of the present invention using the "PIP" chemistry described herein.

I. Pretargeting

In a preferred embodiment of the invention, a compound of the present invention is used in pretargeting methods. Essentially, such pretargeting methods are characterized by an improved targeting ratio or increased absolute dose to the target cell sites in comparison to conventional cancer diagnosis or therapy. A general description of pretargeting methods may be found in U.S. Pat. Nos. 4,863,713, 5,578,287, and 5,630,996. Moreover, typical pretargeting approaches are summarized below.

Pretargeting methods are of two general types: three-step pretargeting methods and two-step pretargeting methods.

The three-step pretargeting protocol features administration of an targeting moiety-ligand conjugate, which is allowed to localize at a target site and to dilute in the circulation. This is followed by administration of an anti-ligand which binds to the targeting moiety-ligand conjugate and clears unbound targeting moiety-ligand conjugate from the blood, as well as binds to targeting moiety-ligand conjugate at the target site. The complementary/anti-complementary set of molecules discussed above may function as the ligand/anti-ligand pair in the pretargeting method. Thus, the anti-ligand fulfills a dual function by clearing targeting moiety-ligand conjugate not bound to the target site as well as attaches to the target site to form a targeting moiety-ligand:anti-ligand complex. Finally, a diagnostic or therapeutic active agent-ligand conjugate that exhibits rapid whole body clearance is administered.

When the active agent-ligand conjugate in circulation comes into close proximity to the targeting moiety-ligand:anti-ligand complex bound to the target site, the anti-ligand portion of the complex binds to the ligand portion of the circulating active agent-ligand conjugate, thus producing a targeting moiety-ligand:anti-ligand ligand-active agent "sandwich" at the target site. Furthermore, because the unbound diagnostic or therapeutic active agent is attached to a rapidly clearing ligand (rather than a slowly clearing targeting moiety, such as antibody, antibody fragment), this technique provides decreased non-target exposure to the active agent.

Alternatively, the two-step pretargeting methods eliminate the step of administering the above identified anti-ligand. These "two-step" procedures feature targeting moiety-ligand or targeting moiety-anti-ligand administration, followed by the administration of active agent conjugated to the opposite member of the ligand/anti-ligand pair.

As an optional step in the two-step pretargeting methods of the present invention, ligand or anti-ligand, designed specifically to provide a clearance function, is administered to facilitate the clearance of circulating targeting moiety-ligand or targeting moiety-anti-ligand. Thus, in the two-step pretargeting approach, the clearing agent does not become bound to the target cell population, either directly or through the previously administered target cell bound targeting moiety-anti-ligand or targeting moiety-ligand conjugate.

A targeting moiety in the pretargeting methods of the present invention has the functional property that it binds to a defined target cell population, such as tumor cells that contain opioid receptors. Thus, a ligand portion (L) of compounds of the present invention provide the needed targeting moiety in the pretargeting approach.

Ligand/Anti-ligand pairs suitable for use in the present invention include biotin/avidin or streptavidin, haptens and epitopes/antibody, fragments or analogs thereof, including mimetics, lectins/carbohydrates, zinc finger proteins/dsDNA fragments, enzyme inhibitors/enzymes; and analogs and derivatives thereof. Preferred ligands and anti-ligands bind to each other with an affinity of at least about $K_A \geq 10^9 M^{-1}$ or $K_D \leq 10^{-9} M$. Biotin/avidin or streptavidin is a preferred ligand/anti-ligand pair.

In general such pretargeting methods will preferably include the administration of a anti-ligand that provides a clearance function. The clearance is probably attributable to cross-linking and/or aggregation of conjugates that are circulating in the blood, which leads to complex/aggregate clearance by the recipient's RES (reticuloendothelial system). In one embodiment of the present invention, the anti-ligand clearance of this type is preferably accomplished with a multivalent molecule. However, a univalent molecule of sufficient size to be cleared by the RES on its own could also be employed.

J. PIP Labeling

"PIP" literally stands for p-iodophenyl, and more specifically refers to a labeling technique that employs a reagent having the partial formula shown below, which may more precisely be called a p-iodobenzyl group:

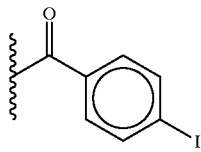

PIP labeling may be used to add a radioisotope (denoted "*X") to an aromatic or heteroaromatic ring (collectively "Ar") in compounds of the invention. The radioisotope may be an isotope of iodine, bromine, fluorine, or astatine. The aromatic ring may contain one or more substituents (denoted "R"), which preferably do not activate Ar toward electrophilic substitution on the order produced by hydroxy or amino substitution of the ring, wherein said bond or said substituent has attached thereto a functional group suitable for conjugation.

As utilized herein, the symbol *X indicates any radioisotope of: iodine, particularly I-123, I-125, and I-131; bromine, particularly Br-75, Br-76 and Br-77; fluorine, particularly F-18; and, astatine, particularly At-211. Preferred radiohalogens *X for diagnostic imaging purposes include I-131 and most preferably I-123 for imaging with gamma cameras; and for positron tomographic imaging. F-18, Br-75, and Br-76. For clinical radiotherapy, preferred radiohalogens *X include I-131, Br-77, and At-211. Preferred radiohalogens *X for in vitro radioimmunoassay purposes include I-125, and I-131. Pursuant to this invention the radiohalogen *X is preferably para- or meta-positioned on ring Ar relative to substituent R in order to render the radiohalogen less susceptible to catabolism by dehalogenase enzymes.

The symbol Ar indicates any aromatic or heteroaromatic ring. Preferred rings Ar include benzene, pyridine, furan, and thiophene, the latter three because of the enhanced water solubility they convey. The attachment of the radiohalogen to a carbon atom in an aromatic ring is preferred over attachment to an alkyl carbon atom due to the increased bond strength of the carbon-halogen bond in the aromatic ring. The nature of the aromatic ring is not critical and may be mono-, bi-, tri-, or higher number of rings, but the monocyclic ring is preferred based on increased water solubility. The aromatic rings may consist of all carbon atoms or may contain heteroatoms such as nitrogen, oxygen, or sulfur. Inclusion of heteroaromatic rings such as pyridines, furans, or thiophenes can assist in increasing water solubilities of the radioiodinated small molecule conjugates. The presence of the a heteroaromatic ring also aids in elimination of water soluble metabolites via sulfoxide and sulfone formation in the case of thiophene ring system, thereby decreasing toxicity to the host. Further substitution on the aromatic ring, exclusive of *X and R, with polar substituents such as a nitro, sulfonic acid, carboxylic acid, or dialkyl amino group can also be used to enhance water solubility. Increased water solubility is desirable to give higher yields and less potential aggregation in the conjugation reaction with targeting agent and to cause less perturbation of the lipophilicity of the compound of the invention. Other substituents can be added to impart some control against enzymatic degradation.

The symbol R indicate any substituent that meets the following three requirements: First, the R substituent must not highly activate ring Ar toward electrophilic substitution. In other words, R cannot be linked to an Ar by a linkage that increases the electron density of Ar on the order of the increase produced by a hydroxy or amino substitution. Second, R should be a short-chain substituent so that unconjugated or cleaved radiohalogenated molecules can be rapidly removed by the kidneys. Thus, R may contain an alkyl or other spacer chain between the aryl linkage and the functional group for targeting agent conjugation, but such a spacer chain should preferably contain no more than 5, and most preferably no more than 3, straight-chain carbon atoms. Third, the R substituent should bear a functional group that is available for conjugation to the ligand portion (L) of a compound of the invention, under conjugation conditions, such as acylation or amidation, that preserve the biological activity of the opioid receptor ligand. Thus, R should provide a functional group, such as imide ester or imidate ester, for covalent attachment of corresponding functional groups (or conjugated attachment sites) of targeting agents, or carrier molecule such as amino acid polymers that can in turn be conjugated to targeting agent molecule.

Suitable functional groups for the above-stated purpose include phenolic esters (e.g., para-nitrophenol), imide esters (e.g., succinimide ester), imidate esters, anhydrides, acylsuccinimides, aldehydes, isothiocyanates, diazo, amines, hydrazines, alkyl halides, maleimides, and other groups that can be used to attach the molecule to a targeting agent through a covalent bond.

Representative R substituents include alkyl acids, amido alkyl acid, nitrile, alkyl nitrile, amido alkyl nitrile, imide ester, alkyl imide esters, amido alkyl imide ester, imidate ester, alkyl imidate esters, and amido alkyl imidate ester.

Illustrative but nonlimiting example of radiohalogenated small molecules of this invention include: N-succinimidyl-3-(4-[$^{131}$]iodophenyl)propionate; methyl-3-(4-[$^{131}$]iodophenyl)-propioimidate; N-succinimidyl-4-[$^{131}$]iodobenzoate; methyl-4-[131]iodobenzimidate; N-succinimidyl-4-[$^{131}$]iodobenzamido-acetate or N-succinimidyl-4-[$^{131}$]iodohippurate; methyl-4-[$^{131}$]iodobenzemiodoacetimidate; and 4-[$^{131}$]iodobenzamidoacetonitale. The synthesis of radiohalogenated small molecules such as these is described in European Patent Application 0 203 764 published Dec. 3, 1986. The radiolabeling procedures described therein generally involve substituting an organometallic group which is a tri-alkyl stannane of the formula $Sn(R)_3$ wherein R is a lower alkyl group, preferably $Sn(n-Bu)_3$ or $SnMe_3$, on a haloaromatic compound. A radioisotope of a halogen then is substituted for the organometallic group by halodemetalization. In addition, the following U.S. Patents, which generally disclose methods for radiohalogenation of small molecules for protein labeling, are incorporated herein by reference: U.S. Pat. Nos. 4,885,153; 5,045,303; 5,213,787; and 5,609,848.

Sulfur Protecting Groups

The compounds of the invention may contain one or more protecting groups for one or more atoms. Suitable protecting groups are set forth in Greene, "Protective Groups in Organic Chemistry", John Wiley & Sons, New York N.Y. (1991).

Sulfur atoms, particularly when present as part of a radionuclide binding group, may be protected in compounds of the present invention. In one embodiment of the invention, the sulfur protecting group, when taken together with the sulfur atom to be protected, is a hemithioacetal group. Suitable hemithioacetals include, but are not limited to, those having the following formulae.

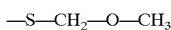

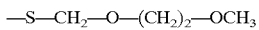

and

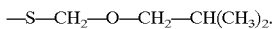

Preferred hemithioacetals generally are of the following formula, wherein the sulfur atom is the sulfur atom of the chelating portion of the compound of the invention.

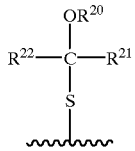

wherein $R^{20}$ is a lower alkyl group, preferably of from 2 to 5 carbon atoms, and $R^{22}$ is H or a lower alkyl group, preferably of from 1 to 3 carbon atoms. Alternatively, $R^{20}$ and $R^{22}$ may be taken together with the carbon atom and the oxygen atom shown in the formula to define a nonaromatic ring, preferably comprising from 3 to 7 carbon atoms in addition to the carbon and oxygen atoms shown in the formula. $R^{21}$ represents hydrogen or a lower alkyl group wherein the alkyl group preferably is of from 1 to 3 carbon atoms.

Examples of such preferred hemithioacetals include, but are not limited to:

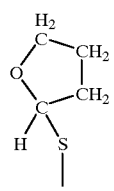 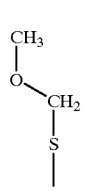

Tetrahydrofuranyl   Methoxymethyl (MOM)

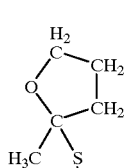 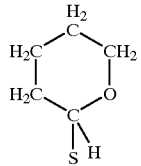

2-Methyl tetrahydrofuranyl   Tetrahydropyranyl (THP)

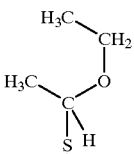 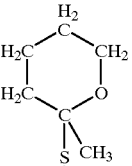

Ethoxyethyl (EOE)   2-Methyl tetrahydropyranyl

Advantages of using hemithioacetal sulfur protecting groups include the fact that a separate step for removal of the sulfur-protective groups is not necessary. The protecting groups are displaced from the compounds of the invention during the radiolabeling step, in what is believed to be metal-assisted acid cleavage; i.e., the protective groups are displaced in the presence of the radionuclide at an acidic pH, and the radionuclide is bound by the opioid receptor ligand of the invention. The radiolabeling procedure thus is simplified, which is especially advantageous when the compounds of the invention are to be radiolabeled in a hospital laboratory shortly before use.

In addition, the basic pH conditions and harsh conditions associated with certain known radiolabeling procedures, or procedures for removal of other sulfur protective groups, are avoided. Because basic and/or harsh conditions are avoided, the compounds of the invention may incorporate (at sites other than are desirably deprotected) protecting groups and other chemical functionality which should desirably survive the radiolabeling step, but which would decompose under basic and/or harsh conditions. Such base labile groups include any group which may be destroyed, hydrolyzed, or otherwise adversely affected by exposure to basic pH. Certain protein conjugation groups, including activated esters, isothiocyanates, maleimides, and other Michael acceptors, among others, are relatively base labile. Thus, these group may be incorporated into compounds of the invention, and will retain their integrity throughout the radiolabeling procedure of the present invention.

Other preferred sulfur atom protecting groups including ACM and i-PrCO, as defined below:

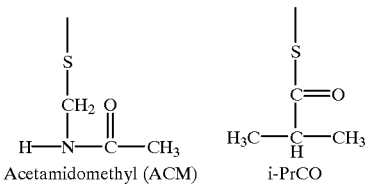

Acetamidomethyl (ACM)   i-PrCO

The acetamidomethyl group may be displaced from a compound of the invention during radiolabeling conducted at about 50° C. in a reaction mixture having a pH of about 3 to 6. The use of an acetamidomethyl group generally improves the water solubility of the compound of the invention, which is desirable in therapeutic and diagnostic applications involving water-based living organisms.

Extender Arms

E is a group that functions as an "extender arm" and may be useful to distance the opioid binding site (L) from the therapeutically or diagnostically effective X group of the compound of the invention. Extender arms of the invention covalently link an X group to an L portion through a chain of 2–60 atoms selected from carbon, oxygen, nitrogen and sulfur. The chain is "stable" in that it can exist at room temperature without spontaneously decomposing to constituent atoms or molecular fragments. However, in one embodiment of the invention, the chains are stable in terms of their thermodynamic stability, yet are unstable in that they are metabolically degraded and cleaved by, for example, an enzyme. Thus, the extender arm may include selectively cleaveable linkers such as carboxylate esters, acetate esters, imidate esters and carbamates, among others. Other groups which may be used include methylene (—$CH_2$—), methyleneoxy (—$CH_2O$—), methylenecarbonyl (—$CH_2$—CO—), or combinations thereof. The number, m, of groups such as these would be typically 0 to 30 and preferably 0 to 5. Polyamides, as formed from, for example, condensation of amino acids, are a preferred extender arm.

Extender arms may incorporate side chains, e.g., amino acid residue side chains, which can impart desirable properties to the molecule such as enhanced receptor binding affinity, increased hydrophobicity, or improved pharmacokinetics to allow enhanced vocalization.

Synthesis of Opioid Receptor Ligands with X Groups

Compounds of the invention are conveniently prepared by the chemical coupling of L portion of the molecule to an X group. An extender arm E may be disposed between the L and X portions of the molecule. To prepare molecules of the formula L-E-X, a ligand molecule and an E-X group may be separately synthesized, and then the two groups joined together. Alternatively, the ligand molecule may be synthesized with an extender arm, i.e., L-E, and the X group may be separately synthesized, before combining the two groups together to form L-E-X. The Examples set forth at the end of this specification illustrate various synthetic approaches to compounds of the invention.

Metal Species

The compounds of the invention described above having radionuclide chelating groups may be chelated with one or more metals or metal ions, which are collectively referred to herein as "metal species", to provide useful therapeutic and diagnostic agents. For in vitro diagnostic purposes, fluorescent metal species such as Terbium and Europium may be preferred since their complexes would be chemically similar to In and Y complexes but would be detectable by their fluorescence. Representative references in this regard include Min Li and Paul R. Selvin, "Amino Reactive Forms of a Luminescent Diethylenetriaminepentaacetic Acid Chelate of Terbium and Europium: Attachment to DNA and Energy Transfer Measurements," *Bioconj. Chem.* 8:127–132 (1997); and Harri Takalo et al., "Synthesis of Europium (III) Chelates Suitable for Labeling of Bioactive Molecules," *Bioconj. Chem.* 5:278–282 (1994).

For diagnostic purposes, preferred metal species which may be chelated according to the invention include gamma emitter isotopes which are useful for diagnostic scintigraphy. Such gamma emitters include, without limitation, $gallium^{67}$, $gallium^{68}$, $indium^{111}$, and $technetium^{99m}$ ($^{99m}Tc$). $Indium^{111}$ with a half-life of 2.8 days, and $technetium^{99m}$ with a half-life of 6 hrs, are particularly useful gamma emitters.

For therapeutic purposes, the compounds according to the invention may be chelated to beta radiation emitters which are useful as cytotoxic agents for radiotherapy. Such emitters include, without limitation, isotopes such as $scandium^{46}$, $scandium^{47}$, $scandium\ ^{48}$, $copper^{64}$ ($^{64}Cu$), $copper^{67}$ ($^{67}Cu$), $gallium^{72}$, $gallium^{73}$, $yttrium^{90}$ ($^{90}Y$), $ruthenium^{97}$ ($^{97}Ru$), $palladium^{100}$, $rhodium^{101m}$, $rhodium^{105}$ ($^{105}Rh$), $palladium^{109}$ ($^{109}Pd$), $samarium^{153}$, $rhenium^{186}$ ($^{186}Re$), $rhenium^{188}$ (188 Re), $rhenium^{189}$, $gold^{198}$($^{198}Au$), $gold^{199}$ ($^{199}Au$), $radium^{212}$, $lead^{203}$ ($^{203}Pb$), and $lead^{212}$ ($^{212}Pb$). Of these, $^{186}Re$, $^{188}Re$, and $^{90}Y$ are preferred.

The compounds of the invention may also be used to chelate alpha radiation emitting materials such as $bismuth^{212}$ ($^{212}Bi$), positron emitters such as $zirconium^{89}$, fluorescent members of the lanthanide series of elements such as terbium and europium and of the transition series such as ruthenium, and paramagnetic materials such as gadolinium and iron. In addition the compounds of the invention are also suitable for binding numerous other metal ions which may be useful for a variety of purposes, including those in which a catalytic property of the metal ion is of utility. Iron, copper, vanadium, rhodium, platinum, palladium and titanium are examples of metal ions useful in catalyzing a variety of organic reactions, such as the cleavage of nucleic acids by the iron-catalyzed generation of hydroxyl free radicals.

Preferred radionuclides for use in conjunction with a diagnostic kit are $^{99m}Tc$, $^{97}Ru$ $^{111}In$ and $^{203}Pb$ and with a therapeutic kit are $^{186}Re$, $^{188}Re$, $^{90}Y$, $^{67}Cu$, $^{105}Rh$, $^{198}Au$, $^{99}Au$ and $^{212}Bi$.

Methods for preparing these isotopes are known. For example, molybdenum/technetium generators for producing $^{99m}Tc$ are commercially available. In addition, tungsten/rhenium generators for producing $^{188}Re$ are available. Procedures for producing $^{186}Re$ include the procedures described by Deutsch et al., (*Nucl. Med. Biol.* Vol. 13:4:467–477, 1986) and Vanderheyden et al. (*Inorganic Chem.* Vol. 24:1666–1673, 1985), and methods for production of $^{188}Re$ have been described by Blachot et al. (*Int'l J. of Applied Radiation and Isotopes* Vol. 20:467–470, 1969) and by Klofutar et al. (*J. of Radioanalytical Chem.* Vol. 5:3–10, 1970). Production of $^{109}Pd$ is described in Fawwaz et al. (*J. Nucl. Med.* 25:796, 1984). Production of $^{212}Pb$ and $^{212}Bi$ is described in Gansow et al. (*Amer. Chem. Soc. Symp. Ser.* 241:215–217, 1984), and Kozah et al. (*Proc. Nat'l Acad. Sci USA* 83:474–478, 1986).

Compounds of the Invention Chelated with Radionuclides

The present invention provides compounds having affinity to one or more opioid receptors, where the compounds also have radionuclide binding group for chelation with a radionuclide. The chemical structure of such chelates, which are also referred to herein as radiolabeled compounds, is essentially the same as that of a compound of the invention with the exception that a metal is shown complexing with four or more electron-donating atoms (i.e., S, O or N) of the binding groups (also referred to as binding arms).

In one embodiment of the invention, a compound of the invention is chelated to a radionuclide so as to include the following structure, where any of the "R" groups may be joined, directly or indirectly, to a ligand portion (L) of the compound of the invention.

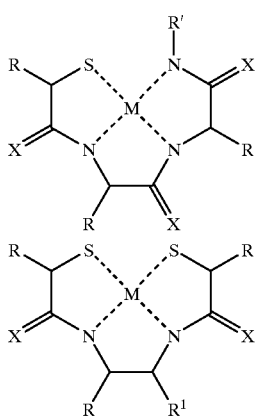

In the above structure, M is a radionuclide ion, to which 1 or 2 oxygen atoms may be bonded (to provide monooxo and dioxo species), or 1 nitrogen atom may be bonded (to provide a nitrido species) especially if the metal is Tc or Re. The radioisotopes $^{99m}$Tc and $^{186}$Re/$^{188}$Re are commercially available as pertechnetate (TcO$_4^-$) and perrhenate (ReO$_4^-$) which are in their most stable +7 oxidation state. In order for the donor atoms of the binding arms to coordinate with Tc and Re, the pertechnetate and perrhenate have to be reduced to lower oxidation states with reducing agents such as stannous chloride (SnCl$_2$). The donor atom of the binding arms in compounds of the invention may utilize Tc and Re in their +5 oxidation state.

A variety of metal ions or complex ions may be employed as the radionuclide. These metals include, but are not limited to, copper, e.g., $^{64}$Cu and $^{67}$Cu; technetium, e.g., $^{99m}$Tc; rhenium, e.g., $^{186}$Re and $^{188}$Re; lead, e.g., $^{203}$Pb and $^{212}$Pb; palladium, e.g, $^{109}$Pd; bismuth, e.g., $^{212}$Bi, and gold, e.g., $^{198}$Au. The metal may be present as an ion, e.g., $^{64}$Cu$^{2+}$ and $^{67}$Cu$^{2+}$ (copper may end up in S-containing ligands as Cu$^+$) or as an oxidized form, e.g., $^{99m}$TcO$_3^+$, $^{186}$ReO$_3^+$ or $^{188}$ReO$_3^+$ when incorporated in the chelate compounds.

The dashed lines in the formula presented for the chelate compounds of the invention represent four coordinate covalent bonds, between the metal radionuclide M and the sulfur and the three nitrogen atoms (an N$_3$S chelator) shown in the formula on the left, and between the radionuclide M and the two sulfur and two nitrogen atoms (an N$_2$S$_2$ chelator) shown in the formula on the right. In either case, the metal radionuclide is bound through relatively stable bonds in the chelated compounds of the invention. Also in the above formulas, =X represents a carbonyl group or two hydrogen atoms. R and R$^1$/R' are organic groups.

Synthesis of Opioid Recepetor Ligands/Binding Arms Chelated with Radionuclides

The compounds of the present invention may be radiolabeled, using conventional procedures, with any of a variety of radionuclide metals to form the corresponding radionuclide metal chelates. As set forth above, these radionuclide metals include, but are not limited to, copper (e.g., $^{67}$Cu and $^{64}$Cu); yttrium ($^{90}$Y), technetium (e.g., $^{99m}$Tc); palladium (e.g., $^{109}$Pd), indium (e.g., $^{111}$In), rhenium (e.g., $^{186}$Re and $^{188}$Re); lead (e.g. $^{212}$Pb); and bismuth (e.g., $^{212}$Bi). The selection of suitable chemistry to achieve chelation between a binding arm in a compound of the invention and a radionuclide will depend, for example, on the identity of the radionuclide and the presence or absence of protecting groups bound to the atoms which undergo the chelation with the radionuclide. Many aspects of the chemistry of chelation have been described in the prior art, see, e.g., U.S. Pat. Nos. 5,227,474; 5,164,176; 5,120,526; 5,112,953; 5,091,514; 5,075,099; 4,988,496; 4,965,392; and 4,963,688, as well as references cited therein.

In one embodiment of the present invention, compounds of the invention comprising acetamidomethyl and/or hemithioacetal sulfur protective groups are radiolabeled with a metal radionuclide by reacting the compound with the radionuclide under conditions of acidic pH. It is believed that the acidic pH and the presence of the metal both contribute to the displacement of the sulfur protective groups from the chelating compound. The radionuclide is in chelatable form when reacted with the compound of the invention.

In the case of technetium and rhenium, being in "chelatable form" generally requires a reducing step. A reducing agent will be employed to reduce the radionuclides (e.g., in the form of pertechnetate and perrhenate, respectively) to a lower oxidation state at which chelation will occur. Many suitable reducing agents, and the use thereof, are known, see, e.g., U.S. Pat. Nos. 4,440,738; 4,434,151; and 4,652, 440. Such reducing agents include, but are not limited to, stannous ion (e.g., in the form of stannous salts such as stannous chloride or stannous fluoride), metallic tin, ferrous ion (e.g., in the form of ferrous salts such as ferrous chloride, ferrous sulfate, or ferrous ascorbate) and many others. Sodium pertechnetate (i.e., $^{99m}$TcO$_4^-$ which is in the +7 oxidation level) or sodium perrhenate (i.e., $^{188}$ReO$_4^-$, $^{186}$ReO$_4^-$) may be combined simultaneously with a reducing agent and a chelating compound of the invention in accordance with the radiolabeling method of the invention, to form a chelate.

In one preferred embodiment, the radionuclide is treated with a reducing agent and a complexing agent to form an intermediate complex (i.e., an "exchange complex"). This embodiment is preferred when Tc or Re are the radionuclide. Complexing agents are compounds which bind the radionuclide more weakly than do the compounds of the invention, and may be weak chelators. Any of the suitable known complexing agents may be used, including but not limited to gluconic acid, glucoheptonic acid, tartaric acid, methylene disphosphonate, glyceric acid, glycolic acid, mannitol, oxalic acid, malonic acid, succinic acid, bicine, N,N'-bis(2-hydroxy ethyl) ethylene diamine, citric acid, ascorbic acid and gentisic acid. Tartaric acids gluconic acid or glucoheptonic acid are preferred as the Tc-complexing agent and citric acid for rhenium.

When the radionuclide in the form of an exchange complex is reacted with a compound having radionuclide binding arms according to the present invention, the radionuclide will transfer to the compound which binds the radionuclide more strongly to form chelates of the invention. Heating may be required to promote transfer of the radionuclide. Radionuclides in the form of such exchange complexes also are considered to be in "chelatable form" for the purposes of the present invention.

Chelates of $^{212}$Pb, $^{212}$Bi, and $^{109}$Pd may be prepared by combining the appropriate salt of the radionuclide with a suitable compound of the invention at an appropriate pH, and incubating the reaction mixture at room temperature or at higher temperatures. It is not necessary to treat the lead, bismuth, palladium, and copper radioisotopes with a reducing agent prior to chelation, as such isotopes are already in an oxidation state suitable for chelation (i e., in chelatable form). The specific radiolabeling reaction conditions may vary somewhat according to the particular radionuclide and chelating compound involved.

The rhenium chelate may be formed from various routes. For example, reducing perrhenate to rhenium (IV) hexachloride by employing hypophosphorous acid and concentrated HCl at 95° C. yields rhenium hexachloride. The rhenium hexachloride may then be converted to rhenium dioxo diethylenediamine chloride in 90% ethylenediamine at room temperature. At a basic pH in the presence of a compound of the invention having radionuclide binding arms, the rhenium dioxo diethylenediamine chloride exchanges rapidly with, for example, a binding arm having the $N_3S$ configuration of chelating atoms.

$^{99m}$Tc-radiolabeling of compound of the invention having radionuclide binding arms with N and/or S atoms in the binding arms may be accompanied by the following Methods A or B.

Method A: Stannous gluconate kits are prepared containing 5.0 mg sodium gluconate, 0.1 mg stannous chloride, 0.1–1.0 mg of an opioid receptor ligand of the invention with N,S-binding arms, and 1.0–5.0 mg of lactose. The pH of the solution is maintained between 5 and 7.5 using hydrochloric acid, acetic acid or sodium hydroxide. To the stannous gluconate kit is added 1.0 mL sodium pertechnetate ($Na^+$ $_{99m}TcO_4^-$) in saline with a specific activity of 35–50 mCi/mL. The vial is thoroughly mixed and incubated at 25° C.–100° C. for 15–30 minutes. The percent formation of $^{99m}$Tc-chelate is determined by ITLC and HPLC using a radiometric detection system.

Method B: Stannous tartrate kits are prepared in an evacuator vial under nitrogen to contain 0.5 mL of disodium tartrate (10 mg/mL) and 0.1 mL stannous chloride (1.0 mg/mL in ethanol). The pH of the solution is kept between 5 and 7.5 preferably 6.5. To this stannous tartrate solution is added 1.0 mL of sodium pertechnetate at a specific concentration of 35–50 mCi/mL in saline. The reaction mixture is allowed to stand at room temperature. In another evacuated vial, 200 $\mu$L of sodium phosphate (0.5 M, pH 8.0 or 10.0) and 1.0 mL of $N_4$ opioid receptor ligand (1.0 mg/mL) are added successively. Then Tc-99m-Tartrate (50 mCi) is added, and the vial is incubated at 25° C.–100° C. for 10–30 min. The percent formation of radiolabeled $N_4$-opioid receptor ligand is determined by ITLC and HPLC using a radiometric detection system.

The following general method may be used to radiolabel opioid receptor ligands with radionuclide binding arms having protected sulfur atoms in their binding arms with $^{186}$Re: a solution of 11.0 mg of citric acid 370 $\mu$g of gentisic acid and 460 $\mu$g of stannous chloride dihydrate in 100 $\mu$L $H_2O$ is adjusted to a final pH of 2. To this solution, 500 $\mu$L of $^{186}ReO_4$ (1–50 mCi) is added and incubated for 1–2 minutes to form $^{186}$Re-citrate. Immediately following, hemithioacetal protected opioid receptor ligand (0.1 to 1.0 mg in 600 $\mu$L isopropanol) is added. The reaction mixture is incubated at 90° C.–100° C. for 15–30 min and then is brought to room temperature by rapid cooling in an ice bath.

The following general method may be used to radiolabel opioid receptor ligands having unprotected sulfur atoms in their binding arms with $^{186}$Re (in general, a slightly higher pH is used when the sulfur atoms are in unprotected form vs. when the sulfur atoms are in protected form): a solution of 11.0 mg of citric acid 370 $\mu$g of gentisic acid and 460 $\mu$g of stannous chloride dihydrate in 0.1–1.0 mL $H_2O$ is adjusted to a final pH of 2. To this solution, 500 $\mu$L of $^{186}ReO_4$ (1–50 mCi) is added and incubated for 1–2 minutes to form $^{186}$Re-citrate. In another evacuated vial, 200 $\mu$L of sodium phosphate (0.5 M, pH 8.0) and 1.0 mL of the opioid receptor analog (0.5–1.0 mg/mL) are added successively. Then $^{186}$Re-citrate (50 mCi) is added, and the vial is incubated at 25° C.–100° C. for 10–30 min. The percent formation of radiolabeled compound is determined by ITLC and a gradient HPLC system using a radiometric detector.

The following general method may be used to radiolabel opioid receptor ligands having protected sulfur atoms in their binding arms with $^{188}$Re: sodium perrhenate (3 mL, 15 mCi, produced from a W-188/Re-188 research scale generator) is added to a vial containing lyophilized mixture comprising citric acid, 75 mg; stannous chloride, 0.75 mg; gentisic acid, 0.25 mg; and lactose, 100 mg. The vial is agitated gently to mix the contents, then incubated at room temperature for 10 minutes to form a $^{188}$Re-citrate intermediate exchange complex. To a separate vial containing 0.50–1.0 mg of the opioid receptor ligand comprising a hemithioacetate (ethoxyethyl) sulfur protecting group, 0.5 mL of isopropyl alcohol is added and the vial is agitated for 2 min for complete dissolution of the ligand. Next, 0.3 mL of this solution is transferred to the vial containing the $^{188}$Re-citrate complex prepared above. After gentle mixing, the vial is incubated at 95° C.–100° C. for 15–30 min. Then, immediately transferred to a 0° C. ice bath for two minutes. The yields of $^{188}$Re-analog generally range between 90–95% as measured by reverse phase $C_{18}$ HPLC analysis.

The following general method may be used to radiolabel opioid receptor ligands having unprotected sulfur atoms in their binding arms with $^{186}$Re (in general, a slightly higher pH is used when the sulfur atoms are in unprotected form vs. when the sulfur atoms are in protected form): sodium perrhenate (3 mL, 15 mCi, produced from a W-188/Re-188 research scale generator) is added to a vial containing lyophilized mixture comprising citric acid, 75 mg; stannous chloride, 0.75 mg; gentisic acid, 0.25 mg; and lactose, 100 mg. The vial is agitated gently to mix the contents, then incubated at room temperature for 10 minutes to form a $^{188}$Re-citrate intermediate exchange complex. In another evacuated vial, 200–500 $\mu$L of sodium phosphate (0.5 M, pH 8.0) and 1.0 mL of opioid receptor ligand (0.5–1.0 mg/mL) are added successively. Then $^{188}$Re-citrate (50 mCi) is added, and the vial is incubated at 25° C.–100° C. for 10–30 min. The percent formation of radiolabeled compound is determined by ITLC and a gradient HPLC system using a radiometric detector.

Compositions Containing Diagnostically or Therapeutically Effective Compounds having Opioid Receptor Affinity and Radionuclide Chelates Thereof The present invention provides a pharmaceutical or veterinary composition (hereinafter, simply referred to as a pharmaceutical composition) containing a compound of the invention having opioid receptor affinity as described above, in admixture with a pharmaceutically acceptable carrier or diluent. The invention further provides a pharmaceutical composition containing a chelate of a compound of the invention having opioid receptor affinity as described above, in admixture with a pharmaceutically acceptable carrier or diluent.

The pharmaceutical compositions of the present invention may be in any form which allows for the composition to be administered to a subject. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, intrasternal injection or infusion techniques. Pharmaceutical composition of the invention are formulated so as to allow the active ingredients contained therein to be bioavailable upon administration of the composition to a subject. Compositions that will be administered to a subject take the form of one or more dosage units, where for example, a tablet may be a single dosage unit, and a container of opioid receptor ligand of the invention in aerosol form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a compound of the invention having opioid receptor affinity or chelate thereof as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. Calcium (+2) may be added to the composition in instances where the chelate may have some undesirable toxicity. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of the inventive compound or chelate such that a suitable dosage will be obtained. Typically, this amount is at least 0.01% of a compound of the invention in the composition, however the actual amount of label that is effective may be less than 0.01%. When intended for oral administration, this amount may be varied to be between 0.1 and about 70% of the weight of the composition. Preferred oral compositions contain between about 4% and about 50% of the active opioid receptor ligand compound of the invention. Preferred compositions and preparations according to the present invention are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the compound of the invention having opioid receptor affinity or chelate thereof and thereby assists in the delivery of the active components. Suitable agents which may act in this capacity include a monoclonal or polyclonal antibody, an antigen-binding fragment of a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

Whether in solid, liquid or gaseous form, the pharmaceutical composition of the present invention may contain one or more known pharmacological agents useful in the therapeutic effect that is desired.

The pharmaceutical compositions may be prepared by methodology well known in the pharmaceutical art. A composition intended to be administered by injection can be prepared by combining the compound of the invention having opioid receptor affinity or chelate thereof with water so as to form a solution. A surfactant may be added to facilitate the formation of a homogeneous solution or suspension. Surfactants are compounds that non-covalently interact with the inventive compound/chelate so as to facilitate dissolution or homogeneous suspension of the inventive compound/chelate in the aqueous delivery system.

The present invention provides that an effective amount of a compound or composition of the present invention may be used to detect, diagnose or treat diseases of cells having opioid receptors. These cells are typically mammalian cells. Diseases that may be detected, diagnosed or treated according to the present invention include certain dementia of the brain. Thus, an imaging compound of the invention may be injected or otherwise delivered into the central nervous system, to identify and in some instances quantitate opiate receptors in the brain. Dementia of the brain include schizophrenia, epilepsy, Alzheimer's disease, and abnormalities due to narcotic drug addition. Compounds of the invention having morphine-like ligand groups are particularly suitable for monitoring changes in the brain due to narcotic drug addition. A preferred compound for this method contains a $^{99m}$Tc atom.

A disease that may be detected or treated according to the present invention is cancer, including the detection or treatment of neuroendocrine tumors. Adult neuroendocrine tumors that may be detected or treated according to the present invention include, without limitation, (listed as indolent biology/aggressive biology) carcinoid tumors (many primary sites)/small cell lung cancer, atypical or poorly differentiated carcinoids (many primary sites); islet cell tumor (pancreas)/extrapulmonary small cell carcinoma (many primary sites); pheochromocytoma (adrenal)/peripheral neuroepithelioma-neurons (usually in adolescents); medullary carcinoma (thyroid)/market cell tumor (skin); and paraganglioma-neurons/neuroblastoma (adrenal). One or more neuroendocrine carcinomas may be found in the gastrointestinal tract, including without limitation, carcinoid tumors, gastrinomas, insulinomas, glucagonoma, somatostatinoma, vipomas, and pancreatic polypeptideoma. Leukemia and lymphomas are other cancer types that may be detected or treated according to the present invention.

Neuroendrine tumors may be targeted with compounds of the invention having naltrindole-like ligand portions. Opioid receptors have been reported to be present on lung cancer cells, to a greater extent than on other cell types of a host, outside of the central nervous system (see, e.g., Campa et al. Can. Res. 56:1965–1701, 1996). A charged compound of the present invention that is administered systemically should not be able to cross the blood-brain barrier. DOTA-derivatives of the invention are examples of such charged compounds of the present invention. Thus, a chemical of the invention which is toxic to cells should become localized at lung cancer cells, and not adventitiously bind to opioid receptor in the central nervous system.

Methods of administering effective amounts of the inventive compounds or chelates thereof include the administration of inhalation, oral or parenteral forms. Such dosage forms include, but are not limited to, parenteral solutions, tablets, capsules, sustained release implants and transdermal delivery systems; or inhalation dosage systems employing dry powder inhalers or pressurized multi-dose inhalation devices. The dosage amount and frequency are selected to create an effective level of the agent without harmful effects. It will generally range from a dosage of about 0.1 to 100 mg/Kg/day, and typically from about 0.1 to 10 mg/Kg/day where administered orally or intravenously. Also, the dosage range will be typically from about 0.01 to 1 mg/Kg/day where administered intranasally or by inhalation.

Therapeutic Applications of Opioid Recepetor Ligands having Radionuclide Binding Arms Chelated with Radionuclides Yet another embodiment of the invention provides methods for using a compound of the invention having opioid receptor affinity chelated with radionuclide as described above for therapeutic purposes. The therapeutic method may be used for delivering a radionuclide to a target site within a mammalian host. The method comprises the step of administering to a mammal a therapeutically effective dose of one of the radiolabeled compounds as described above. A therapeutically effective dose is generally from about 20 mCi to about 300 mCi. Preferred radionuclides are $^{186}$Re, $^{90}$Y, $^{188}$Re, $^{67}$CU, $^{105}$Rh, $^{198}$Au, $^{199}$Au and $^{212}$Bi. A preferred mammal is man.

The chelates of the present invention may be administered to a mammalian host, normally by injection, intravenously, intraarterially, peritoneally, intratumorally, or the like, depending upon the particular site at which the radionuclide is desired. Generally, from about 1–30 mL will be injected into a host, depending upon the size of the host, with about 1–10 mCi/Kg of host. For human hosts, the therapeutic dosage will usually be about 70–700 mCi/70 Kg host, more usually about 25–35 mCi/70 Kg host of the diagnostic dosage. For lower mammals, e.g., mice, 1–50 $\mu$Ci will be used for biodistribution studies, while up to or greater than 0.5–2 mCi will be used for imaging studies. Multiple injections may be use d in a therapeutic method, where the injections may be spaced, for example, about 1 week apart. After administration of the radionuclide, depending upon its purpose, the host may be treated in various ways for detection of the radioactive emissions from the site or sites where the radionuclide specifically binds.

Diagnostic Applications of Opioid Receptor Ligands having Radionuclide Binding Arms Chelated with Radionuclides Yet another embodiment of the invention provides methods for using the radiolabeled compounds described above for diagnostic purposes. The diagnostic method may be used to detect the presence or absence of a target site within a mammalian host. The method comprises the steps of administering to a mammal a diagnostically effective dose of one of the radiolabeled compounds described above. This step is followed by a step of detecting the biodistribution of the radionuclide in the mammal to deter mine the presence or absence of the target site in the host.

A diagnostically effective dose of a radiolabeled compound is generally from about 5 to about 35 and typically from about 10 to about 30 mCi per 70 Kg body weight. The precise dose for a radiolabeled compound is dependent upon the particular receptor which is being targeted because the level of uptake of a radiolabeled compound into a tumor is dependent upon the number of receptors for the compound and its affinity for the receptors. The precise dose further depends upon the particular route of administration, e.g., intravenous, intracompartmental, intraarterial or intratumoral. It will be evident to one skilled in the art how to determine the optimal effective dose for a particular radiolabeled compound and a particular route of administration. Preferred radionuclides are $^{111}$In, $^{97}$Ru, $^{99m}$Tc and $^{203}$Pb. A preferred mammal is man.

The therapeutic method may be used for delivering a radionuclide to a target site within a mammalian host. A preferred target site is a lung, which may contain small cell cancer. The method comprises the step of administering to a mammal a therapeutically effective dose of one of the radiolabeled compounds described above. A therapeutically effective dose is generally from about 20 mCi to about 700 mCi. Preferred radionuclides are $^{90}$Y, $^{186}$Re, $^{188}$Re, $^{67}$Cu, $^{105}$Rh, $^{198}$Au, $^{199}$Au $^{212}$Bi. A preferred mammal is man.

The chelates of the present invention may be administered to a mammalian host, normally by injection, intravenously, intraarterially, peritoneally, intratumorally, or the like, depending upon the particular site at which the radionuclide is desired. Generally, from about 1–30 ml, will be injected into a host, depending upon the size of the host, with about 1.0–10 mCi/Kg of host. For human hosts, the therapeutic dosage will usually be about 70–700 mCi/70 Kg host, more usually about 25–35 mCi/70 Kg host of the diagnostic dosage. For lower mammals, e.g., mice, 1–50 µCi will be used for biodistribution studies, while up to or greater than 0.5–2.0 mCi will be used for imaging studies. After administration of the radionuclide, depending upon its purpose, the host may be treated in various ways for detection of the radioactive emissions from the site or sites where the radionuclide specifically binds. The total dose can be given as a single injection or can be split into several multiple injections.

Kits Containing Opioid Receptor Ligands having Radionuclide Binding Arms Chelated With Radionuclides, and Preparation and Uses Thereof In another embodiment of the invention, an opioid receptor ligand having radionuclide binding arms as described above may be included in a kit for producing a metal species-chelated compound of the invention (a "radiolabeled compound") for radiopharmaceutical use. Reagents useful in reactions to radiolabel the compound with a radionuclide may be included. Such kits also may comprise a means for purifying the radiolabeled compound away from the reaction mixture in which it was formed, as well as specific instructions for producing the radiolabeled compound using the kit components.

Such kits generally will be used in hospitals, clinics or other medical facilities. Since such facilities generally have ready access on a daily basis to radionuclides, including isotopes of technetium, and since isotopes of rhenium, yttrium, lead, bismuth, palladium, and copper may be prepared as described above, inclusion of the radionuclide in the kit is optional. Exclusion of the radionuclide permits storage of the kit, whereas kits containing the radionuclide (either as a separate component or as the radiolabeled compound) would have to be used within a narrow time frame (depending on the half-life of the particular isotope); otherwise, radioactive decay of the radioisotope would diminish the effectiveness of the diagnostic or therapeutic technique for which the radiolabeled compound is used. For $^{186}$Re and $^{90}$Y, on-site radiolabeling would avoid radiolytic degradation of the labeled compound due to the beta particle emission.

The kits may be diagnostic or therapeutic kits, depending on which radionuclide is used for chelating with the inventive compound. When the radionuclide is to be reduced to a lower oxidation state (e.g., technetium and rhenium, as discussed above), the kits may contain a reducing agent which is effective in reducing a particular metal radionuclide, which is to be chelated by the inventive compound, to an oxidation state at which an exchange complex of the radionuclide may be formed. In addition, a kit may additionally contain a complexing agent with which the reduced radionuclide will form an exchange complex, where this exchange complex is a useful intermediate in forming the radiolabeled compound.

The kit components and instructions will be somewhat different when the inventive compound is to be radiolabeled with a technetium isotope (i.e., a diagnostic kit) than when the inventive compound is to be radiolabeled with a yttrium, indium, rhenium, lead, bismuth, palladium, or copper isotope (i.e., a therapeutic kit). The different components and procedures are discussed in more detail below. In the following discussion, the term "separate containers" is meant to include not only separate, individual containers (e.g., vials) but also physically separate compartments within the same container.

In accordance with one embodiment of the invention, a diagnostic kit comprises the following reagents (in separate containers unless otherwise noted), presented in the general order of use.

1. A reducing agent effective in reducing pertechnetate ($^{99m}$TcO$_4^-$ which is in the +7 oxidation level) to a lower oxidation state at a neutral to acidic pH so that a technetium exchange complex can be formed. Many suitable reducing agents are known in the art, including but not limited to stannous ion, (e.g., in the form of stannous salts such as stannous chloride or stannous fluoride), metallic tin, formamidine sulfinic acid, ferric chloride, ferrous sulfate, ferrous ascorbate, and alkali salts of borohydride. Preferred reducing agents are stannous salts.

2. A complexing agent with which the reduced $^{99m}$Tc will form an exchange complex, thus protecting the $^{99m}$Tc from hydrolysis. In order to achieve efficient transfer or exchange of the $^{99m}$Tc from this complex to the inventive compound, the complexing agent advantageously binds the radionuclide more weakly than the compound will. Complexing agents which may be used include, but are not limited to, gluconic acid, glucoheptonic acid, methylene diphosphonate, glyceric acid, glycolic acid, mannitol, oxalic acid, malonic acid, succinic acid, bicine, N,N'-bis(2-hydroxyethyl) ethylene diamine, citric acid, ascorbic acid and gentisic acid. Good results are obtained using gluconic acid or glucoheptonic acid as the Tc-complexing agent (or "exchange agent" in these cases), as they efficiently transfer the $^{99m}$Tc to the inventive compound at a pH at which the active ester is stable.

3. A compound of the present invention, having an opioid receptor ligand site and radionuclide binding arms, as described above.

4. Additional reagents for use in the radiolabeling are optional components of the kits. Examples of such additional reagents include, without limitation, buffers, alcohols, acidifying solutions, and other such reagents as are more fully described herein. Such additional reagents are generally available in medical facilities and thus are optional components of the kit because they can be readily obtained by people using the kits. However, these reagents preferably are included in the kit to ensure that reagents of sufficient purity and sterility are used, since the resulting radiolabeled compounds may be administered to mammals, including humans, for medical purposes.

5. Optionally, a container of a compound of the invention, which may be administered in non-radiolabeled form to a human or mammal, is included in the kit. This inventive compound is reactive with essentially the same target sites (i.e., opioid receptor(s)) as the radiolabeled compound and reduces binding of the radiolabeled compound to cross-reactive binding sites on non-target tissues. The two compounds may be the same, or the compound to be radiolabeled may, for example, be somewhat different from the compound which is to be administered in non-radiolabeled form. The latter inventive compound is administered as an unlabeled specific blocker (prior to administration of the radiolabeled compound) in an amount effective in improving diagnostic imaging of the desired target sites (e.g., tumors as described above).

6. Optionally, the kit may also include a container of a opioid receptor ligand which does not bind through specific mechanisms to sites within the human or mammal to which the radiolabeled compound is to be administered. This opioid receptor compound is administered as an "irrelevant" compound (prior to administration of the radiolabeled compound) in an amount effective in decreasing nonspecific uptake of certain radiolabeled compounds, as described above.

In one embodiment of the invention, a radiolabeled compound may be produced using a kit as described above, according to the following general procedure. The procedure is preferably conducted under sterile conditions. In this particular embodiment of the invention, the kit includes reagents in amounts suitable for preparation of an amount of radiolabeled compound suitable for injection into one human for diagnostic purposes.

An aqueous solution containing a reducing agent and a complexing agent (each as described above) is prepared. The solution may be prepared, for example, by combining stannous chloride dihydrate (which includes the stannous ion reducing agent) and sodium gluconate (a complexing agent) to form a stannous gluconate complex. This stannous gluconate complex may be provided in a single container in the kit. In one embodiment of the invention, the stannous gluconate complex is provided in the kit in dry solid form.

Optionally, one or more stabilizer compounds may be added to the stannous gluconate complex. Many such stabilizer compounds are known in the art, and some are discussed in connection with the therapeutic kits below. For example, gentisic acid may be added to a container of the stannous gluconate complex to stabilize (minimize oxidation of) the stannous ion reducing agent, and the resulting mixture may be provided in the kit in dry solid form or as a lyophilized preparation. A filler compound advantageously is added prior to lyophilization, as described for the therapeutic kit below. For example, lactose may be added as a filler compound in an amount effective to facilitate lyophilization. The amounts of stannous chloride and sodium gluconate preferably are not so large as to have adverse effects on the desired reactions and product. For example, an excessively large amount of free sodium gluconate may slow the transchelation step and require addition of excessive amounts of buffer necessary to raise the pH in subsequent steps, and the reaction mixtures would then be undesirably dilute. An acceptable ratio of stannous chloride dihydrate to sodium gluconate (by weight) is from about 1:10 to about 1:100, preferably from about 1:25 to about 1:70, most preferably about 1:41.6.

The amount of $^{99m}$Tc added may vary. When the diagnostic kit is designed for preparation of a radiolabeled compound to be injected into a single human patient, the amount of pertechnetate to be added to the following reaction mixture may be from about 50 to about 200 mCi, preferably from about 75 to about 100 mCi of the radionuclide. Greater amounts may interfere with the reaction and produce low yields, as well as generating an excessive amount of radioactivity for administration to a single patient. When about 75 to 100 mCi of $TcO_4^-$ are to be added, the stannous gluconate complex preferably is formed from about 3 to about 10 mg of sodium gluconate and about 0.075 to about 0.250 mg of stannous chloride dihydrate; preferably from about 4 to about 6 mg of sodium gluconate and about 0.075 to about 0.125 mg of stannous chloride dihydrate.

Using the reagents described above, sodium pertechnetate is combined with the reducing agent and complexing agent. When the sodium pertechnetate is added to stannous gluconate, the radionuclide is effectively reduced to a lower oxidation state and complexed with gluconate to form an exchange complex. The stannous gluconate and pertechnetate may be combined in various ways. In one embodiment of the invention, sterile water is added to a vial containing a stannous gluconate preparation in dry solid form. A portion of the resulting solution is combined with about 0.75 mL sodium pertechnetate (about 75 to 100 mCi). In another embodiment of the invention, sodium pertechnetate (about 1 mL) is added directly to a lyophilized preparation comprising stannous gluconate, gentisic acid as a stabilizer, and lactose as a filler compound. In either case, the reaction mixture is incubated at about 25° C. to about 50° C., preferably at about 25° C. to about 3° C. for a minimum of 10 minutes. Incubation for 10 minutes generally gives sufficient yields of the desired technetium exchange complex (e.g., technetium gluconate) while minimizing the formation of insoluble technetium dioxide, which may increase with increased incubation time.

An opioid receptor ligand having radionuclide binding arms of the invention is added to an organic solvent which is effective in dissolving the ligand and effective for the exchange reaction that follows. Suitable solvents should be nontoxic in mammals and inert toward the reactants in the reaction mixture. Organic solvents which may be used include, without limitation, acetonitrile, ethyl acetate, and methylethyl ketone. When the radiolabeled compound is to be injected into humans, however, suitable organic solvents include, but are not limited to, alcohols such as ethanol, butanol, tert-butyl alcohol and propanol, and polar aprotic solvents such as DMSO and dimethylformamide (DMF). The choice of solvent may vary according to the particular opioid receptor compound of the invention is to be included in the kit. For example, when the opioid receptor compound includes a tetrafluorophenyl ester group, ethanol may react with the ester in a transesterification reaction, producing ethyl ester as a by-product. A preferred organic solvent is isopropyl alcohol. The concentration of the organic solvent in the following Tc-labeling exchange reaction mixture should be between about 10% and about 30%, preferably between about 15% and about 25%.

The solution comprising the opioid receptor compound in the organic solvent is then acidified to a pH of about 2.0 to about 5.0, preferably 2.8 to 3.3. At these acidic pH conditions, the formation of insoluble $TcO_2$ will be minimized. Also, in this pH range, any hemithioacetal or thioacetal sulfur-protecting groups present in the opioid receptor compound will be displaced by a metal-assisted acid cleavage during the technetium labeling exchange reaction to form the corresponding technetium chelate compound. Also, hydrolysis of ester groups on the opioid receptor compound is minimized under acidic conditions when compared to basic conditions. Suitable acids are added in amounts sufficient to displace the sulfur-protective groups, if present, in the presence of the metal radionuclide (i.e., in amounts sufficient to adjust the reaction mixture to the above-described pH values range). Suitable acids include but are not limited to, phosphoric acid, sulfuric acid, nitric acid, glacial acetic acid, hydrochloric acid and combinations thereof. Also included are solutions including such acids and buffers (e.g., acetate and phosphate buffers). A solution including glacial acetic acid and 0.2 N HCl at a ratio of 2:14 is a typical acid solution in the present invention.

The acidified solution of opioid receptor compound is combined with the previously prepared technetium exchange complex solution, to form the corresponding radiolabeled compound. Typically, about 100 μg to about 150 μg, preferably about 135 μg of opioid receptor compound is combined with the Tc-gluconate complex prepared from the 75 to about 100 mCi of technetium as described above. The reaction mixture is heated to between about 50° C. and 100° C. for a time ranging from about 5 minutes to about 45 minutes. Typically, the desired radiolabeled compound may be produced by heating at about 75° C. for about 15±2 minutes. Heating the reaction mixture accelerates the exchange reaction to form the chelate between the opioid receptor compound and the radionuclide. Upon completion of the reaction, the mixture is transferred immediately to a 0° C. ice bath for a minimum of 2 minutes to stop the reaction quickly and at this temperature the radiopharmaceutical is stable. For practical purposes, the radiopharmaceutical can be stored at room temperature for several hours.

An aqueous solution including a buffer may then be added to the reaction mixture in order to reduce the concentration of the organic solvent(s) and to adjust the pH as desired. Suitable buffers include nontoxic buffers which are inert toward the reactants, such as, but not limited to, sodium phosphate buffer and sodium bicarbonate buffer, preferably at a concentration of about 1.0 M and a pH of about 10. Buffers such as TRIS must be used cautiously because the free amine groups of TRIS are reactive with ester groups that may be present as part of the opioid receptor ligand of the invention. Sufficient buffer is added to reduce the organic solvent concentration to an amount ranging from about 10% to about 15%, preferably from about 7.5% to about 12.5% (on a weight basis, based on the entire weight of reaction product solution).

In accordance with another embodiment of the invention, a therapeutic kit includes the following reagents.

1. A reducing agent effective in reducing $ReO_4^-$, which is in the +7 oxidation level, to a lower oxidation state at a neutral to acidic pH so that a rhenium exchange complex can be formed. Many suitable reducing agents for this purpose are known in the art, including but not limited to stannous ion (e.g., in the form of stannous salts such as stannous chloride or stannous fluoride), metallic tin, formamidine sulfinic acid, ferric chloride, ferrous sulfate, ferrous ascorbate, and alkali salts of borohydride. Preferred reducing agents are stannous salts.

2. A complexing agent with which the reduced Re will form an exchange complex, thus protecting the Re from hydrolysis. In order to achieve efficient transfer or exchange of the Re from this complex to the opioid receptor ligand of the invention, the complexing agent advantageously binds the radionuclide more weakly than the ligand will. Complexing agents which may be used include, but are not limited to, methylene diphosphonate, glyceric acid, glycolic acid, mannitol, oxalic acid, malonic acid, succinic acid, bicine, N,N'-bis(2-hydroxyethyl) ethylene acid, succinic diamine, citric acid, ascorbic acid, gentisic acid, tartaric acid, and gluconic acid. A referred complexing agent is citric acid, which may be used to form a Re-complexing gent complex (or "exchange agent" in these cases).

3. A opioid receptor ligand of the invention as described above.

4. Additional reagents for use in the radiolabeling are optional components of the kits. Examples of such additional reagents include, without limitation, buffers, alcohols, acidifying solutions, and other such reagents as are more fully described herein. Such additional reagents are generally available in medical facilities and thus are optional components of the kit because they can be readily obtained by people using the kits. However, these reagents preferably are included in the kit to ensure that reagents of sufficient purity and sterility are used, since the resulting radiolabeled compounds may be administered to mammals, including humans, for medical purposes.

5. Optionally, a container of opioid receptor ligand of the invention, which may be administered in non-radiolabeled form to a human or mammal, is included in the kit. This inventive ligand is reactive with essentially the same target sites as the radiolabeled compound and reduces binding of the radiolabeled compound to cross-reactive binding sites on non-target tissues. The two compounds may be the same, or the compound to be radiolabeled may, for example, be somewhat different from the compound which is to be administered in non-radiolabeled form. The latter opioid receptor ligand of the invention is administered as an unlabeled specific blocker (prior to administration of the radiolabeled compound) in an amount effective in improving diagnostic imaging of the desired target sites (e.g., tumors as described above).

6. Optionally, the kit may also include a container of an opioid receptor ligand of the invention which does not bind through specific mechanisms to sites within the human or mammal to which the radiolabeled compound is to be administered. This opioid receptor ligand of the invention is administered as an "irrelevant" compound (prior to administration of the radiolabeled compound) in an amount effective in decreasing nonspecific uptake of certain radiolabeled compounds, as described above.

In one embodiment of the invention, an opioid receptor ligand of the invention radiolabeled with either $^{188}$Re or $^{186}$Re may be prepared using such a kit, according to the following general procedure. The procedure is conducted under sterile conditions.

Perrhenate (the $ReO_4^-$ form of the $^{186}$Re or $^{188}$Re isotope) is reacted with reducing agent and a complexing agent. For instance, citric acid (a complexing agent) may be combined with stannous chloride (a reducing agent) in a single container (in which a stannous citrate complex is believed to form) and the perrhenate may then be added thereto.

The amounts of stannous chloride and citric acid added should not be so large as to have adverse affects on the desired reactions. For example, an excessively large amount of free citric acid may lower the pH to a level which makes addition of large quantities of buffer necessary to raise the pH in subsequent steps, and the reaction mixtures would be undesirably dilute. An acceptable ratio of stannous chloride to citric acid (by weight) generally ranges from about 1:10 to about 1:500, preferably from about 1:20 to about 1:200, most preferably about 1:100.

One or more stabilizer compounds may be added to the stannous citrate complex. Many such stabilizer compounds are known. See, e.g., U.S. Pat. Nos. 4,440,738 and 4,510,125. Advantageously, gentisic acid is added to the stannous citrate to stabilize (e.g., to prevent oxidation of) the stannous ion. The stabilizer is added to a solution including the stannous chloride reducing agent (and the complexing agent) in an amount effective to stabilize the stannous ion so that the shelf life (stability) of the stannous ion is increased. The solution may be lyophilized and provided in the kit as a lyophilized powder.

When the stannous citrate solution is to be lyophilized, a "filler compound" may be added to the solution to provide bulk or mass and to aid in the lyophilization process. Lactose is a suitable filler compound.

In one particular embodiment of the invention, an aqueous solution of stannous citrate may be prepared by combining about 75 mg citric acid with about 750 μg stannous chloride. About 250 μg gentisic acid may then be added. Typically, as the amount of gentisic acid decreases, the stabilizing effect was not as efficient, whereas when the amount of gentisic acid increases there is a negative affect on yields. About 100 mg lactose (a preferred amount) may then be added to the preparation, although about 20 mg is typically adequate. The final solution (about 2 mL volume) may then be lyophilized.

Perrhenate may then be added to the stannous citrate preparation. Perrhenate may be introduced into the preparation as an aqueous solution of the sodium salt (e.g., eluted from a rhenium generator) or as an aqueous solution of the tetrabutylammonium ion pair. Either way, perrhenate is incubated with a solution that includes a reducing agent and a complexing agent. The reaction mixture is incubated at a temperature ranging from about 25° C. to about 50° C., preferably at about 25° C. to 37° C., for a minimum of 10 minutes. Incubation for 10 minutes generally gives sufficient yields of the desired rhenium exchange complex (e.g., rhenium-citrate), while minimizing the formation of insoluble rhenium dioxide.

An opioid receptor ligand of the invention, which may contain thioacetal or hemithioacetal sulfur-protecting groups in the radionuclide binding arms, may then be dissolved in an organic solvent which is both effective in dissolving the ligand and is suitable for the exchange reaction that follows. Suitable solvents should be non-toxic in mammals and inert toward the reactants in the reaction mixture. Organic solvents which may be used include, without limitation, acetonitrile, ethyl acetate, and methyl ethyl ketone. When the radiolabeled compound is to be injected into humans, however, suitable organic solvents include but are not limited to alcohols such as ethanol, butanol, tert-butyl alcohol, and propanol and polar aprotic solvents such as DMSO and dimethylformamide (DMF). The choice of solvent may vary according to the particular opioid receptor ligand of the invention included in the kit. For example, when the ligand includes a tetrafluorophenyl ester group, ethanol may react with the ester in a transesterification reaction, producing ethyl ester by-products which are undesirably lipophilic. A preferred organic solvent is isopropyl alcohol.

The solution which includes the opioid receptor ligand of the invention in the organic solvent may be combined with the rhenium exchange complex solution prepared above, to form the corresponding rhenium-chelated opioid receptor ligand. Typically, the reaction is advantageously conducted at a pH of from about 1.5 to about 5.0, preferably from about 1.7 to about 2.0. At these acidic pH conditions, the formation of insoluble $ReO_2$ will be minimized; and as explained above, hemithioacetal and thioacetal sulfur-protecting groups (if present) will be displaced by a metal-assisted acid cleavage during the rhenium labeling exchange reaction to form the corresponding rhenium chelate compound. Also, hydrolysis of ester groups on the opioid receptor ligand compound of the invention is minimized under acidic conditions when compared to basic conditions. If adjustment of the pH of the reaction mixture is necessary, suitable acids may be added in amounts sufficient to displace the sulfur-protective groups in the presence of the metal radionuclide (i.e., in amounts sufficient to adjust the reaction mixture to the above-described pH values range). Suitable acids include, but are not limited to, phosphoric acid, sulfuric acid, nitric acid, glacial acetic acid, hydrochloric acid, and combinations thereof. Also included are solutions comprising such acids and buffers (e.g., acetate and phosphate buffers).

The amount of opioid receptor ligand of the invention reacted with the Re-citrate intermediate may vary according to the reaction volume, which in turn varies according to the volume in which perrhenate was added in an earlier step (e.g., perrhenate may be added as an eluent from the generator or may first be concentrated). In one embodiment of the invention, the concentration of chelating compound in the reaction mixture (in which the chelate is formed) ranges from about 100 μg to about 200 μg of opioid receptor ligand of the invention per mL of reaction mixture.

To accomplish chelation of the opioid receptor ligand of the invention, the reaction mixture may be heated to a temperature between about 50° C. and 100° C. for a time of from about 5 to about 45 minutes. Typically, heating at about 75° C. for about 10 minutes is sufficient. Upon completion of the reaction, the mixture may be transferred immediately to a 0° C. ice bath for a minimum of 2 minutes in order to stop the reaction and is stable at 0° C. to 25° C. for several hours.

The following examples are provided for purposes of illustration, not limitation.

EXAMPLES

RPHPLC conditions for Examples 1 and 2 are as follows: Hewlett Packard 1090 HPLC with diode array detection; analytical reverse phase C18 column eluted at 1.0 mL/min with a mixture of solvents A and B, where A=0.1% trifluoroacetic acid (TFA) in water, B=90% acetonitrile (MeCN) containing 0.1% TFA. RPHPLC conditions for Examples 3–5 and 8–20 are as follows: Hewlett Packard 1090 HPLC with diode array detection; analytical reverse phase C18 column eluted at 1.0 mL/min with a mixture of solvents A and B, where A=5% MeCN, 0.1% TFA; B=95% MeCN, 0.1% TFA. Each gradient is preceded by 4 minutes under initial solvent conditions and followed by a wash period at higher %B (usually 100%B) and re-equilibration to starting conditions.

Unless otherwise stated, chemicals and reagents are obtained from chemical supply houses known in the art, for example, Aldrich, Milwaukee, Wis. As used herein, ret time represents retention time; con HCl represents concentrated hydrochloric acid; h represents hours; NID represents naltrindole; TLC represents thin layer chromatography; PSI represents pounds per square inch; EtOAc represents ethyl acetate; min represents minutes;

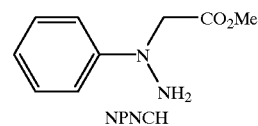

NPNCH

Example 1

N-phenyl-N-carboxymethyl hydrazine (NPNCH), CAS Registry No. 4408-70-2

Nitrosation of N-phenyl glycine (NPG). (Procedure from Organic Synthesis II pg. 460)

NPG (Aldrich; 1.51 g, 10 mmol) is dissolved in 1.45 mL con HCl, then diluted with 2 mL $H_2O$ and cooled on ice. $NaNO_2$ (0.70 g, 10 mmol) is dissolved in 2 mL $H_2O$ and added over 10 minutes to the cooled NPG solution. The precipitate which forms is filtered. Product is analyzed by isocratic RPHPLC with 30%B: NPG ret time=3.7 min, $\lambda_{max}$=240, 290 nm; product ret time=6.2 min, $\lambda_{max}$=270 nm. Reduction of N-nitroso, N-phenyl glycine The precipitate as prepared above. is suspended in 3 mL HOAc and added in 30 fractions to 2.0 g Zn dust suspended in 3 mL $H_2O$. Analysis of the reaction mixture by RPHPLC (30% B) reveals disappearance of the starting material, and appearance of two products, one identical by retention time and UV spectrum with NPG, the other a new compound with ret time=2.8 min and $\lambda_{max}$=274 nm. The reaction mixture is filtered and the solids washed with water. The filtrate is evaporated to dryness under reduced pressure, then applied to a C18 flash column equilibrated in 10% MeCN, 0.1% TFA, and eluted with a stepwise gradient of 10, 20, 30, and 50% MeCN, all containing 0.1% TFA. Product containing fractions are identified by HPLC, combined and evaporated under reduced pressure. Product is analyzed by $^1H$ NMR in $d_7$DMF: δ (ppm)=7.25 (t, 2H), 7.1 (d, 2H), 6.8 (t, 1H), 4.4

(s, 2H), and by low resolution electron impact mass spectroscopy (MS): molecular ion=166.1.

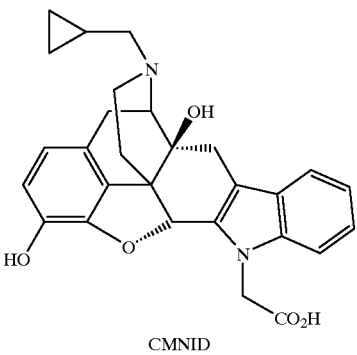

CMNID

Example 2

N1'-carboxymethyl naltrindole. (CMNID)

The following procedure was adapted from "δ Opioid Antagonist Activity and Binding Studies of Regioisomeric Isothiocyanate Derivatives of Naltrindole: Evidence for δ Receptor Subtypes", *J. Med. Chem.* 35:4086–91 (1992).

NPNCH (51 mg, 0.31 mmol) and naltrexone hydrochloride (Sigma, 100.3 g, 0.26 mmol) are stirred overnight in 3 mL methanol (MeOH). The resulting mixture is evaporated to dryness under reduced pressure, then taken up in 5 mL con HCl and placed on an oil bath heated to 150° C. under a water cooled condenser. After 1 hour the heat is turned off and the mixture left overnight. RPHPLC reveals a new peak with ret time 7.1 min (30% B) and a UV spectrum indistinguishable from authentic naltrindole (provided by Dr. Wendell Nelson, Univ. of Washington).

The reaction mixture is filtered and the solid applied to a C18 flash column equilibrated in 25% MeCN containing 0.1% TFA. The column is eluted with a step gradient of 25, 30, and 35% MeCN, all containing 0.1% TFA. Fractions containing the putative product are identified by RPHPLC, pooled, and evaporated to dryness under reduced pressure. The product is analyzed by $^1$H NMR in $CD_3OD$ and by low resolution FAB MS. Comparison of the $^1$H NMR spectrum with that of naltrindole in $CDCl_3$, naltrindole in $CD_3OD$, and naltrexone hydrochloride in $CD_3OD$ reveals that the product spectrum is attributable to the protonated form (i.e., TFA salt) of the desired product. Signals at δ=5.20 and 5.05 ppm (distorted doublets, 1H each), not found in any of the other spectra, are attributable to the prochiral methylene protons of the carboxymethyl group. FAB MS gives the expected M+H peak at 473.

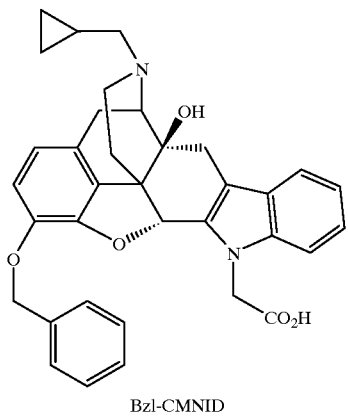

Bzl-CMNID

Example 3

1'-N-carboxymethyl-3-O-benzyl naltrindole (Bzl-CMNID)

3-O-benzyl natrindole (Bzl-NID) was prepared according to "Synthesis of N1'-([$^{11}$C]methyl)naltrindole ([$^{11}$C]MeNTI): "A Radioligand for Positron Emission Tomographic Studies of Delta Opioid Receptors," *J. Labeled Compd. Radiopharm.* 36:137–45 (1995). Bzl-NID (300.6 mg, 0.6 mmol) is taken up in 1 mL dry DMF and added to a stirred suspension of NaH (60% dispersion in mineral oil; 126.9 mg, ~3 mmol) in 3 mL dry DMF. The suspension is allowed to stir 20 min, then methyl bromoacetate (Aldrich, 71 mL, 0.75 mmol) is added dropwise. The reaction is followed by RPHPLC using a 14 min gradient from 20 to 70% B. Immediately after completion of addition of the methyl bromoacetate, RPHPLC reveals 2 new peaks with retention times of 17.5 and 19.2 min, respectively. After 30 to 60 min only the 17.5 min peak remains. The reaction is quenched by the addition of 2 mL of a 4:1 MeOH:AcOH mixture. The quenched reaction mixture is evaporated under reduced pressure, taken up in 5 mL MeOH, which is then saturated with water, and the mixture applied to a C18 flash column equilibrated in 50% MeOH. The column is eluted with a step gradient of 50, 60, 70, 80, and 100% MeOH, with the product eluting at the end of the 70% step. Product containing fractions are evaporated to dryness under reduced pressure.

$^1$H NMR ($CD_3OD$): comparison with $^1$H NMR of Bzl-NID shows the appearance of 2 new asymmetric doublets, 1H each, at δ=4.8 and 4.92 ppm, respectively, attributable to the methylene protons of the carboxymethyl moiety. ESI MS: expected M+H ($C_{35}H_{36}N_2O_5$+H)=563.

That the product of Example 3 was the free acid rather than the methyl ester is surprising. The late eluting peak that appears early in the reaction and then disappears has been shown to be the expected ester. While the conversion of methyl ester to acid under the reaction conditions is not understood, the spectral data are clear and the product performs as expected in subsequent reactions.

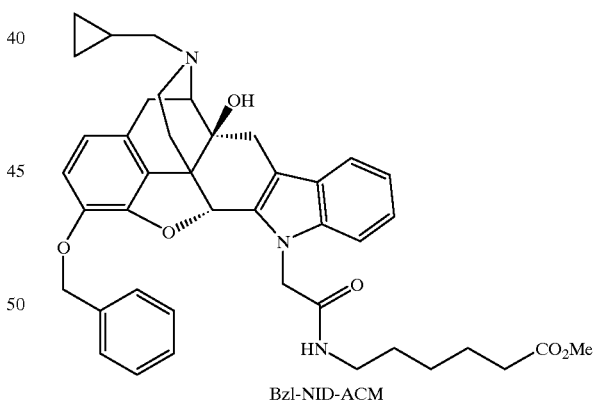

Bzl-NID-ACM

Example 4

Methyl-N-(1'-N-(3-O-benzyl)-naltrindolyl)-6-acetamidocaproate (Bzl-NID-ACM)

Bzl-CMNID (302.2 mg, 0.538 mmol) and methyl-6-aminocaproate hydrochloride (prepared from 6-aminocaproic acid (Aldrich) in methanolic HCl) are dissolved in 6 mL dry DMF, followed by BOP (Benzotriazol-1-yloxy-tris(dimethyl-amino)phosphonium hexafluorophosphate; Chem-Impex Intl., Wood Dale Ill.; 290.4 mg, 0.65 mmol) and ethyldiisopropyl amine (Aldrich; 0.935 mL, 5.5 mmol). The reaction is followed by PRHPLC, using a gradient form 40 to 100% B in 18 min, and by TLC using Silica eluted with 1:1 ethyl acetate (EtOAc):hexane (hex) containing 2% triethylamine. Analysis at early timepoints shows the disappearance of Bzl-CMNID and appearance of a new peak (RPHPLC ret time=10.2 min), which disappears with the appearance of a product peak (RPHPLC ret time= 13.9 min). When starting material and intermediate peaks are consumed, the reaction mixture is evaporated to dryness under reduced pressure and applied, as a concentrated solution in $CH_2Cl_2$, to a Silica flash column equilibrated in 3:1 EtOAc:hex containing 2% triethylamine. The column is eluted with a stepwise gradient of 150 mL 3:1, 100 mL 2:1, and 200 mL 1:1 EtOc:hex all containing 2% triethylamine. Product containing fractions are identified by TLC, pooled, and evaporated under reduced pressure. Reaction yield is 88%.

$^{13}C$ and $^1H$ NMR spectra assignments (tentative) are shown below:

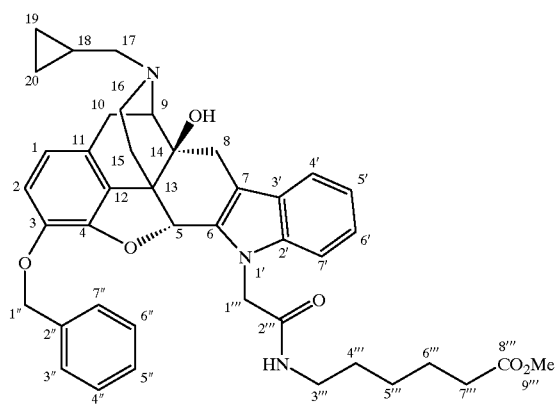

| C # | δ $^{13}C$ (ppm) | δ $^1H$ (ppm) |
| --- | --- | --- |
| 1 | 117.43 | 6.60 |
| 2 | 119.61 | 6.70 |
| 3 | unassigned | |
| 4 | unassigned | |
| 5 | 84.37 | 5.70 |
| 6 | unassigned | |
| 7 | unassigned | |
| 8 | 24.37 | 2.8, 3.15 |
| 9 | 62.42 | 3.40 |
| 10 | 29.17 | 2.6, 2.9 |
| 11 | unassigned | |
| 12 | unassigned | |
| 13 | 48.36 | |
| 14 | 72.84 | |
| 15 | 32.02 | 1.8, 2.4 |
| 16 | 43.84 | 2.3, 2.75 |
| 17 | 59.81 | 2.45 |
| 18 | 9.58 | 0.9 |
| 19 | 3.93/4.24 | 0.2/0.6 |
| 20 | 3.93/4.24 | 0.2/0.6 |
| 2' | unassigned | |
| 3' | unassigned | |
| 4' | 119.83 | 7.5 |
| 5' | 120.62/124.04 | 7.1 |
| 6' | 120.62/124.04 | 7.1 |
| 7' | 110.18 | 7.3 |
| 1' | 48.36 | 4.8, 4.9 |
| 2" | 142.80 | |
| 3",7" | 127.32 or 128.95 | 7.3 |
| 4",6" | 127.32 or 128.95 | 7.3 |
| 5" | 128.45 | 7.3 |
| 1''' | 72.18 | 5.0, 5.1 |
| 2''' | 174.62 or 169.02 | 5.9 |
| 3''' | 39.28 | 3.1 |
| 4''' | 29.17 | 1.0–1.4 |
| 5''' | 26.22 | 1.0–1.4 |
| 6''' | 24.61 | 1.0–1.4 |
| 7''' | 34.05 | 2.05 |
| 8''' | | |
| 9''' | 51.69 | 3.55 |

FAB MS gives the expected M+H ion ($C_{42}H_{47}N_3O_6$+H) 690.

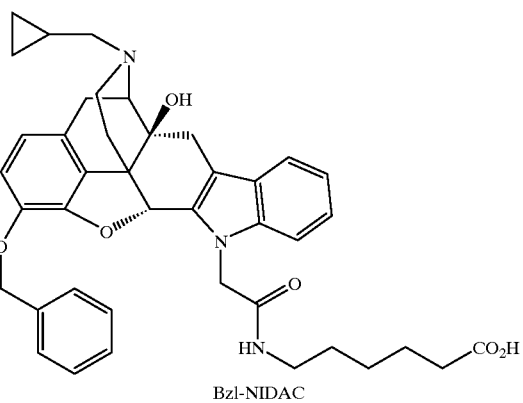

Bzl-NIDAC

Example 5

N-(1'-N-(3-O-benzyl)-naltrindolyl)-6-acetamidocaproic acid (Bzl-NID-AC)

Bzl-NIDACM (315.5 mg, 0.46 mmol) is dissolved in 3 mL MeOH. 1.0 mL 1.0 N NaOH is added. After ~20 minutes, 1 mL MeOH is added to aid in solubility, and the milky white solution is left stirring overnight. 1 N HCl is added until the solution is acidic, then the solution is evaporated to a white solid under reduced pressure. The residue is taken up in MeOH and mechanically separated from precipitated NaCl. Evaporation of the MeOH results in a residue with excess weight, indicating that some salt remains in the product. RPHPLC using an 18 min gradient from 40 to 100% B shows a single new peak ret time=11.1 min. $^1H$ and $^{13}C$ NMR spectra ($CD_3OD$) are similar to those of Bzl-NIDACM, but with peaks shifted due to protonation of the basic tertiary amine by the carboxyl group, and missing the signals assigned to the methyl ester. ESI MS gives the expected M+H ion ($C_{41}H_{45}N_3O_6$+H) at 676.3.

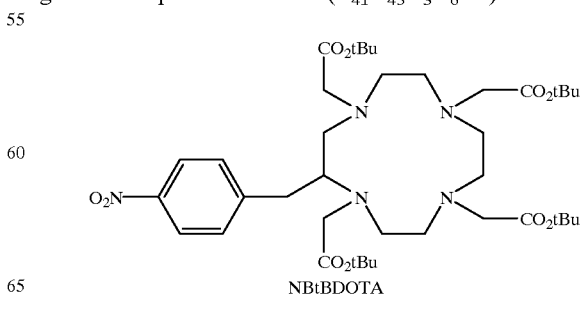

NBtBDOTA

Example 6

2-(4-nitrobenzyl)-1,4,7,10-tetraazadodecane-N1, N4N7,N10-tetra-t-butylacetate (NBtBDOTA)

To 2-(4-nitrobenzyl)-1,4,7,10-tetraazadodecane, (208.4 mg, 0.5 mmol) prepared as in U.S. Pat. No. 5,541,287, in 6 mL dry DMF and $K_2CO_3$ (691 mg, 5 mmol) is added t-butyl bromoacetate (Aldrich, 488 mg, 370 mL, 2.5 mmol). The reaction mixture is heated at 50° C. under nitrogen and with a condenser. After 4 hours RPHPLC shows only two peaks in the ratio 93:7. RPHPLC system: 40% A/60% B to 100%B in 15 min; to 50% B/50% C in 5 min; to 20% B/80% C in 5 min, where A=0.1% TFA; B=60% MeCN/40% $H_2O$ with 0.1% TFA; C=100% MeOH; elution rate=1.0 mL/min. The reaction is stopped, filtered, and the filtrate evaporated to dryness under reduced pressure. The crude product is applied to a Silica flash column equilibrated in 6% MeOH in $CH_2Cl_2$, then eluted with 1 L equilibration buffer followed by 0.5 L 7.5% MeOH in $CH_2Cl_2$. Product containing fractions are identified by TLC and HPLC, pooled, and evaporated to dryness under reduced pressure. Integration of the $^1$H NMR spectrum ($CDCl_3$) shows the correct ratio of aromatic protons to t-butyl ester protons (4:36). High resolution mass spectroscopy gives the expected value, 764.4825 for the M+H ion ($C_{39}H_{65}N_5O_{10}$+H; calc. 764.4810).

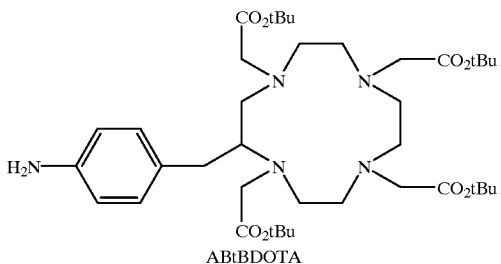

ABtBDOTA

Example 7

2-(4-aminobenzyl)-1,4,7,10-tetraazadodecane-N1, N4,N7,N10-tetra-t-butylacetate (ABtBDOTA)

A solution of NBtBDOTA (280 mg, 0.366 mg) in 14 ml, MeOH is added to a Parr bottle containing 56 mg 10% Pd/C. The bottle is charged with 50 psi $H_2$ in a Parr hydrogenation apparatus. After 3 h TLC (Silica eluted with 7.5% MeOH in $CH_2Cl_2$) shows that the reaction is complete. The mixture is filtered. through a glass fiber membrane and the filtrate evaporated to dryness under reduced pressure. The residue is taken up in $CH_2Cl_2$, and evaporated to dryness again to remove residual MeOH. Reaction yield is quantitative. The $^1$H NMR spectrum shows the expected shift in the aromatic proton signals expected for the nitro to amine conversion. High resolution mass spectroscopy gives the expected value, 734.5037 for the M+H ion ($C_{39}H_{67}N_5O_8$+H; calc. 734.5068).

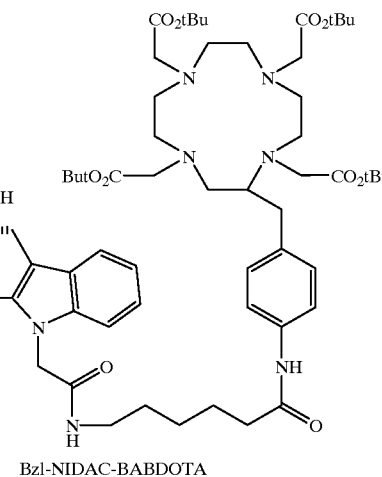

Bzl-NIDAC-BABDOTA

Example 8

(Bzl-NIDAC-BAB DOTA)

ABtBDOTA (157.7 mg, 0.215 mmol), Bzl-NIDAC (96.7 mg, 0.143 mmol), and BOP (97.5 mg, .215 mmol) are combined in an oven dried reaction vessel, then diluted with 2.5 mL dry DMF followed by 250 mL ethyl-diisopropyl amine and stirred magnetically. The reaction is followed by RPHPLC using a gradient from 40 to 100% B in 18 minutes: the Bzl-NIDAC peak is quickly consumed, resulting in a new (intermediate) peak with a ret time of ~14 min; the intermediate peak and the tBABDOTA peak disappear more slowly, and a new peak appears with a ret time of ~16 min and a new UV spectrum. After stirring overnight, RPHPLC indicates that the reaction is complete with a yield>90%. The reaction mixture is evaporated under reduced pressure to a yellow oil which is taken up in $MeCN/H_2O/0.1\%$ TFA and applied to a C18 flash column equilibrated in 50% $MeCN:H_2O$ containing 0.1% TFA. The column is eluted with a step gradient consisting of 100 mL portions of 50, 60, 70, 80, and 90% MeCN, each containing 0.1% TFA. Product containing fractions, identified by TLC, are pooled, neutralized with saturated $NaHCO_3$, evaporated to dryness under reduced pressure, and transferred to a tared vial. The final weight of product exceeds the starting materials, suggesting that some salt accompanies the product. The $^1$H NMR and $^{13}$C ($CDCl_3$) spectra are quite complex, but include features associated with each of the reactants. ESI MS gives the expected M+H ion ($C_{80}H_{110}N_8O_{13}$+H) of 1391.8.

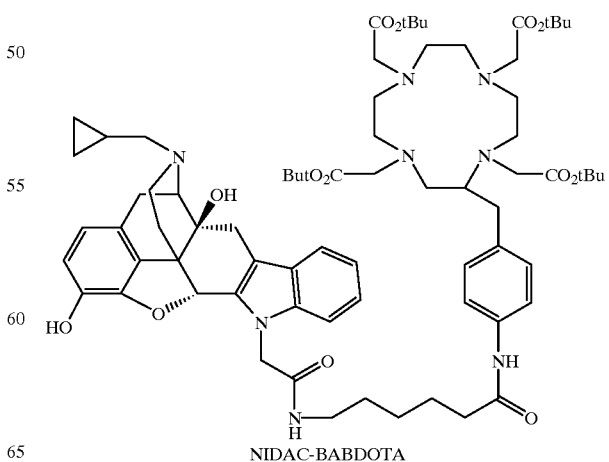

NIDAC-BABDOTA

Example 9

(NIDACBABDOTA)

The Bzl-NIDACBABDOTA of Example 8 is taken up in 4 mL MeOH and placed in a flask containing 21.7 mg of 10% Palladium on charcoal. The suspension is stirred under hydrogen gas overnight, then 23.7 mg additional Pd/C is added and the reaction continues over a second night. The reaction mixture is filtered through glass fiber filter paper, evaporated to dryness under reduced pressure, taken up in 40% MeCN with 0.1% TFA and applied to a C18 flash column equilibrated in 4% MeCN/0.1% TFA. Column is eluted with a step gradient consisting of 40, 50, 55, and 60% MeCN, each containing 0.1% TFA. Product elutes as a slightly yellow band.

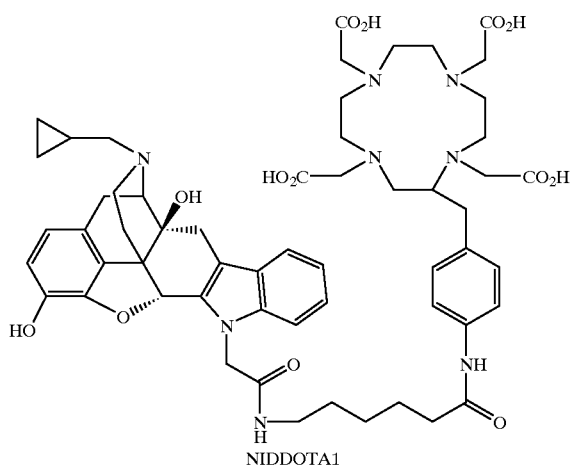

NIDDOTA1

Example 10

(NIDDOTA1)

The NIDACBABDOTA of Example 10 is taken up in 1 mL TFA. The reaction is followed by RPHPLC using a 30 min gradient from 0 to 100% B. After 1 hour the reaction shows consumption of starting material and 4 new peaks. After overnight reaction the reaction mixture shows a single peak with ret time 18.5 min, (vs. 28 min for starting material) and an unchanged UV spectrum. The reaction mixture is evaporated to dryness under reduced pressure then applied in equilibration solvent to a C18 flash column equilibrated in 0.2% HCl. The column is eluted with a step gradient consisting of 200 mL 0.2% HCl, 100 mL 10%, 100 mL 20%, 200 mL 30% MeCN, each containing 0.2% HCl. The product elutes in a single yellow band. The product fractions are identified by HPLC, pooled and evaporated under reduced pressure. The residue is taken up in sterile water, transferred to a tared vial, and evaporated under reduced pressure. Dry wt=42.4 mg. ESI MS of the desired product gives the expected M+H ion ($C_{57}H_{72}N_8O_{13}$+H) of 1077.4.

Example 11

$Y^{3+}$ or $In^{3+}$ NIDDOTA1

An $In^{3+}$ solution (~10 mM) is prepared by dissolving $InSO_4$ in 2 N NH4OAc, pH 5; a $Y^{3+}$ solution (~10 mM) is prepared by dissolving $Y(NO_3)_3$ in 2 N NH4OAc, pH 5. An aliquot of NIDDOTA solution (6 mM) is mixed with a fivefold molar excess of the metal solution. The solution pH is checked and adjusted to 5 if necessary, then the solution is heated to 80° C. in a closed tube for 30 min. The reaction mixture is analyzed by RPHPLC using a gradient from 20 to 40% B in 18 min. NIDDOTA elutes at 13.7 min. The metal loaded chelates elute as two peaks, ret time 11.3 and 12.7 min for In-NIDDOTA, and 10.8 and 12.9 min for Y-NIDDOTA. The UV spectra of the metal loaded and metal free compounds are nearly identical. The metal loaded compounds can be separated from each other and from excess metal by preparative RPHPLC using conditions derived from the analytical separation conditions described above. Low resolution ESI mass spectra of the two $Y^3$ loaded peaks are identical, with the M+H ions of 1163, which is the M+H ion for the chelate complex in which one of the carboxyls is protonated rather than bound to the yttrium ($YC_{57}H_{69}N_8O_{13}$+H). The existence of two forms of $M^{3+}$NIDDOTA complex is explained by diastereomers that result from chelation of the metal on either side of the macrocylic ring relative to the benzyl moiety, which is attached at a chiral center.

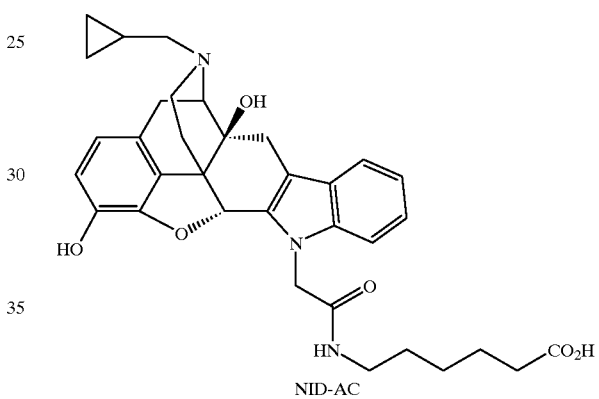

NID-AC

Example 12

N-(1'-N-naltrindolyl)-6-acetamidocaproic acid (NID-AC)

Bzl-NIDAC (Example 5; 92 mg) is added to a stirred flask containing 11.4 mg 10% Pd/C in 5 mL MeOH Hydrogen is introduced from a balloon reservoir and the suspension left stirring overnight. The reaction is monitored by RPHPLC (gradient: 20 to 70% B in 14 min). After overnight reaction RPHPLC shows a single peak eluting earlier than starting material (12 min vs. 19 min). The reaction mixture is filtered through a glass fiber membrane, evaporated under reduced pressure, taken up in MeCN and re-evaporated. The H NMR spectrum ($CD_3OD$) indicates the desired product (benzyl signals absent), but also suggests that the material is impure. Re-analysis by RPHPLC indicates that some degradation has occurred during workup, yielding two contaminants comprising ~20% of the total.

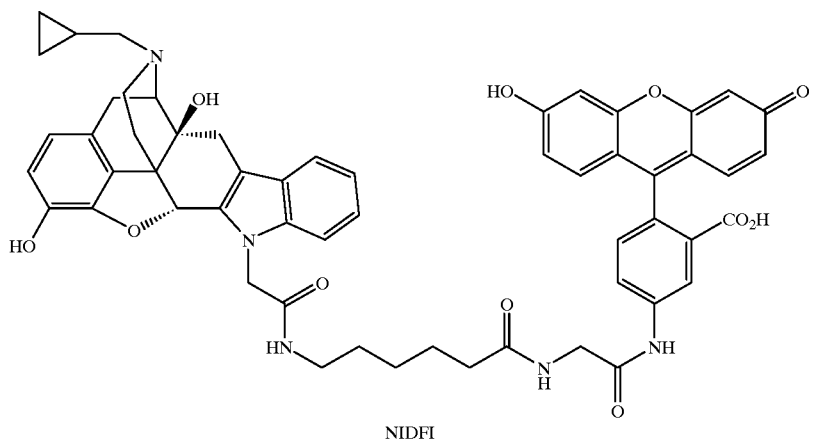

NIDFI

Example 13

(NID-F1)

NIDAC (used as prepared in Example 12; 15 mg, 0.025 mmol) and BOP (12.2 mg, 0.027 mmol) and ethyldiisopropylamine (43.5 mL, 0.25 mmol) are combined in a pre-dried vessel in 0.5 mL dry DMF. After 20 min fluorescein glycinamide (Molecular Probes, Eugene Oreg., #A1363; 10 mg, 0.025mmol) is added. The reaction is monitored by RPHPLC using a gradient from 30 to 60%B in 18 min and monitoring at 450 nm. The major product is purified by preparative RPHPLC using a preparative column with the same gradient as for analytical monitoring, but run at 3 mL/min over 1 hr. Product fraction is neutralized with minimum saturated $NaHCO_3$ then rotovaped dry.

DMF. After 30 min tetramethylrhodamine cadaverine (Rh) (Molecular Probes, Eugene Oreg., cat. #A1318, 10 mg, 0.019 mmol) is dissolved in 1 mL dry DMF and the solution added to the NIDAC/BOP reaction mixture. The reaction is followed by RPHPLC using a gradient from 20 to 70% B in 14 minutes, monitored at 540 nm (background set at 450 nm). The rhodamine reagent is a mixture of isomers with the carboxamide either as drawn or at the position indicated by the arrow (Molecular Probes catalog), which appear at 9 and 11 min. New peaks containing the rhodamine chromophore appear very slowly at 15.5 and 16 min. The reaction is allowed to proceed 11 days.

The main product peaks are purified by preparative RPHPLC, neutralized with minimum saturated $NaHCO_3$, evaporated to dryness under reduced pressure, taken up in

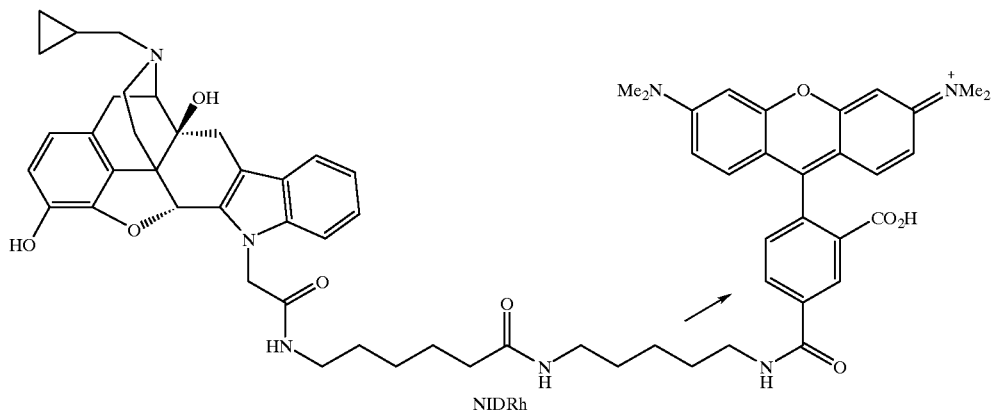

NIDRh

Example 14

(NID-Rh)

NIDAC as isolated in Example 12 (13.6 mg, 0.023 mmol), BOP (9.6 mg, 0.022 mmol) and ethyldiisoproplyamine (33 mL, 0.19 mmol) are combined in 2 mL dry MeOH for transfer to tared vessels and weighed. Yield of isomer A is 3 mg, isomer B is 4 mg. RPHPLC analysis of the isolated products indicates that they are pure with respect to UV/vis.-active materials. FAB MS of the isolated product fraction gives the expected molecular ion ($C_{64}H_{72}N_7O_9$, 1082).

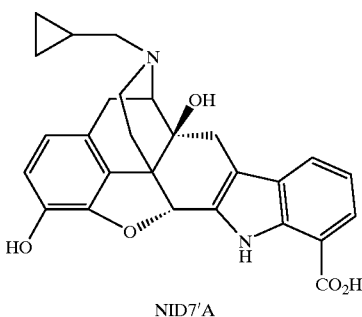

NID7'A

Example 15

7'carboxy naltrindole (NID7'A)

Method adapted from Portoghese et al., "7'-Substituted Amino Acid Conjugates of Naltrindole. Hydrophilic Groups as Determinants of Selective Antagonism of d-$_1$ Opioid Receptor-Mediated Antinociception in Mice," *J. Med. Chem.* 38:402–7, 1995.

Naltrexone hydrochloride (Sigma; 1.0508 g, 2.78 mmol) and 2-hydrazinobenzoic acid (Aldrich; 0.6312 g, 3.33 mmol) are mixed in a flask. Acetic acid (25 mL) is added and the reaction flask is capped with a water cooled condenser and heated to reflux in an oil bath. The reaction is followed by RPHPLC and stopped after refluxing overnight. The major new peak elutes at 13.6 min in a 14 min gradient from 20 to 70%B and shows a $\lambda_{max}$ shifted from that of naltrindole (280 nm) to about 312 nm. The reaction mixture is evaporated to dryness under reduced pressure, then taken up in 20% MeCN with 0.1% TFA and applied to a C18 flash column equilibrated in the same solvent. The column is eluted with a step gradient consisting of 250 mL each of 20, 30, and 40% MeCN each containing 0.1% TFA. The main reaction product precipitates as a white powder from the main product containing fractions, and is filtered and transferred to a tared vial. Isolation of residual product in the fraction filtrates yields little additional product. Total reaction yield is 33%. The $^1$H NMR spectrum (CD$_3$OD) shows signals characteristic of the desired product: C5 methine, 5.7 ppm, doublets at 7.4 and 7.8 for C4' and C6', and a triplet at 6.9 ppm for C5'. Low resolution ESI MS gives the expected M+H ion (C$_{27}$H$_{26}$N$_2$O$_5$+H) at 459.

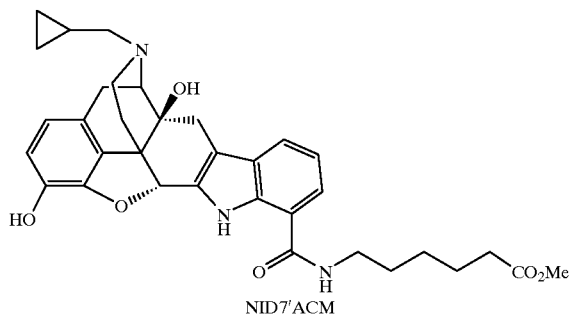

NID7'ACM

Example 16

(NID7'ACM)

NTD7'A (199.6 mg, 0.44 mmol), BOP (229.3 mg, 0.48 mmol), and ethyl-6-aminocaproate (101.7 mg, 0.55 mmol) are mixed in 6.5 mL dry DMF, followed by ethyl diisopropylamine (0.75 mL, 4.4 mmol). The reaction is monitored by RPHPLC using a 14 min gradient from 20 to 70% B. Reaction is allowed to continue overnight, after which NID7'AC is consumed and two new peaks are seen in a ratio of ~6:1. The reaction mixture is quenched by the addition of 1 mL of water, then stirred 10 min. The mixture is then evaporated under reduced pressure before being taken up in EtOAc/H$_2$O. The aqueous phase is made basic by addition of dilute NaOH and the EtOAc phase washed 2× with dilute aqueous NaOH. The EtOAc phase is then extracted with 0.5 M citric acid and the acid solution washed 3× with EtOAc. The citric acid solution is made basic by addition of saturated NaHCO$_3$ and finally NaOH while being extracted with EtOAc. The EtOAc solution was evaporated to dryness under reduced pressure. The residue was applied in equilibration solvent to a Silica flash column equilibrated in 1% MeOH, 2% Et$_3$N/CH$_2$Cl$_2$ and eluted with 500 mL of equilibration solvent. Product containing fractions were identified by UV absorbance and shown by TLC to be a single spot. Fractions were pooled, washed with water, then evaporated to dryness under reduced pressure. The $^1$H NMR spectrum shows the expected changes from the spectrum of NID7'A: multi-proton multiplets at δ=1.4, 1.7 and 2.3 ppm and a 3 proton singlet at 3.7 ppm. The $^{13}$C NMR spectrum is assignable by referring to the spectrum for Bzl-NIDACM (Example 4). ESI MS gives the expected nominal mass for the M+H ion (C$_{34}$H$_{39}$N$_3$O$_6$+H)=586.

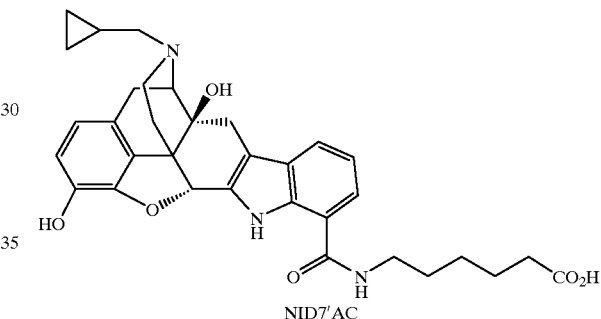

NID7'AC

Example 17 (NIDAC)

NID7'ACM produced in Example 16 is taken up in 8 mL MeOH (dissolution difficult) and treated with 1 mL 1 N NaOH. After stirring overnight, RPHPLC shows the reaction to be about 70% complete. Additional 1 N NaOH (0.5 mL) is added and the mixture stirred overnight again. The solution is then neutralized with minimum 1 M HCl, then evaporated under reduced pressure. Evaporation is stopped when a white precipitate coats the flask and a small aqueous volume remains. The liquid is manually removed and the product remains. $^1$H NMR (CD$_3$OD) indicates that the product has the desired structure. ESI MS gives the expected nominal mass for the M+H ion (C$_{33}$H$_{37}$N$_3$O$_6$+H)=572.

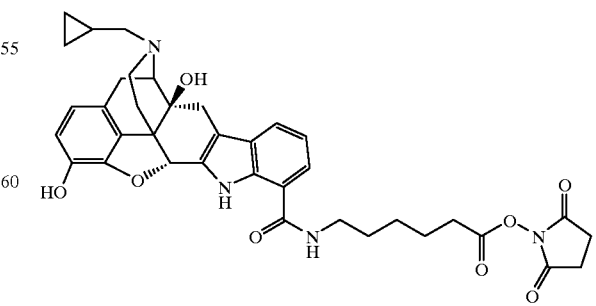

NID7'ACNHS

Example 18

(NID7'AC-NHS)

NID7'AC (200 mg, 0.35 mmol), N-hydroxysuccinimide (NHS; 60 mg, 0.52 mmol) and dicyclohexylcarbodiimide (DCC; 108 mg, 0.52 mmol) are mixed in 3 mL dry DMF.

4% triethylamine. Product containing fractions are identified by TLC and RPHPLC, and are pooled and evaporated under reduced pressure. Residual triethylamine is removed by repeatedly adding MeCN to the residue and re-evaporating until triethylamine signals are no longer visible in the $^1$H NMR spectrum.

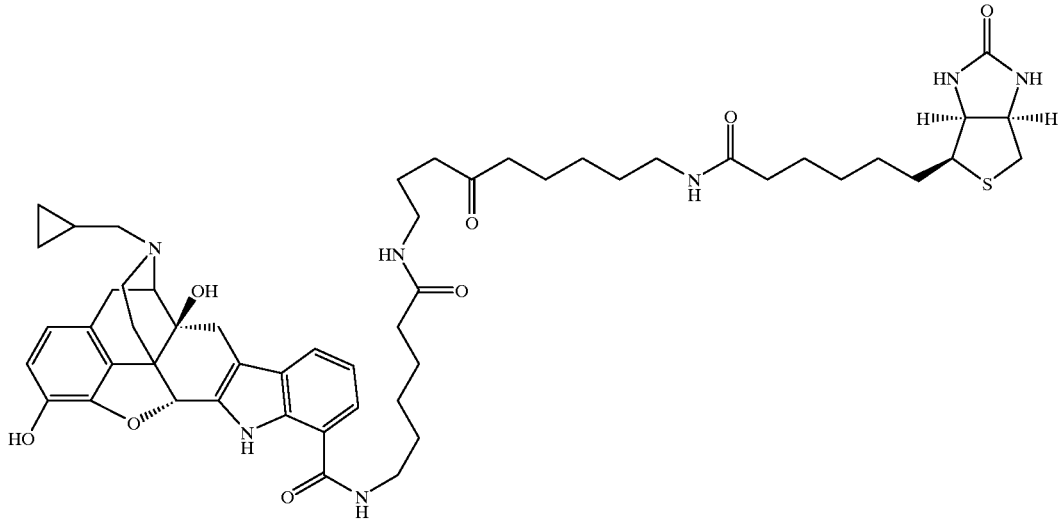

The reaction is followed by RPHPLC using a 14 min gradient from 20 to 70% B. After stirring overnight the reaction mixture is filtered, the filtrate evaporated to dryness and applied to a Silica column equilibrated in $CH_2Cl_2$ containing 2% triethylamine, then eluted with a step gradient consisting of 1, 2, 5, 10% isopropanol in $CH_2Cl_2$, each containing 2% triethylamine. Product containing fractions are identified by TLC and RPHPLC, and are evaporated to dryness under reduced pressure.

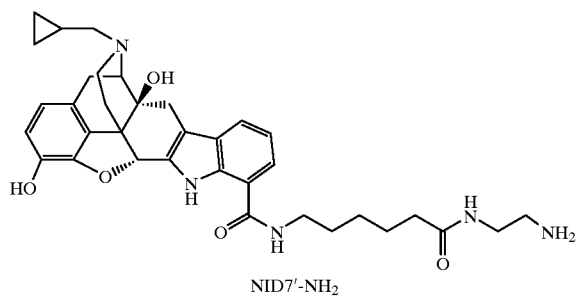

NID7'-NH$_2$

Example 19

(NID7'-NH$_2$)

NID7'AC-NHS (200 mg, 0.3 mmol) is dissolved in 4 mL dry DMF containing ethylene diamine (0.40 mL, 6 mmol). The reaction is stirred at room temperature and monitored by RPHPLC using a gradient from 20 to 70%B in 14 min. After stirring overnight the reaction is complete. It is evaporated to dryness under reduced pressure and purified on a Silica flash column equilibrated in 1% MeOH in $CH_2Cl_2$ containing 4% triethylamine, then eluted with a step gradient consisting of 2, 3, 5, 10% MeOH in $CH_2Cl_2$, each containing

Example 20

(NID7'-biotin)

NID7'-NH$_2$ (123 mg, 0.20 mmol) is stirred with biotinamidocaproate N-hydroxysuccinimide ester (Sigma; 100 mg, 0.22 mmol) in 4 mL dry DMF. The reaction is monitored by RPHPLC using a gradient from 40 to 100% B in 18 min. A new peak appears eluting much later than NID7'-NH$_2$ but with the same UV absorbance. The product is purified by flash chromatography on Silica using MeOH in $CH_2Cl_2$ containing 4% triethylamine.

Example 21

NID-streptavidin

NID7'AC-NHS (5 mg, 7.5 mmol) is dissolved in 2.0 mL dry DMSO. A solution of streptavidin (SA) is prepared at 10 mg/mL in 50 mmol sodium borate buffer, pH 8.0.

To 2.0 mL of the SA solution (0.38 mmol SA) is added 0.2 mL of the NID7'AC-NHS solution. The reaction is left on a shaker for 4 hours at room temperature. The conjugate is then concentrated in a centrifugal concentration device and separated from residual NID components by elution through a desalting column. The conjugate is analyzed by UV spectroscopy and by ESI MS.

Example 22

Delta-Opioid Receptor Binding of NIDDOTA1 and NID Rh

The assay determines the concentration of test compound capable of inhibiting the specific binding of $^3$H NID to the plasma membrane of an intact cell. To do so, 1 to 4 serial dilutions of test compounds and naltrindole (NID, Sigma) are prepared to generate solutions with concentrations ranging from $10^{-3}$ to $10^{-14}$ M in 50 mM Tris buffer, pH 7.5. $^3$H NID (American Radiolabeled Chemicals, St. Louis, Mo., specific activity 49 dpm/$10^{-15}$ mol) is prepared in Tris at a concentration of $10^{-9}$ M. Cultured cells of the neruablastoma/glioblastoma hybrid cell line NG108-15 (American Type Culture Collection) are briefly trypsinized, washed with media, and resuspended at $6\times10^5$ cells/mL. 20 µL of test compound or NID solution and 20 µL of $^3$H NID are added to each of 96 wells of a Multiscreen assay system (Millipore) MAFB. 160 µL of cell suspension in Dulbecco's MEM+HAT with 10% Fetal Bovine Serum are added. The reactions are allowed to equilibrate 2 hr at 37° C., vacuum filtered, washed 2× with 200 µL ice cold Tris buffer and air dried. The filters are punched out of the plate into scintillation vials and mixed on a shaker overnight before counting.

Data is analyzed by the Prism software package (GraphPad Software, Inc., San Diego, Calif.) using a nonlinear curve fit routine for one site competitive binding. The Software generates plots of bound counts vs. log molar concentration of inhibitor and determines values for Log $EC_{50}$ (and associated uncertainty) that best fit the data. The values in Table 1 show that NID-DOTA is only about 3-fold lower in affinity than NID and NID-Rh is only about 9-fold lower in affinity than NID.

TABLE 1

| Test # | Compound | Log $EC_{80}$ (±S.E.) | $EC_{50}$ (M) | Test/Control |
|---|---|---|---|---|
| 1 | NID | −8.4 ± 0.4 | $4.2 \times 10^{-9}$ | |
| 1 | NID-DOTA | −7.9 ± 0.2 | $1.2 \times 10^{-8}$ | 2.8 |
| 2 | NID | −8.8 ± 0.1 | $1.8 \times 10^{-9}$ | |
| 2 | NID-Rh | −7.8 ± 0.1 | $1.6 \times 10^{-8}$ | 8.9 |

Example 23

Figure 3A:
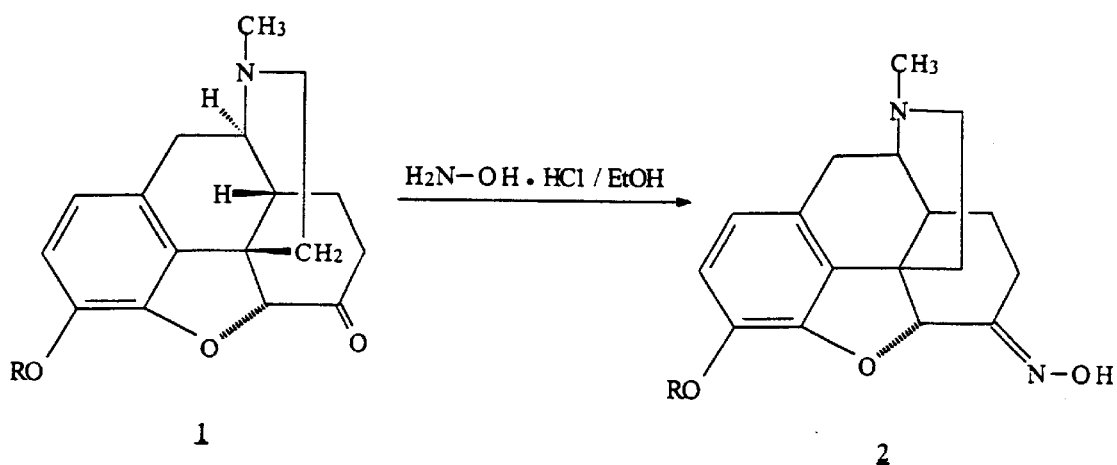
FIGS. 3A and 3B illustrate synthetic methodology for preparing a compound of the present invention.
Figure 3A:
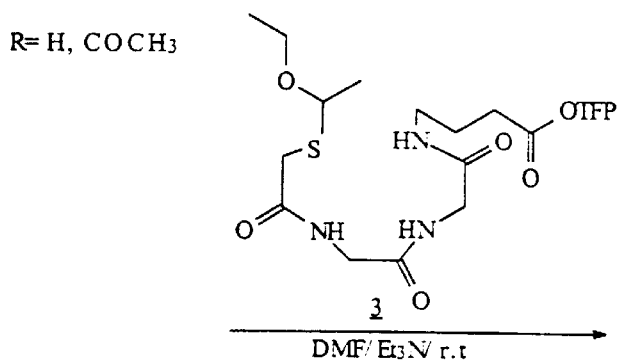
Figure 3A:
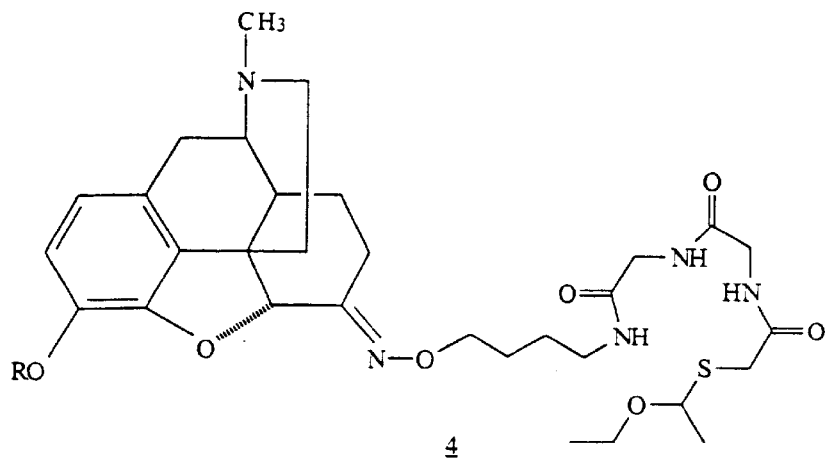

As described in FIG. 3A, one equivalent of keto compound 1 is reacted with 1.2–2.0 equivalents of hydroxylamine hydrochloride in ethanol. The reaction mixture is heated under reflux to form the oxime, compound 2 in good yield. The oxime, compound 2 is reacted with compound 3 in 0.2 molar excess in DMF solvent using 5.0 molar excess of triethylamine. The reaction mixture is stirred at room temperature (r.t.). The progress of the reaction is monitored by TLC. The crude product is purified by silica gel chromatography using ethylacetate initially and finally with methanol/EtOAc as eluting solvents. Fractions containing the product are combined and the solvent removed under reduced pressure and dried under high vacuum to yield compound 4 in good yield.

Example 24

Figure 3B:
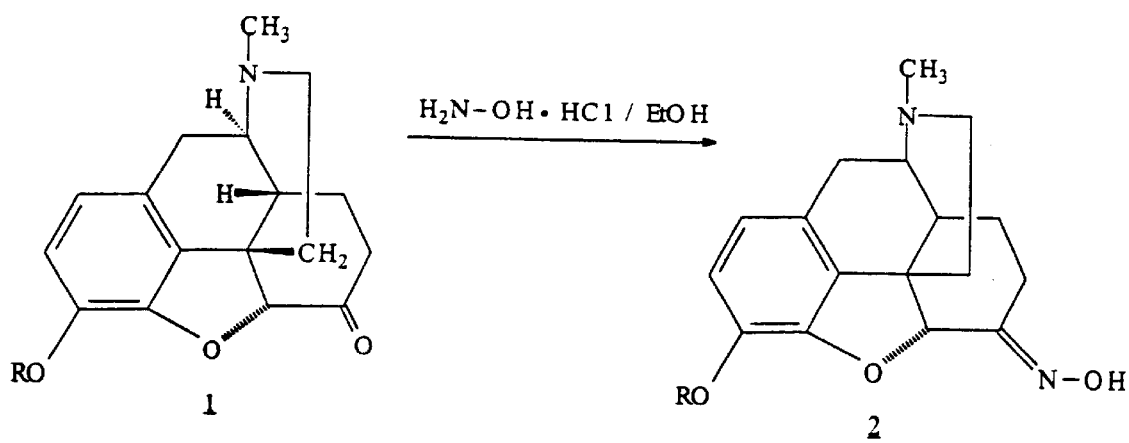
Figure 3B:
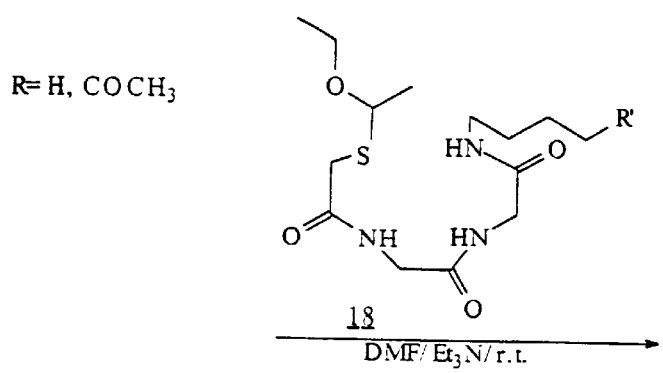
Figure 3B:
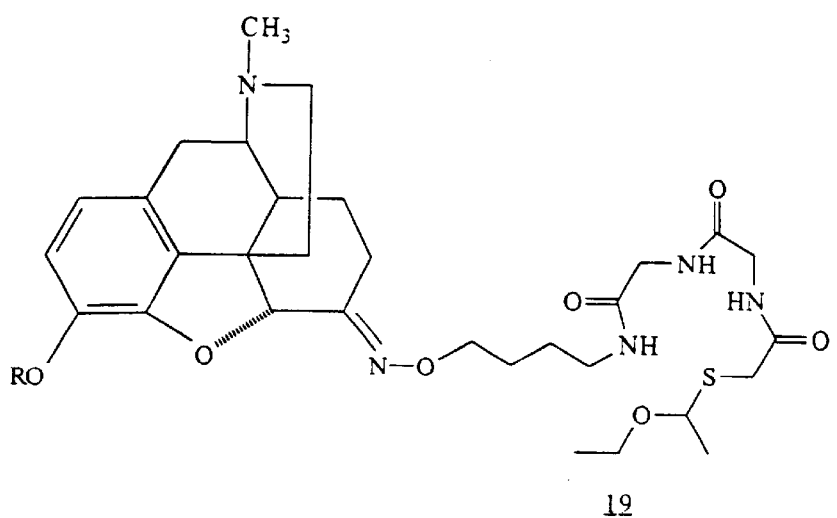

In analogy with Example 24 and as illustrated in FIG. 3B, oxime, compound 2 is reacted with compound 18 in its chloride, mesylate or tosylate form. In FIG. 3B, R' represents any of chloride, —O—$SO_2$—$CH_3$ or —O—$SO_2$—Ar—$CH_3$. 0.2 excess equivalents of compound 18 are reacted in anhydrous DMF solvent using 5.0 equivalents of triethylamine at room temperature. The progress of the reaction is monitored by TLC. After completion of the reaction, the crude product is purified by silica gel column chromatography using ethyl acetate and MeOH/$CH_2Cl_2$ as eluting solvents. Fractions containing the product are pooled and the solvent removed under reduced pressure and dried to yield compound 19 as an oxime ether in good yield.

Example 25

Figure 4A:
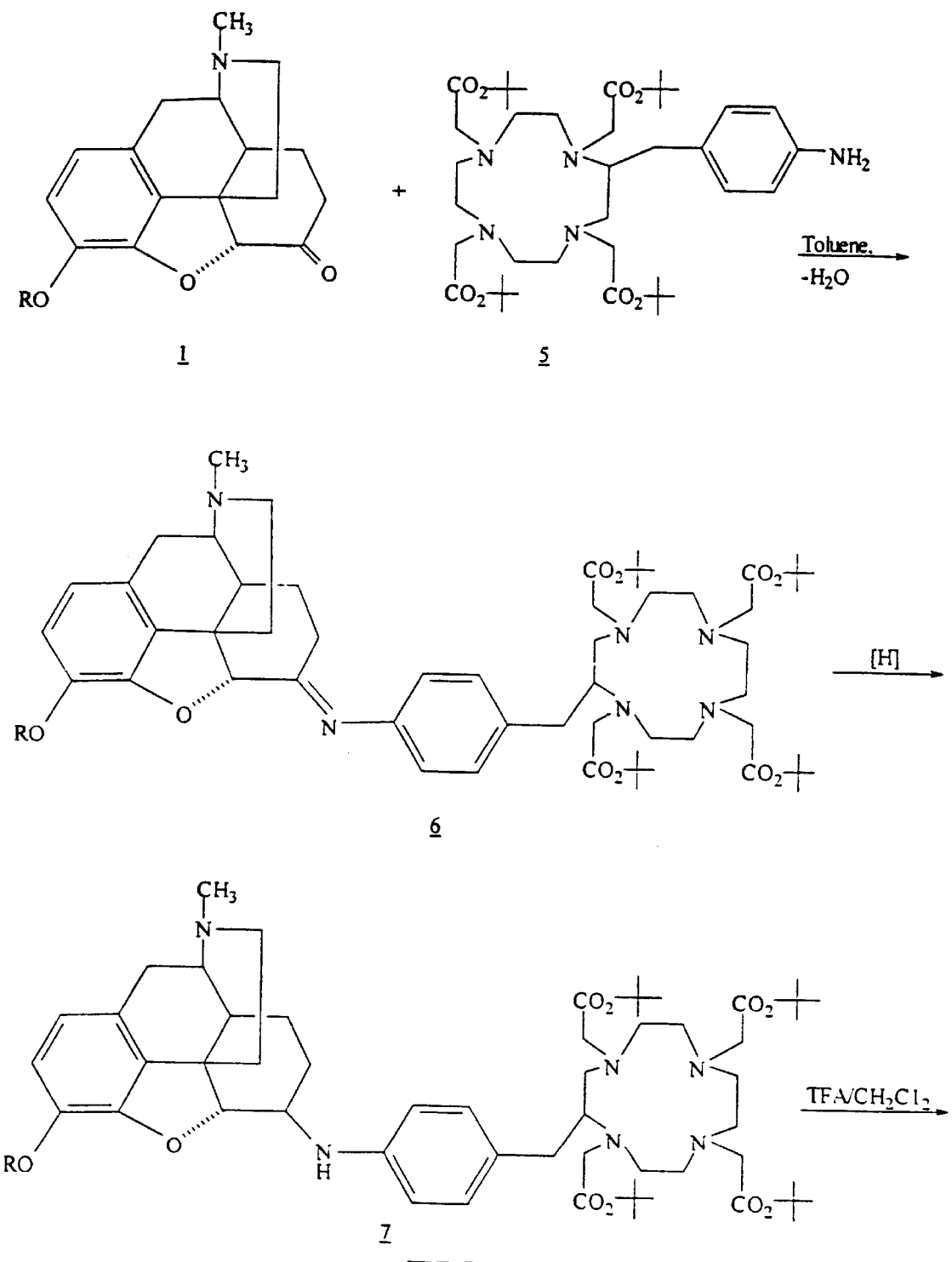
FIGS. 4A and 4B illustrate synthetic methodology for preparing a compound of the present invention.
Figure 4B:
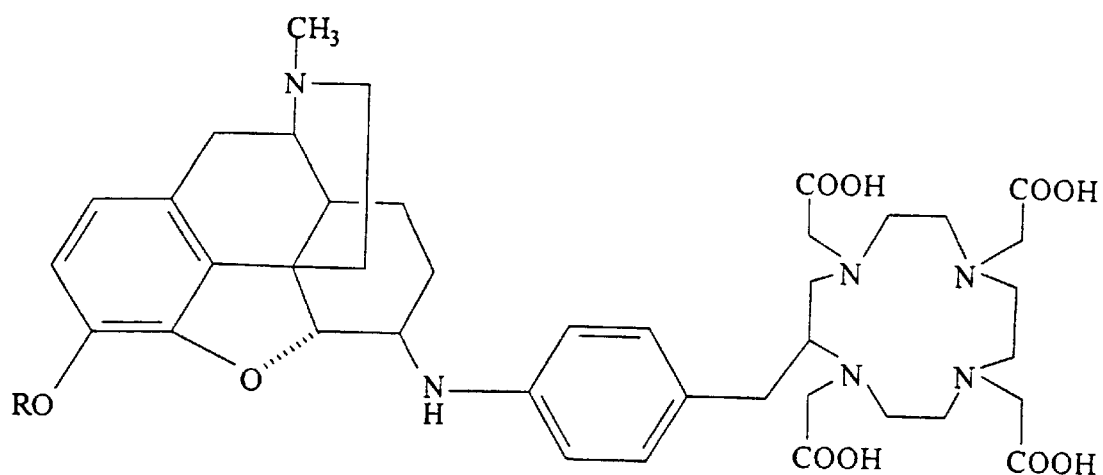

As described in FIGS. 4A and 4B, excess of p-aminobenzyl DOTA having its carboxylic acids protected as tertiary butyl esters (compound 5) is reacted with the keto analog, compound 1. The reaction mixture is heated under reflux in toluene using molecular sieves to absorb water or Dean's stork apparatus for azeotropic distillation of water formed in the reaction mixture. The progress of the reaction is monitored by TLC. After completion of the reaction, solvent from the reaction mixture is removed under reduced pressure and dried. The crude product is purified by florisil silica gel column chromatography using ethyl acetate/ligroine as eluting solvents. Fractions containing the product are combined and solvent removed under reduced pressure and dried to yield. Compound 6 is provided in moderate yield.

Compound 6 is then catalytically reduced using 10% Palladium over activated carbon in ethanol solvent. The reduction of imine to an amine is carried out in a Parr hydrogenation apparatus at 50–60 PSI (pounds per square inch). The reaction mixture is filtered. Solvent from the filtrate is removed under reduced pressure and the residue is dried under high vacuum to provide the crude product 7.

The crude product 7 is used in next reaction without further purification. The tertiary butyl esters of the carboxylic acid functional group protecting groups are removed in 50% trifluoroacetic acid-methylene chloride reagent. The reaction mixture is stirred at room temperature overnight. Solvent from the reaction mixture is removed under reduced pressure and dried to yield compound 8 (see FIG. 4B) in good yield.

Example 26

Figure 5:
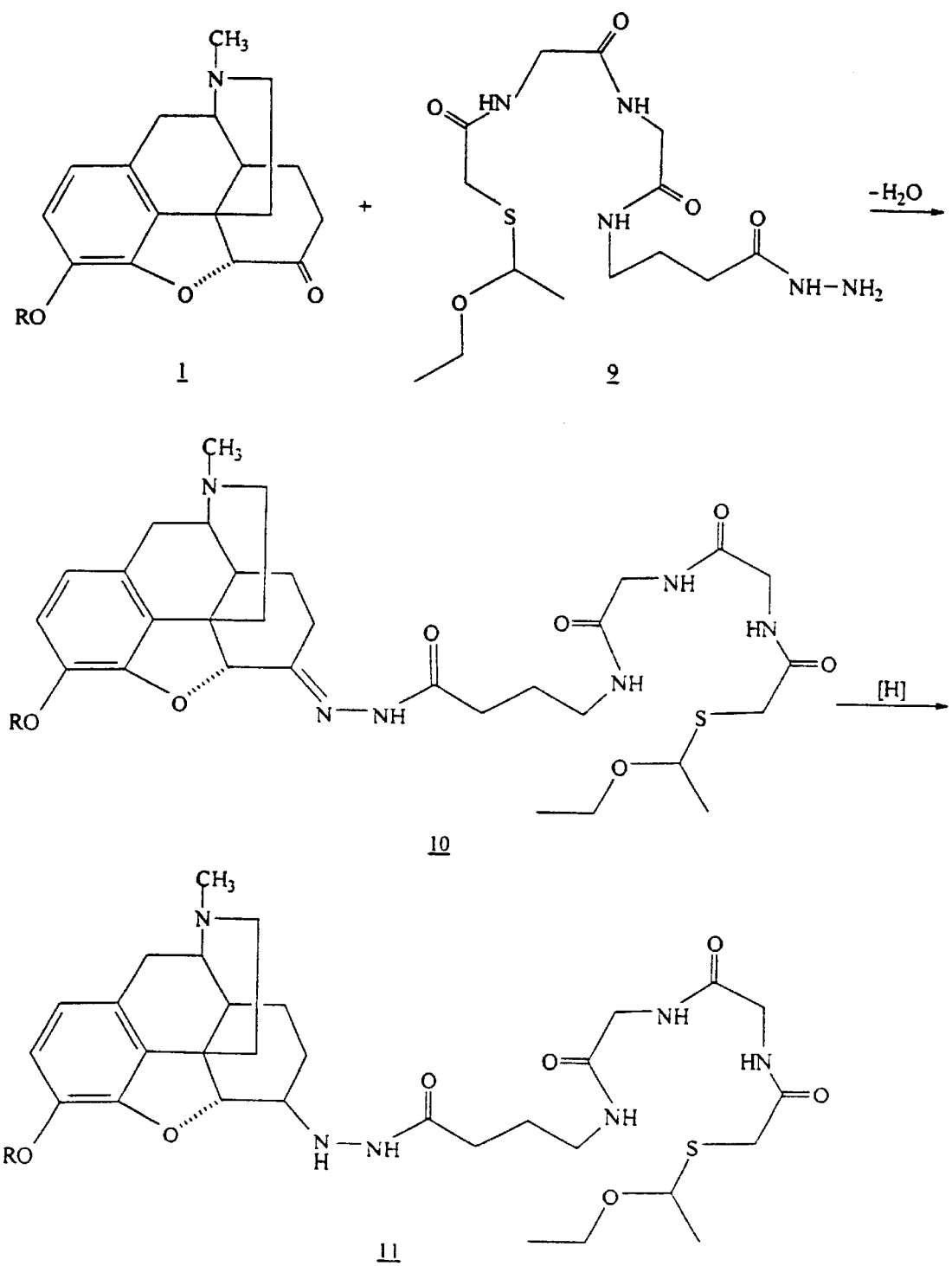
FIG. 5 illustrates synthetic methodology for preparing a compound of the present invention.

As described in FIG. 5, compound 1 is reacted with compound 9. The hydrazide derivative compound 9 (in molar excess) is stirred with compound 1 dissolved in ethanol solvent. The progress of the reaction is monitored by TLC. After completion of the reaction, solvent is removed under reduced pressure and the residue is dried under high vacuum to give crude compound 10 in good yield. The crude product is purified by florisil silica gel column chromatography using methanol/ligroin or methanol/EtOAc (EtOAc represents ethyl acetate) as elution solvents. Fractions containing the product are combined and solvent removed under reduced pressure, with the residue dried under high vacuum to yield compound 10.

The hydrazone derivative, compound 10 is reduced using 10% Palladium on activated carbon. Compound 10 is taken into a hydrogenation bottle, ethanol is added followed by 10% Pd/C. The catalytic reduction is carried out using a Parr hydrogenation apparatus using hydrogen at 50–60 PSI for 24 hours. The reaction mixture is filtered and the solvent removed under reduced pressure with the residue being dried under high vacuum to yield compound 11 in good yield.

Example 27

Figure 6A:
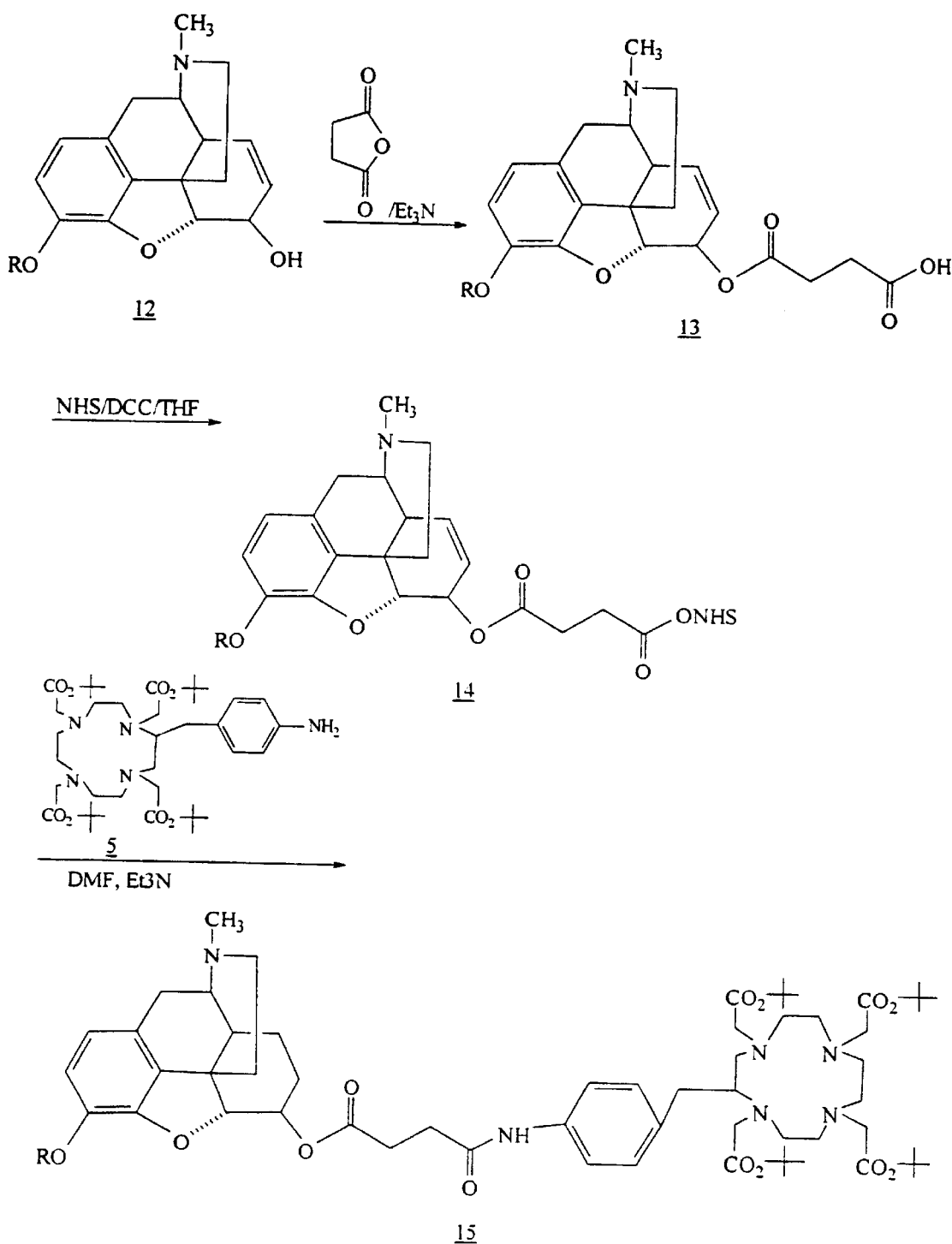
FIGS. 6A and 6B illustrate synthetic methodology for preparing a compound of the present invention.
Figure 6B:
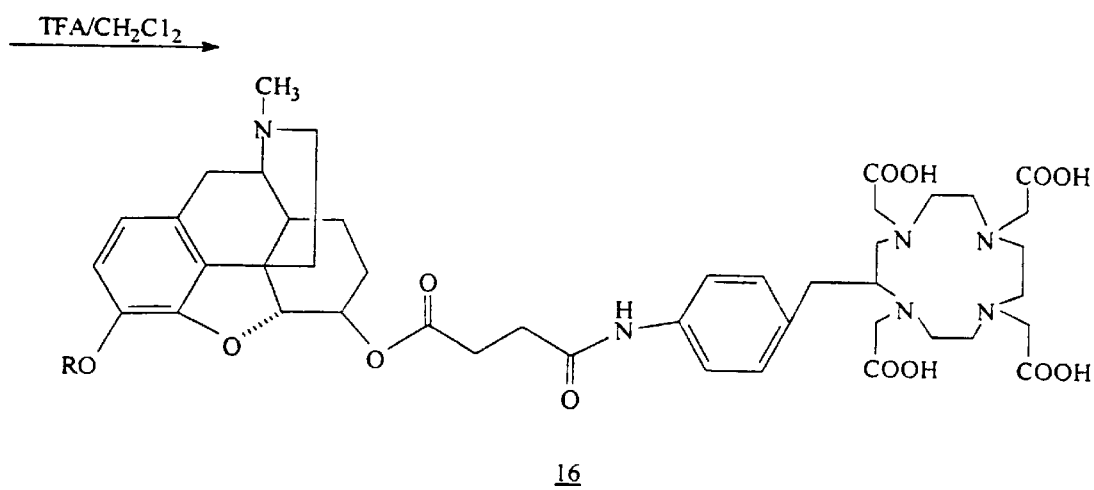

As described in FIGS. 6A and 6B, compound 12 in DMF is reacted with 1.2 equivalents of succinic anhydride and 5.0 equivalents of triethylamine. The hemisuccinic acid derivative, compound 13 is purified by silica gel column chromatography. The hemisuccinic acid is then esterified with N-hydroxysuccinimide in anhydrous THF using dicyclohexylcarbodiimide as a coupling reagent. The hemisuccinyl-NHS ester, compound 14 is then reacted with t-butyl ester analog of p-aminobenzyl DOTA, compound 5. The reaction mixture is stirred in anhydrous DMF and 5.0 equivalents of anhydrous triethylamine at room temperature. The progress of the reaction is monitored by TLC. Solvent from the reaction mixture is removed under reduced pressure and dried under high vacuum. The crude product is purified on a silica gel column chromatography using 15% $CH_3OH/CH_2Cl_2$ as elution solvent. The fractions containing the product are pooled and the solvent removed under reduced pressure, with the residue being dried under high vacuum to yield compound 15 in good yield. The compound 15 is then stirred in 50% $TFA/CH_2Cl_2$ solvent overnight at room temperature. Solvent from the reaction mixture is removed and the crude product is recrystallized from ethanol to give compound 16 in moderate yield.

Example 28

Figure 7A:
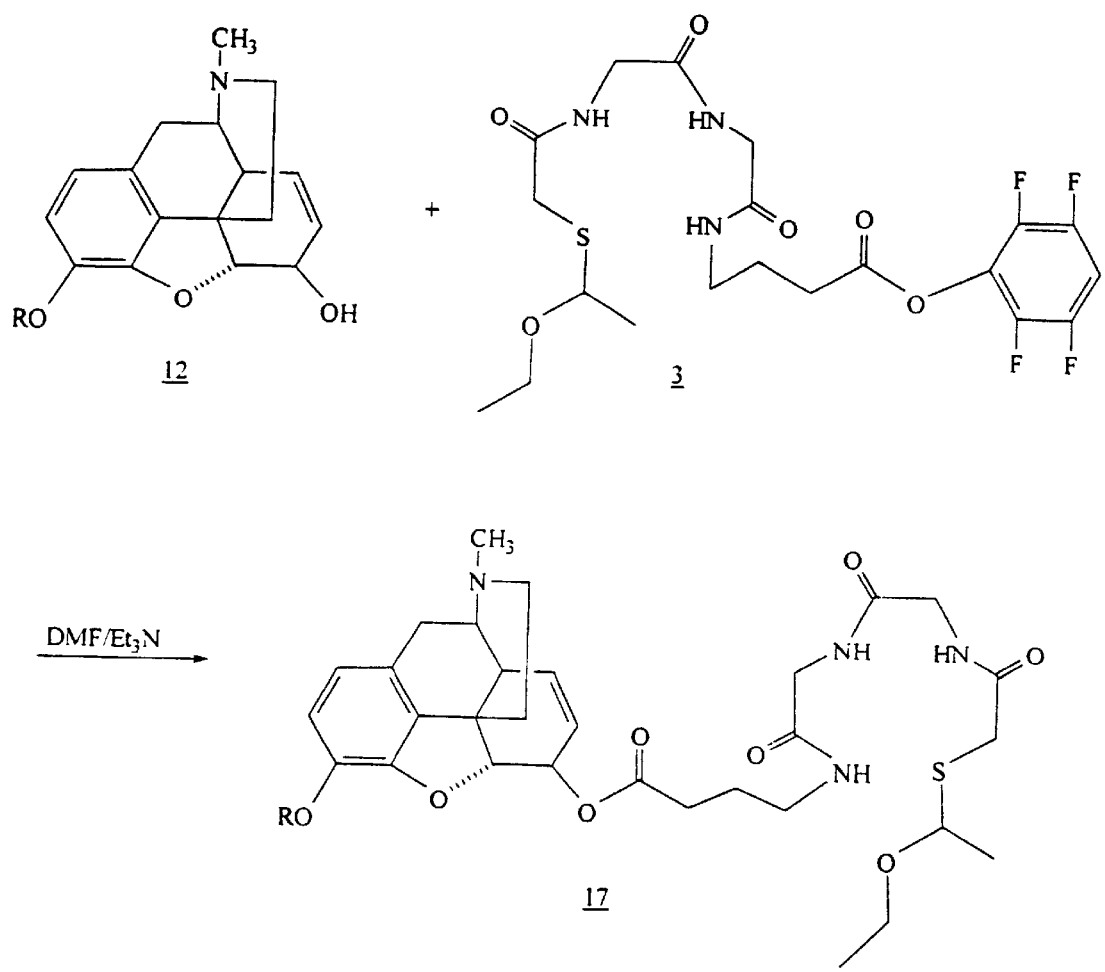
FIGS. 7A and 7B illustrate synthetic methodology for preparing a compound of the present invention.

As described in FIG. 7A, compound 12 is reacted with compound 3. The reaction mixture is dissolved in anhydrous DMF solvent. To the magnetically stirred reaction mixture, 5.0 equivalents of anhydrous tri-ethylamine is added and continued stirring at room temperature. The progress of the reaction is monitored by TLC. After completion of the reaction, solvent from the reaction mixture is removed under high vacuum. The crude product is purified on a silica gel column using 15% methanol in methylene chloride as an elution solvent. The fractions containing the product are combined and the solvent removed under reduced pressure with the residue being dried under high vacuum to yield compound 17 in good yield.

Example 29

Figure 7B:
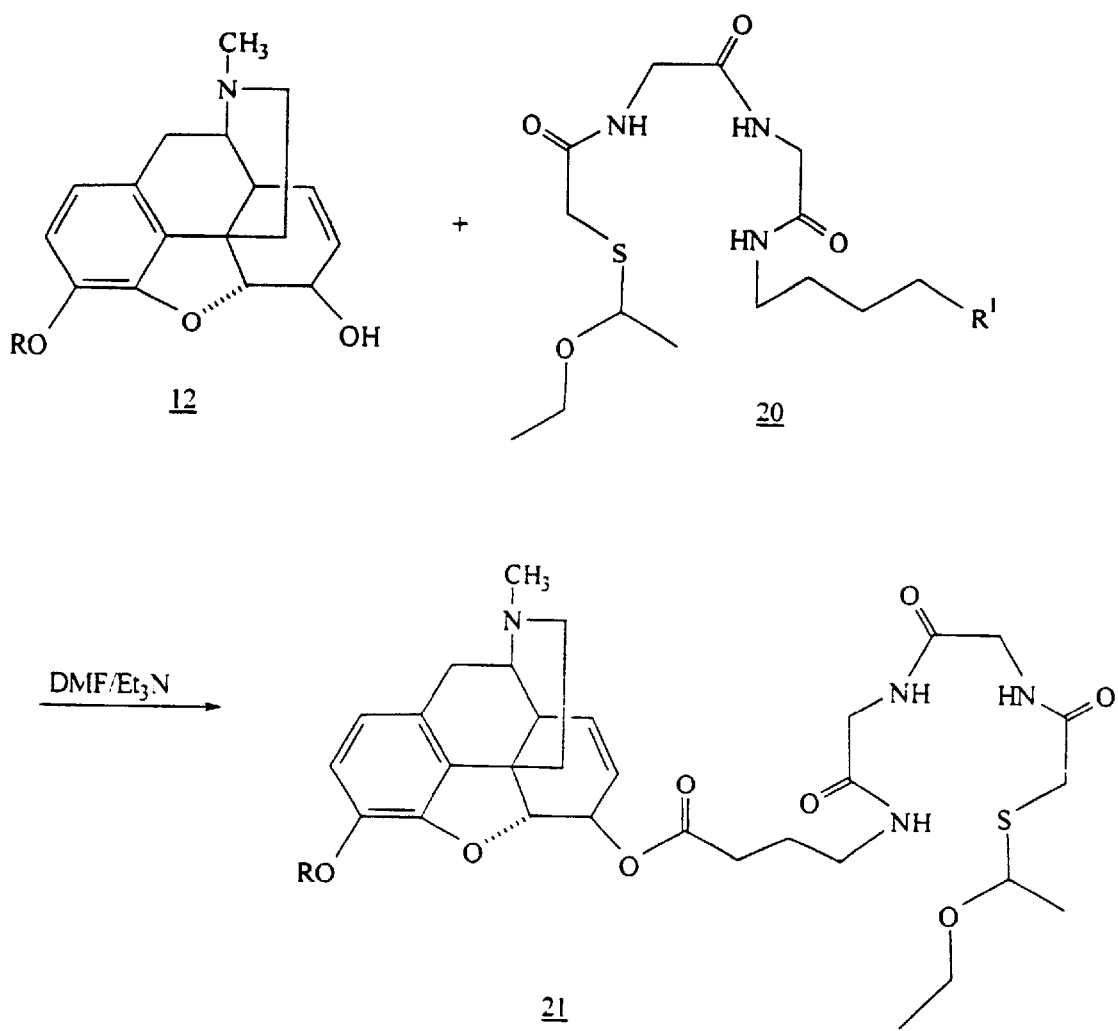
Figure 8A:
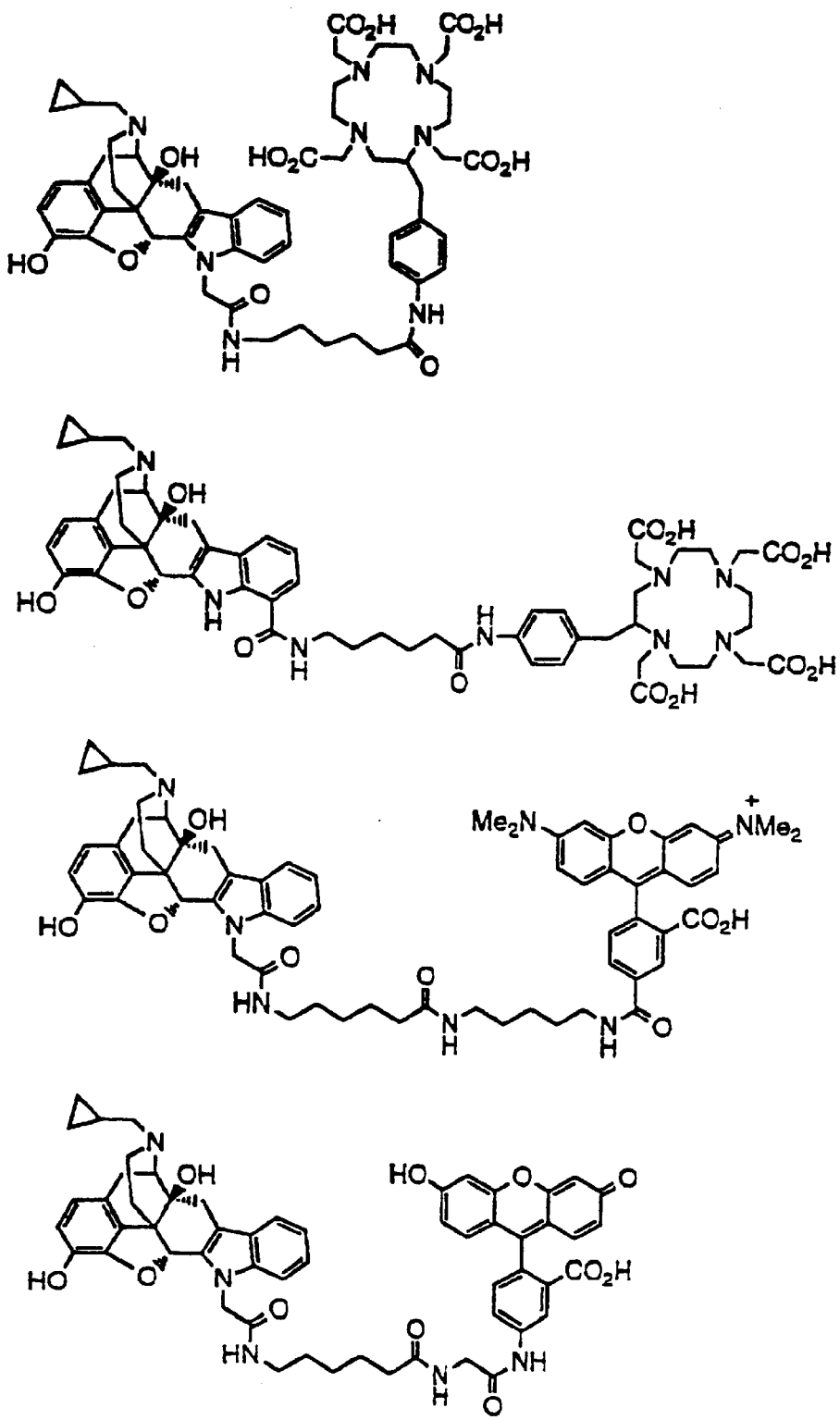
FIGS. 8A and 8B each provide chemical structures for four preferred compounds of the invention, having naltrindole-type structures for the ligand binding portions of the compounds, separated by an extender arm to various diagnostically or therapeutically effective groups.
Figure 8B:
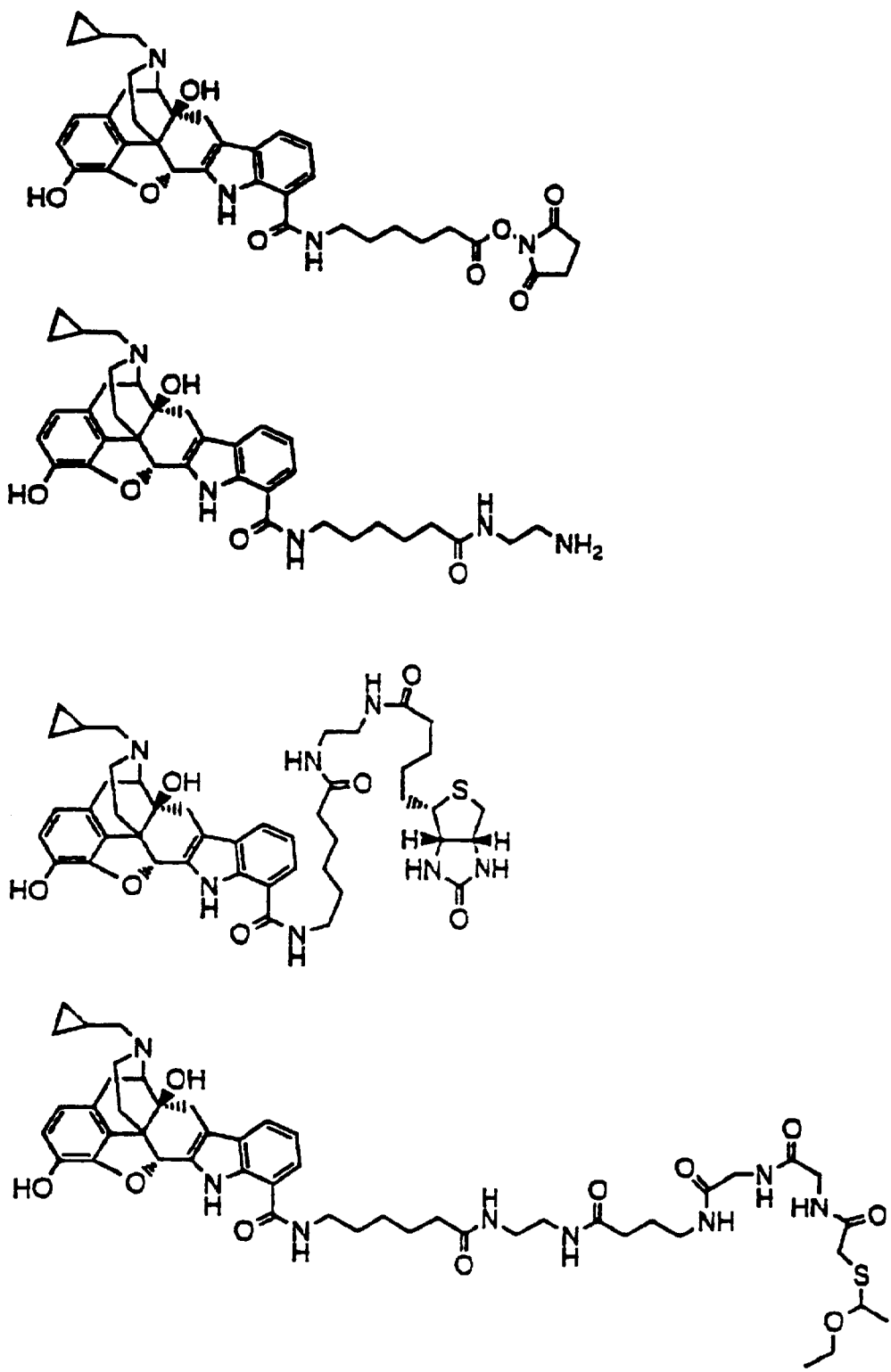
Figure 9A:
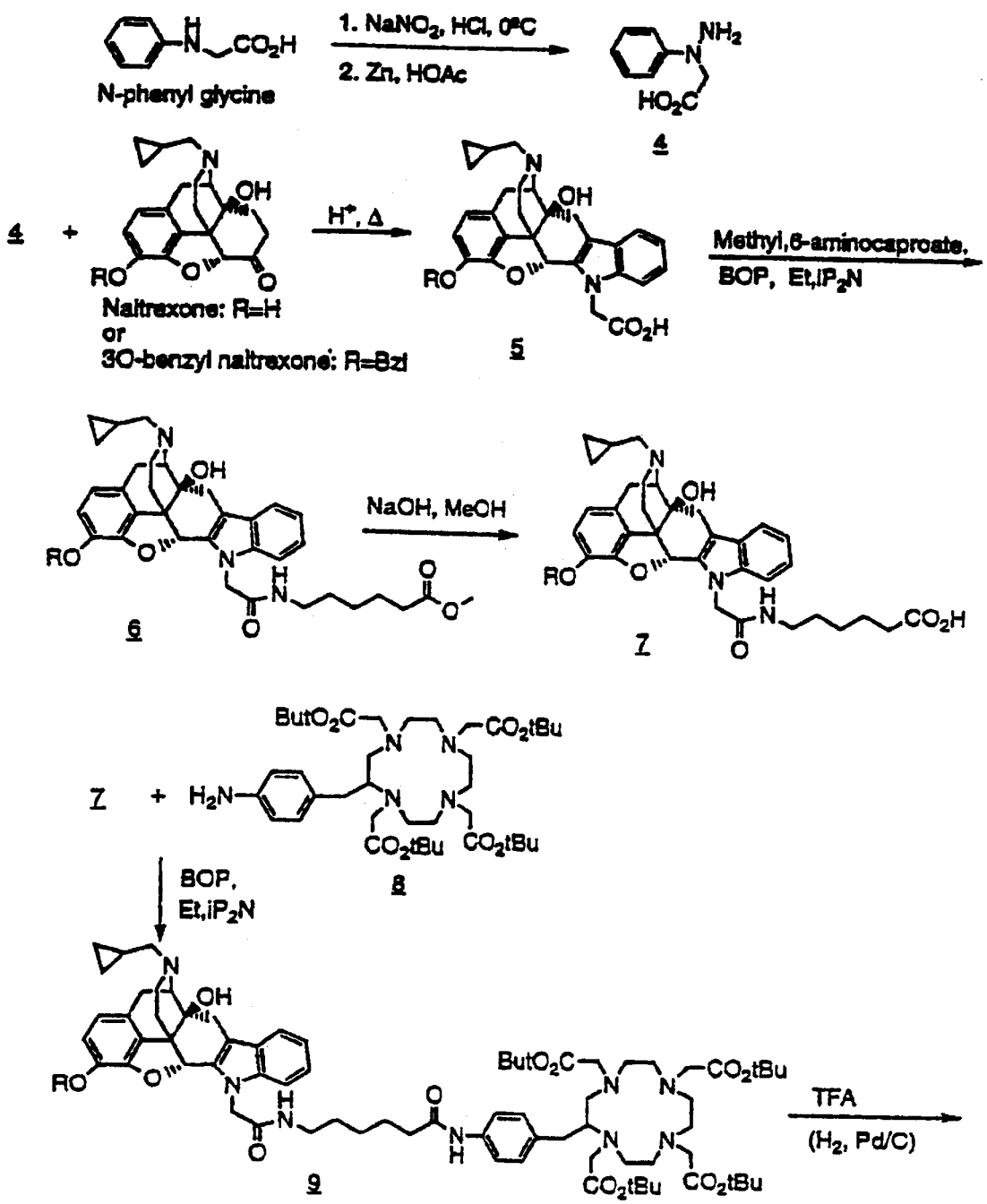
FIGS. 9A and 9B illustrate synthetic methodology for preparing a naltrindole derivative of the present invention.
Figure 9B:
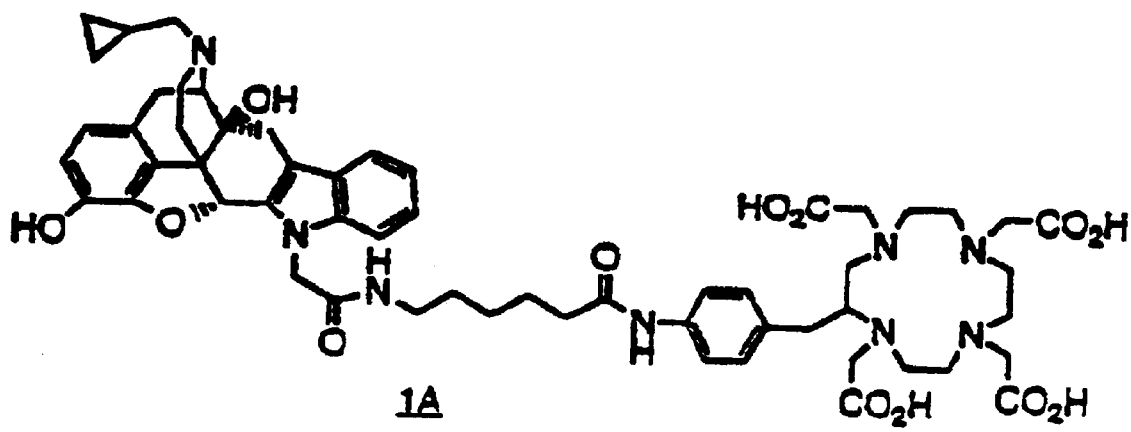
Figure 10:
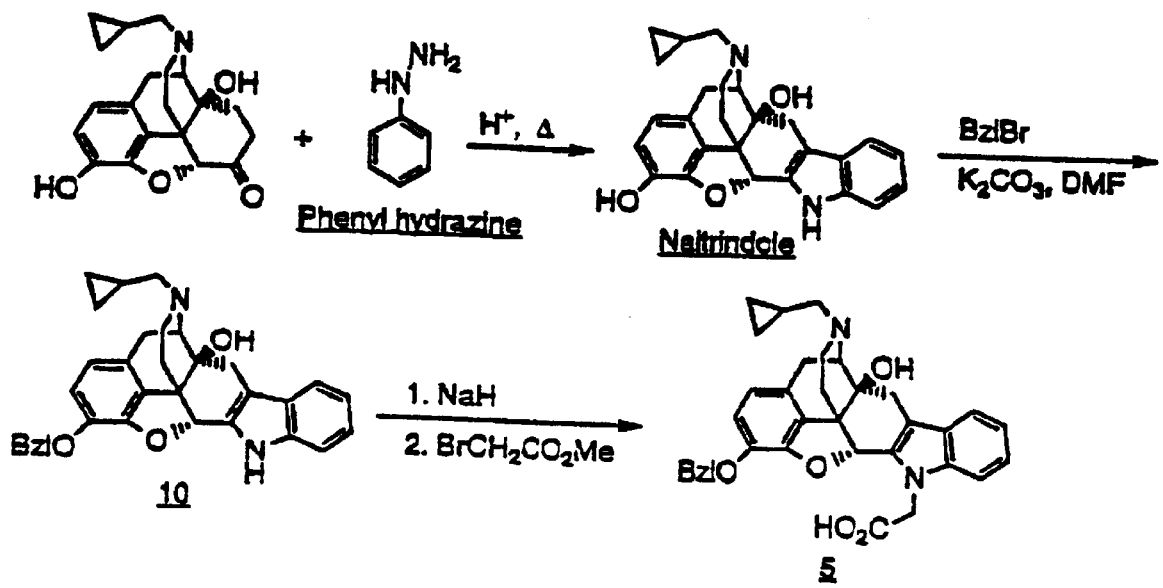
FIG. 10 illustrates synthetic methodology for preparing a naltrindole derivative having a functional group to which an extender arm and/or a diagnostically or therapeutically effective group may be added to the indole nitrogen of naltrindole.
Figure 11:
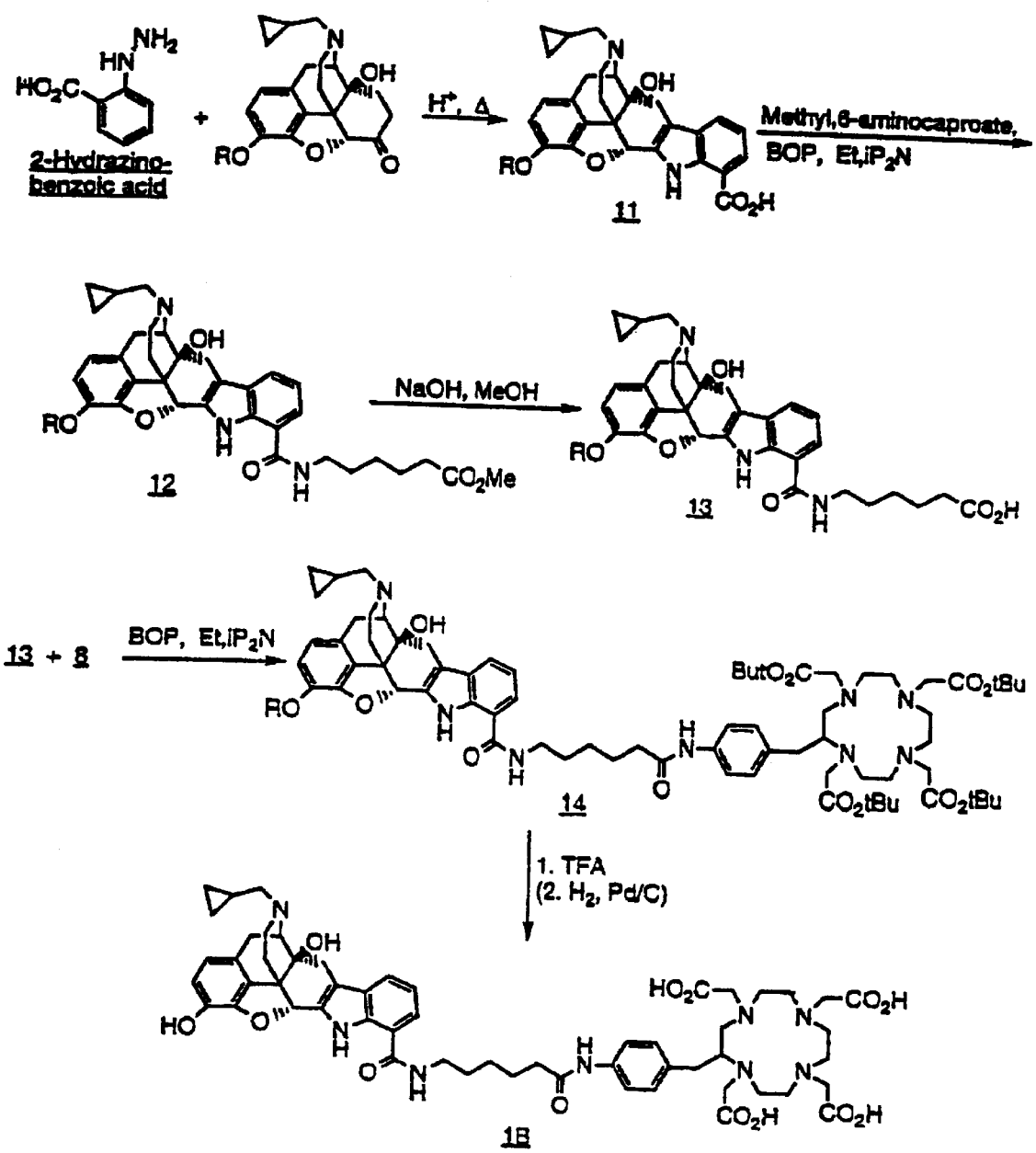
FIG. 11 illustrates synthetic methodology for preparing a naltrindole derivative having a functional group on the aromatic ring of the indole portion of the molecule, where the functional group is elaborated to an extender arm and then DOTA as a chelating agent.
Figure 12:
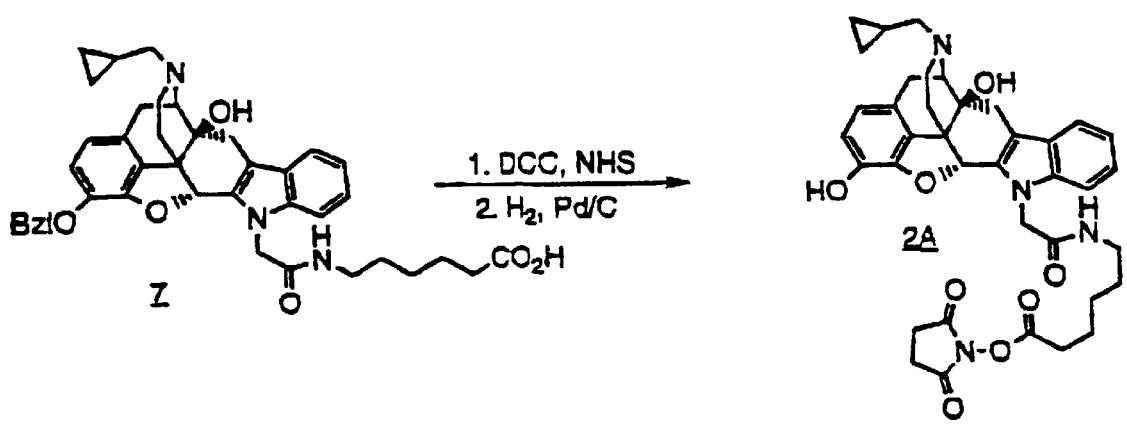
FIG. 12 illustrates synthetic methodology for adding a succinimide group to a naltrindole derivative.
Figure 13:
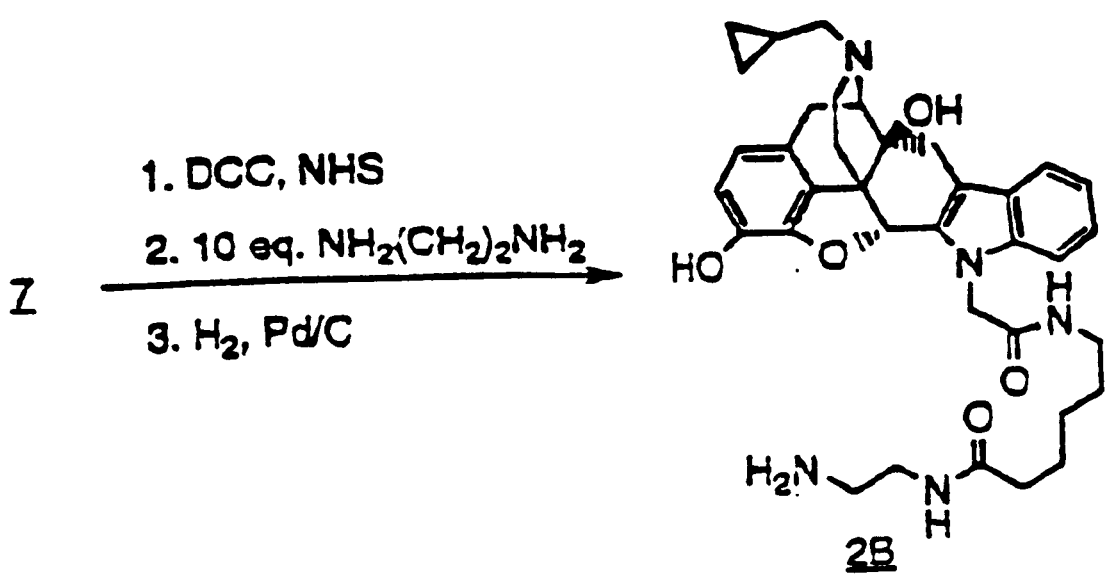
FIG. 13 illustrates synthetic methodology for adding an additional portion to an extender arm in a compound of the present invention.
Figure 14:
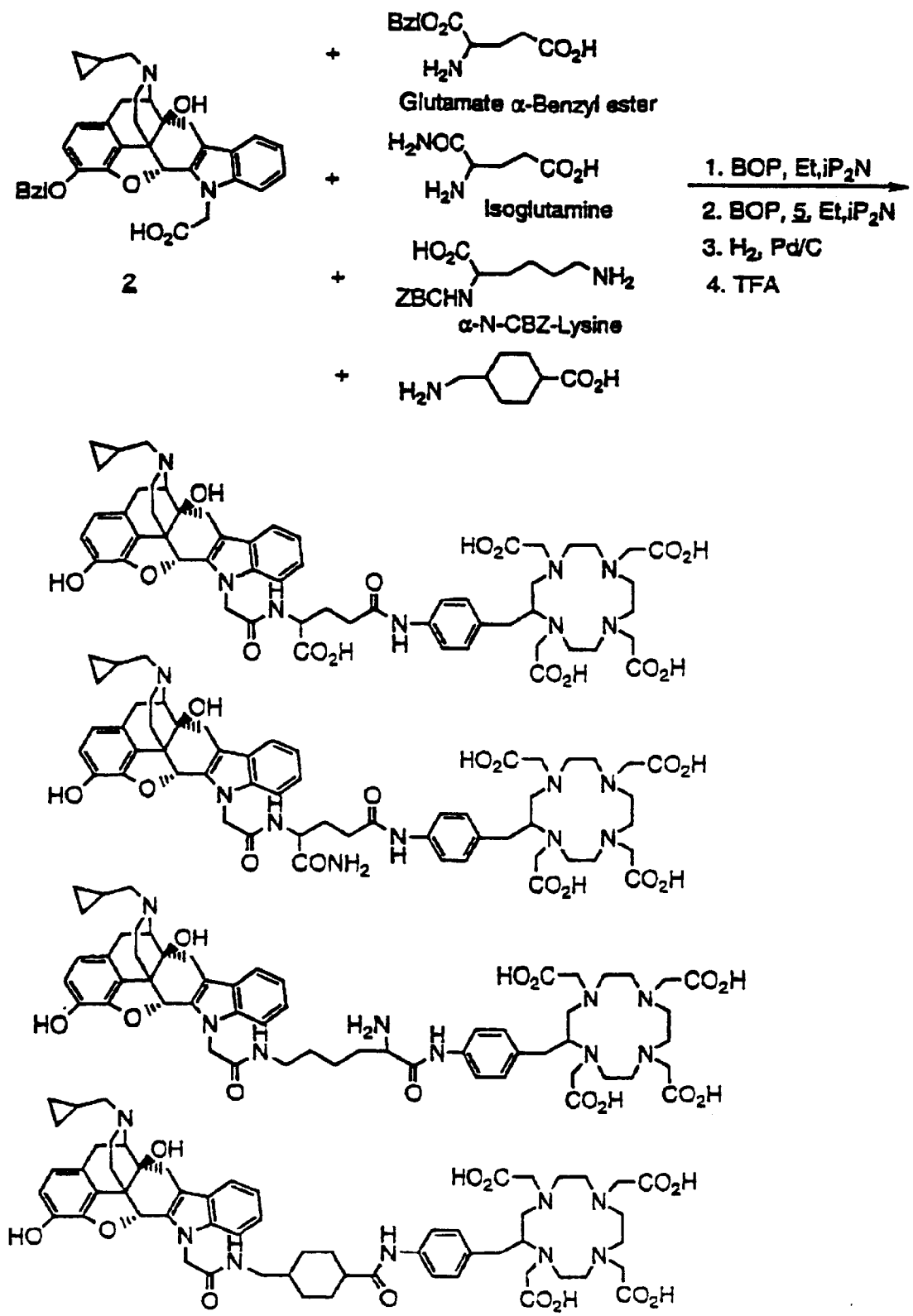
FIG. 14 illustrates synthetic methodology to add various extender arms to a naltrindole derivative, and then adding a DOTA chelating group to the end of the extender arm to provide representative compounds of the present invention.

As described in FIG. 7B, compound 12 is reacted with compound 20 in its chloride, mesylate or tosylate form. Thus, $R^1$ in FIG. 7B may be chloride, $—O—SO_2—CH_3$, or $—O—SO_2—Ar—CH_3$. The reaction mixture is dissolved in anhydrous DMF solvent. To the stirred solution, 5.0 equivalents of anhydrous triethylamine is added and stirred at room temperature. The progress of the reaction is monitored by TLC. Solvent from the reaction mixture is removed under high vacuum. The crude product is purified on a silica gel column using 15% methanol in methylene chloride as an elution solvent. The fractions containing the product are combined and the solvent removed under reduced pressure, with the residue being dried under high vacuum to yield compound 21 in good yield.

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A compound comprising a ligand portion (L) which has binding affinity for an opioid receptor, and a therapeutically or diagnostically effective group (X) selected from radionuclide chelating agents, fluorochromes, toxins, drugs, polyboron moieties, proteins, biological response modifiers, chemical moieties capable of binding to other molecules, and radioisotopes selected from therapeutically effective alpha and beta emitters, and diagnostically effective gamma emitters, wherein L has the formula

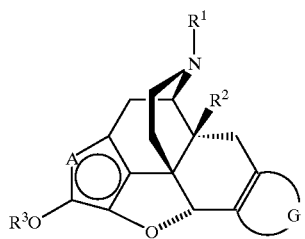

where G is selected from

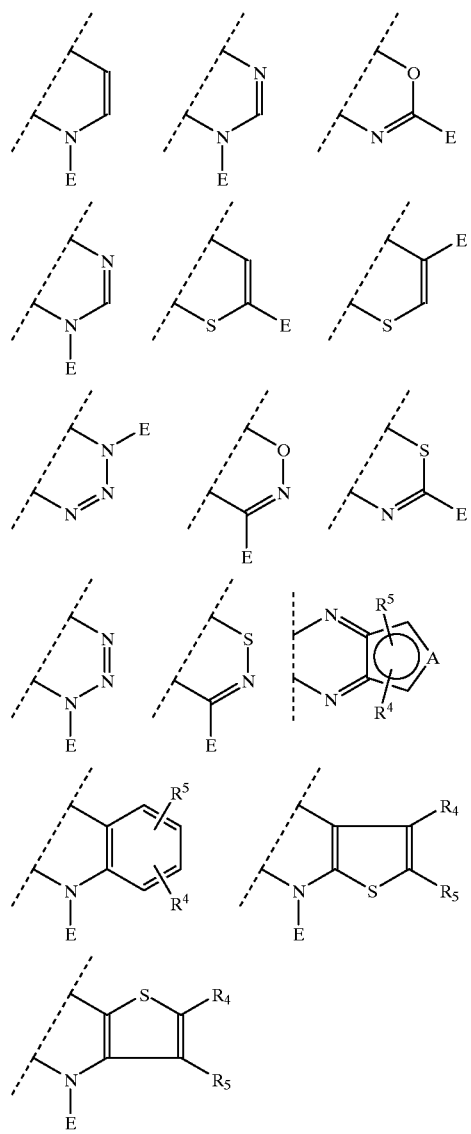

and

is a monocyclic, five- or six-membered, carbocyclic or heterocyclic, aromatic ring;

$R^1$ is selected from $(C_1-C_5)$alkyl, $(C_3-C_6$cycloalkyl)$C_1-C_5$alkylene, $(C_5-C_7$cycloalkenyl)$C_1-C_5$alkylene, aryl, aralkyl, trans-$(C_4-C_5)$alkenyl, allyl and furan-2-yl$C_1-C_5$alkylene;

$R^2$ is selected from H, OH and $(C_1-C_5)$alkyl-C(=O)O—;

$R^3$ is selected from H, $(C_1-C_5)$alkyl and $(C_1-C_5)$alkyl-C(=O)—; and $R^4$ and $R^5$ are independently selected from a direct bond to E, H, F, Cl, Br, $NO_2$, CN, $COOR^1$, $NH_2$, $(C_1-C_5)$alkyl, $(C_1-C_5)$alkoxy or together are a benzo ring fused to

, with the proviso that one, but only one, of $R^4$ and $R^5$ may be a direct bond to E; and E is an extender arm, where E provides a stable chain of 2–60 atoms selected from carbon, oxygen, nitrogen and sulfur which covalently links together and distances the groups L and X.

2. A compound of claim 1 wherein L has the formula

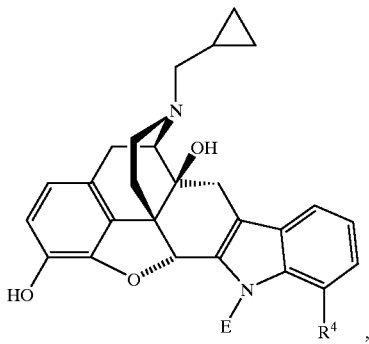

3. A compound of claim 1 wherein L has the formula

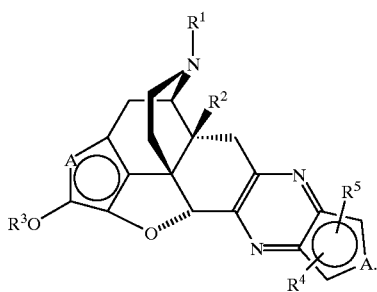

4. A compound comprising a ligand portion (L) which has binding affinity for an opioid receptor, the compound having the structure

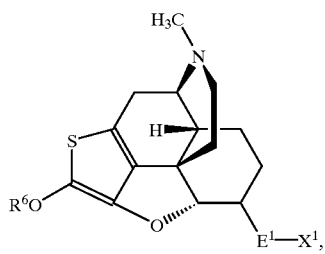

wherein, $R^6$ is selected from H, $C_1-C_5$alkyl and hydroxyl protecting groups;

$E^1$ represents an extender arm (E); and $X^1$ is a radionuclide chelating group.

5. A compound comprising a ligand portion (L) which has binding affinity for an opioid receptor, the compound having the structure

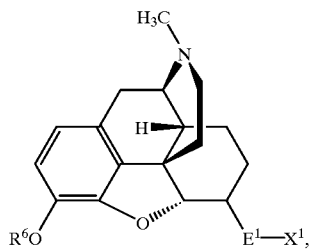

wherein, $R^6$ is selected from H, $C_1-C_5$alkyl and hydroxyl protecting groups;

$E^1$ represents an extender arm (E); and $X^1$ is a radionuclide chelating group.

6. A compound comprising a ligand portion (L) which has binding affinity for an opioid receptor, and a therapeutically or diagnostically effective group (X) selected from radionuclide chelating agents, fluorochromes, toxins, drugs, polyboron moieties, proteins, biological response modifiers, chemical moieties capable of binding to other molecules, and radioisotopes selected from therapeutically effective alpha and beta emitters, and diagnostically effective gamma emitters, the compound having the formula

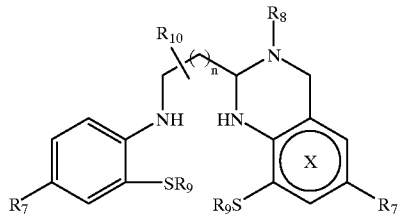

wherein, independently at each occurrence, $R_7$ is selected from —OH, —O—C(=O)—$C_{1-6}$alkyl, and —O—$C_{1-6}$alkyl;

$R_8$ is selected from hydrogen and $C_{1-6}$alkyl;

$R_9$ is selected from hydrogen, —C(=O)—$C_{1-6}$alkyl, —C(=O)-phenyl; hemithioacetals, hemithioketals, and sulfur protecting groups, such that two $R_9$ groups may be joined together as a direct bond, thereby linking two sulfur atoms as a disulfide linkage;

$R_{10}$ is selected from $C_{1-6}$alkyl and $C_{1-6}$alkoxy;

n is selected from 0 and 1; and

represents a 6-membered carbocyclic aromatic or aliphatic ring.

7. A compound comprising a ligand portion (L) which has binding affinity for an opioid receptor, and a therapeutically or diagnostically effective group (X) selected from radionuclide chelating agents, fluorochromes, toxins, drugs, polyboron moieties, proteins, biological response modifiers, chemical moieties capable of binding to other molecules, and radioisotopes selected from therapeutically effective alpha and beta emitters, and diagnostically effective gamma emitters, wherein the ligand portion (Ligand) is conjugated to two X groups $X^1$ and $X^2$, through two extender arms $E^1$ and $E^2$, as represented by the formula

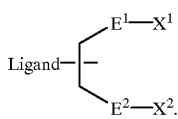

8. The compound of claim 7 wherein $X^1$ and $X^2$ together bind one radionuclide and each has a structure selected from

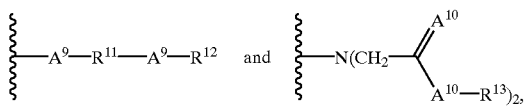

wherein, $A^9$ is an electron-donating moiety independently selected at each occurrence from O, S, C(=O)NH and N($R^{16}$), where $R^{16}$ is selected from hydrogen and pro-drug substituents selected from the group consisting of $C_1$-$C_3$alkyl, —C(=O)(H, $C_1$-$C_3$alkyl or Ar), —C(=O)—($C_1$-$C_3$alkylene)-N(independently H or $C_1$-$C_3$alkyl)$_2$, —C(=O)O—(H, $C_1$-$C_3$alkyl or Ar), —C(=O)CH(NH$_2$)(H, $C_1$-$C_3$alkyl or Ar), —($C_1$-$C_3$alkylene)-C(=O)O—(H, $C_1$-$C_3$alkyl or Ar), —($C_1$-$C_3$alkylene)-OC(=O)—(H, $C_1$-$C_3$alkyl or Ar), —($C_1$-$C_3$alkylene)-N(independently H or $C_1$-$C_3$alkyl)$_2$, —($C_1$-$C_3$alkylene)-NHC(=O)—Ar, —($C_{1-3}$alkylene)-CN, —($C_{1-3}$alkylene)-NO$_2$, and

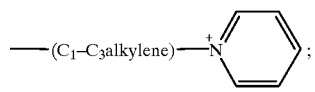

$R^{11}$ has a structure selected from

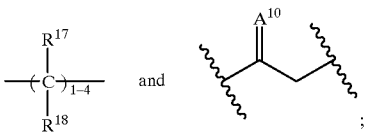

$R^{17}$ and $R^{18}$ are selected from H, $C_1$-$C_6$hydrocarbyl, —CN, —NO$_2$, —NO, —C(O$C_1$-$C_3$alkyl)=NH, —N=C=O, —N=C=S, and —C(=O)O$R^{19}$ where $R^{19}$ is $C_1$-$C_6$hydrocarbyl;

$R^{12}$ and $R^{13}$ are selected from H and protecting groups for the $A^9$ or $A^{10}$ moiety to which the $R^{12}$ or $R^{13}$ is bonded;

$A^9$ and $R^{12}$ may together form —N(CH$_2$—COOH)$_2$; and $A^{10}$ is selected from O and S.

9. The compound of claim 7 having the formula

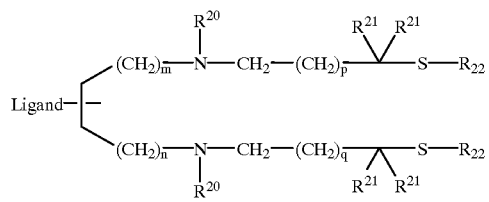

wherein $R^{20}$ and $R^{21}$ are independently selected from hydrogen and methyl;

$R^{22}$ is independently selected from hydrogen, acm, EOE, THP, $C_1$-$C_6$alkyl, acetate, benzoyl and sulfur protecting groups; and each of m, n, p and q are selected from 0 and 1 such that when p+q=0 then m+n=0 or 1; and when p+q=1 then m+n=1; and when p+q=2 then m+n=1 or 2.

10. The compound of claim 7 wherein $X^1$ and $X^2$ together form the cyclic structure

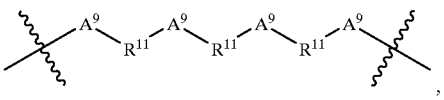

wherein, $A^9$ is an electron-donating moiety independently selected at each occurrence from O, S, C(=O)NH and N($R^{12}$), where $R^{12}$ is selected from hydrogen and pro-drug substituents selected from the group consisting of $C_1$-$C_3$alkyl, —C(=O)(H, $C_1$-$C_3$alkyl or Ar), —C(=O)-($C_1$-$C_3$alkylene)-N(independently H or $C_1$-$C_3$alkyl)$_2$, —C(=O)O—(H, $C_1$-$C_3$alkyl or Ar), —C(=O)CH(NH$_2$)(H, $C_1$-$C_3$alkyl or Ar), —($C_1$-$C_3$alkylene)-C(=O)O—(H, $C_1$-$C_3$alkyl or Ar), —($C_1$—$C_3$alkylene)-OC(=O)—(H, $C_1$-$C_3$alkyl or Ar), —($C_1$—$C_3$alkylene)-N(independently H or $C_1$-$C_3$alkyl)$_2$, —($C_1$-$C_3$alkylene)-NHC(=O)—Ar, —($C_1$-$C_3$alkylene)-CN, —($C_1$-$C_3$alkylene)-NO$_2$, and

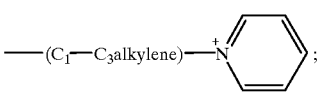

$R^{11}$ has a structure selected from

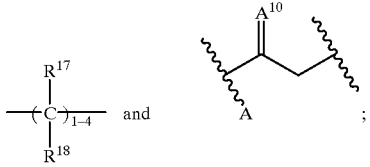
and
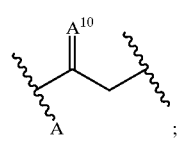
;

$R^{17}$ and $R^{18}$ are selected from H, $C_1$-$C_6$hydrocarbyl, —CN, —$NO_2$, —NO, —C(O$C_1$-$C_3$alkyl)=NH, —N=C=O, —N=C=S, and —C(=O)O$R^{19}$ where $R^{19}$ is $C_1$-$C_6$hydrocarbyl;

$A^9$ and $R^{12}$ may together form —N(CH$_2$—COOH)$_2$; and $A^{10}$ is selected from O and S.

11. A compound comprising a ligand portion (L) which has binding affinity for an opioid receptor, and a therapeutically or diagnostically effective group (X) selected from radionuclide chelating agents, fluorochromes, toxins, drugs, polyboron moieties, proteins, biological response modifiers, chemical moieties capable of binding to other molecules, and radioisotopes selected from therapeutically effective alpha and beta emitters, and diagnostically effective gamma emitters, wherein the ligand portion (Ligand) is conjugated at one site to an X group through an extender arm E, as represented by the formula Ligand-E-X, wherein X is represented by any of formulas (II), (III) or (IV), (II)

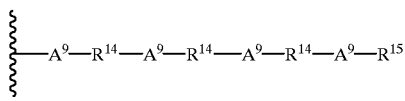

(III)

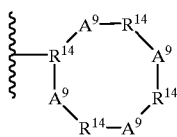

(IV)

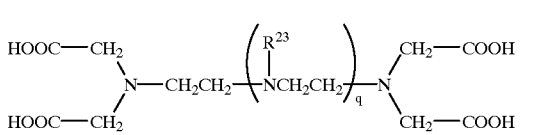

such that one methylene hydrogen of formula (IV) is replaced with a direct bond to E;

where, independently at each occurrence, $A^9$ is an electron-donating moiety selected from O, S, C(=O)NH and N($R^{16}$), where $R^{16}$ is selected from hydrogen and pro-drug substituents selected from $C_1$-$C_3$alkyl, —C(=O)(H, $C_1$-$C_3$alkyl or Ar), —C(=O)—($C_1$-$C_3$alkylene)-N(independently H or $C_1$-$C_3$alkyl)$_2$, —C(=O)O—(H, $C_1$-$C_3$alkyl or Ar), —C(=O)CH(NH$_2$)(H, $C_1$—$C_3$alkyl or Ar), —($C_1$-$C_3$alkylene)-C(=O)O—(H, $C_1$-$C_3$alkyl or Ar), —($C_1$-$C_3$alkylene)-OC(=O)—(H, $C_1$-$C_3$alkyl or Ar), —($C_1$—$C_3$alkylene)-N(independently H or $C_1$—$C_3$alkyl)$_2$, —($C_1$-$C_3$alkylene)-NHC(=O)—Ar, —($C_1$-$C_3$alkylene)-CN, —($C_1$—$C_3$alkylene)-NO$_2$, and

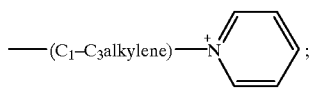

$R^{14}$ is selected from

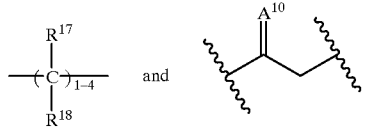

where $R^{17}$ and $R^{18}$ are selected from H, $C_1$-$C_6$hydrocarbyl, —CN, —NO$_2$, —NO, —C(O$C_1$-$C_3$alkyl)=NH, —N=C=O, —N=C=S, and —C(=O)O$R^{19}$ where $R^{19}$ is $C_1$-$C_6$hydrocarbyl;

$A^{10}$ is selected from O and S;

$R^{15}$ is selected from H and protecting groups for $A^9$, where $A^9$ and $R^{15}$ may together form —N(CH$_2$—COOH)$_2$;

$R^{23}$ is selected from H and CH$_2$COOH;

q is selected from 0, 1, 2 and 3; and

E represents an extender arm through which L is conjugated to X.

12. A compound of claim 11 wherein X has the formula

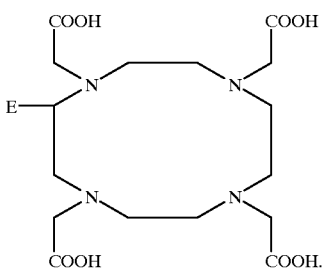

13. A compound of claim 11 wherein X has the formula

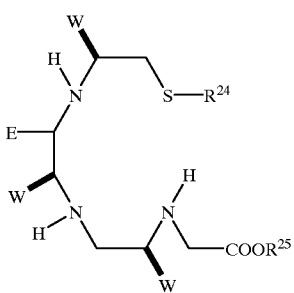

where W represents H$_2$ or =O, $R^{24}$ is selected from H, COCH$_3$, EOE, THP, COPh, acm, $C_1$-$C_6$hydrocarbyl, and sulfur protecting groups; and $R^{25}$ is selected from H and $C_1$-$C_6$hydrocarbyl.

14. A compound of claim 11 wherein X has the formula

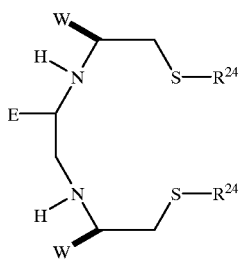

where W represents $H_2$ or $=O$, and $R^{24}$ is selected from H, $COCH_3$, EOE, THP, COPh, acm, $C_1$–$C_6$hydrocarbyl, and sulfur protecting groups.

15. A compound comprising a ligand portion (L) which has binding affinity for an opioid receptor, and a therapeutically or diagnostically effective group (X) selected from radionuclide chelating agents, fluorochromes, toxins, drugs, polyboron moieties, proteins, biological response modifiers, chemical moieties capable of binding to other molecules, and radioisotopes selected from therapeutically effective alpha and beta emitters, and diagnostically effective gamma emitters, wherein L is conjugated to an X group through an extender arm (E), where E provides a stable chain of 2–60 atoms selected from carbon, oxygen, nitrogen and sulfur which covalently links together and distances the groups L and X, and E has a formula selected from

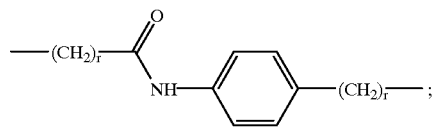

$=N$—(NH or NHCO)—$(CH_2)_r$—.

$=N$—(O, NH, or direct bond)-$E^3$-(phenylene or direct bond-$(CH_2)_r$—;

—(O, S, or Se)—$E^3$—;

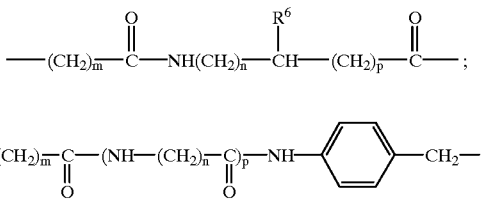

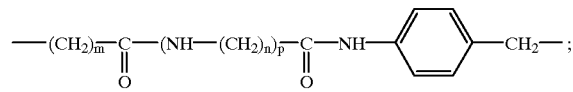

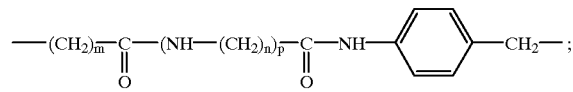

where m is selected from 0, 1, 2, 3, 4 and 5; n is selected from 1, 2, 3, 4 and 5; p is selected from 0, 1, 2, 3 and 4; r is an integer of from 1 to about 4; and $E^3$ is a 1–10 carbon moiety having 0–3 heteroatoms as ethers or ester;

$R^6$ is selected from H, $C_1$–$C_5$alkyl and hydroxyl protecting groups; and wherein X is NY and Y is selected from H, $(C_1$–$C_5)$alkyl and a direct bond to E.

16. The compound of claim 4 wherein $R^6$ is acetate protecting group.

17. The compound of claim 5 wherein $R^6$ is acetate protecting group.

* * * * *

UNITED STATES PATENT AND TRADEMARK OFFICE
CERTIFICATE OF CORRECTION

PATENT NO.    : 6,359,111 B1
DATED         : March 19, 2002
INVENTOR(S)   : Damon L. Meyer et al.

It is certified that error appears in the above-identified patent and that said Letters Patent is hereby corrected as shown below:

Column 57,
Line 47, the following formula:

"
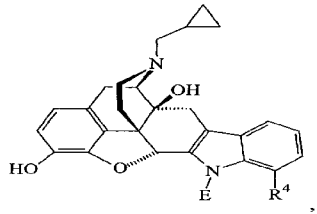
"

should be corrected to read --

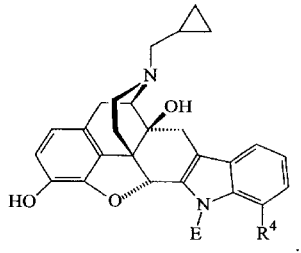

--.

Column 61,
Line 7, the following formula:

"
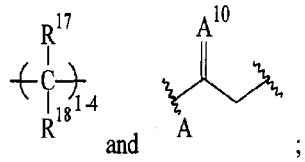
"

should be corrected to read --

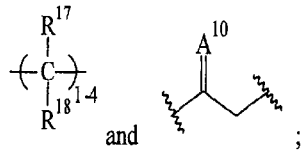

--.

UNITED STATES PATENT AND TRADEMARK OFFICE
CERTIFICATE OF CORRECTION

PATENT NO. : 6,359,111 B1
DATED : March 19, 2002
INVENTOR(S) : Damon L. Meyer et al.

It is certified that error appears in the above-identified patent and that said Letters Patent is hereby corrected as shown below:

<u>Column 63,</u>
Line 37, the following formula:

"  $=N-(NH \text{ or } NHCO)-(CH_2)_r-$  "

should be corrected to read --

$=N-(NH \text{ or } NHCO)-(CH_2)_r-$ ;

--.

Signed and Sealed this

Twelfth Day of November, 2002

Attest:

JAMES E. ROGAN
Attesting Officer   Director of the United States Patent and Trademark Office

UNITED STATES PATENT AND TRADEMARK OFFICE
CERTIFICATE OF CORRECTION

PATENT NO.  : 6,359,111 B1
DATED       : March 19, 2002
INVENTOR(S) : Damon L. Meyer et al.

It is certified that error appears in the above-identified patent and that said Letters Patent is hereby corrected as shown below:

Column 9,
Line 5, the following formula:

"
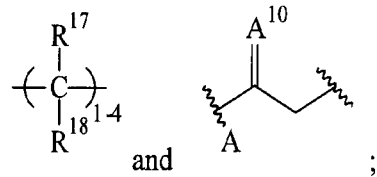
"

should read --

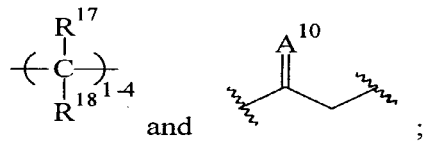

--.

UNITED STATES PATENT AND TRADEMARK OFFICE
CERTIFICATE OF CORRECTION

PATENT NO. : 6,359,111 B1
DATED : March 19, 2002
INVENTOR(S) : Damon L. Meyer et al.

It is certified that error appears in the above-identified patent and that said Letters Patent is hereby corrected as shown below:

Column 11,
Line 10, the following formula:

"
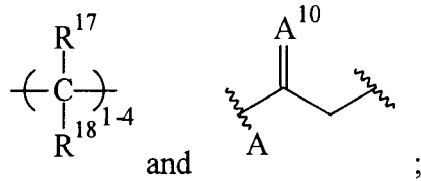
"

should read --

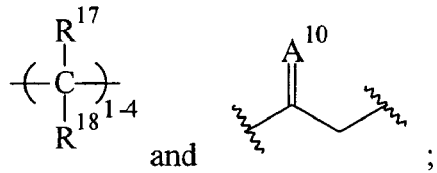

--.

Signed and Sealed this

Twenty-seventh Day of May, 2003

JAMES E. ROGAN
*Director of the United States Patent and Trademark Office*